US 11,298,540 B2

(12) United States Patent
Rondoni et al.

(10) Patent No.: US 11,298,540 B2
(45) Date of Patent: Apr. 12, 2022

(54) CUFF ELECTRODE

(71) Applicant: INSPIRE MEDICAL SYSTEMS, INC., Golden Valley, MN (US)

(72) Inventors: John Rondoni, Golden Valley, MN (US); Kevin Verzal, Golden Valley, MN (US); David Dieken, Golden Valley, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 110 days.

(21) Appl. No.: 16/485,954

(22) PCT Filed: Aug. 9, 2018

(86) PCT No.: PCT/US2018/046100
§ 371 (c)(1),
(2) Date: Aug. 14, 2019

(87) PCT Pub. No.: WO2019/032890
PCT Pub. Date: Feb. 14, 2019

(65) Prior Publication Data
US 2020/0230412 A1 Jul. 23, 2020

Related U.S. Application Data

(60) Provisional application No. 62/544,140, filed on Aug. 11, 2017.

(51) Int. Cl.
A61N 1/05 (2006.01)
A61N 1/36 (2006.01)

(52) U.S. Cl.
CPC ....... *A61N 1/36078* (2013.01); *A61N 1/0556* (2013.01); *A61N 1/36167* (2013.01); *A61N 1/36185* (2013.01)

(58) Field of Classification Search
CPC .............. A61N 1/36078; A61N 1/0556; A61N 1/36167; A61N 1/36185
See application file for complete search history.

(56) References Cited

U.S. PATENT DOCUMENTS 3,654,933 A 4/1972 Hagfors
4,379,462 A 4/1983 Borkan
4,512,351 A 4/1985 Pohndorf
(Continued)

FOREIGN PATENT DOCUMENTS

EP 0865800 9/1998
WO 2007140597 12/2007
(Continued)

OTHER PUBLICATIONS

Walter, James & Griffith, Patricia & Scarpine, Victor & Bidnar, Michael & Dauzvardis, Michael & Turner, Michael & McLane, Jerry & Sweeney, James & Robinson, Charles. (1996). The Raccoon as an Animal Model for Upper Limb Neural Prosthetics. The journal of spinal cord medicine. 19. 234-41. 10.1080/1079 (Year: 1996).*
(Continued)

*Primary Examiner* — Shirley X Jian
(74) *Attorney, Agent, or Firm* — Dicke, Billig & Czaja, PLLC

(57) ABSTRACT

A cuff electrode includes at least an array of electrodes to extend circumferentially about a nerve, and methods of making and using a cuff electrode.

25 Claims, 30 Drawing Sheets

(56) References Cited

U.S. PATENT DOCUMENTS

| | | | |
|---|---|---|---|
| 4,567,892 A | 2/1986 | Plicchi | |
| 4,590,946 A | 5/1986 | Loeb | |
| 4,602,624 A | 7/1986 | Naples et al. | |
| 4,628,614 A | 12/1986 | Thompson | |
| 4,960,133 A | 10/1990 | Hewson | |
| 4,967,755 A | 11/1990 | Pohndorf | |
| 5,158,080 A | 10/1992 | Kallok | |
| 5,178,156 A | 1/1993 | Takishima | |
| 5,265,624 A | 11/1993 | Bpwman | |
| 5,282,468 A | 2/1994 | Klepinski | |
| 5,324,322 A | 6/1994 | Grill, Jr. et al. | |
| 5,344,438 A | 9/1994 | Testerman | |
| 5,351,394 A | 10/1994 | Weinberg | |
| 5,358,514 A | 10/1994 | Schulman et al. | |
| 5,398,596 A | 3/1995 | Fond | |
| 5,400,784 A | 3/1995 | Durand et al. | |
| 5,487,756 A | 1/1996 | Kallesoe et al. | |
| 5,505,201 A | 4/1996 | Grill, Jr. et al. | |
| 5,531,778 A | 7/1996 | Maschino | |
| 5,540,734 A | 7/1996 | Zabara | |
| 5,591,216 A | 1/1997 | Testerman et al. | |
| 5,634,462 A | 6/1997 | Tyler et al. | |
| 5,741,319 A | 4/1998 | Woloszko et al. | |
| 5,824,027 A | 10/1998 | Hoffer et al. | |
| 5,938,596 A * | 8/1999 | Woloszko | A61N 1/0556 |
| | | | 600/377 |
| 6,015,389 A | 1/2000 | Brown | |
| 6,041,780 A | 3/2000 | Richard | |
| 6,093,197 A | 7/2000 | Bakula et al. | |
| 6,366,815 B1 | 4/2002 | Haugland | |
| 6,456,866 B1 | 9/2002 | Tyler et al. | |
| 6,587,725 B1 | 7/2003 | Durand et al. | |
| 6,600,956 B2 | 7/2003 | Maschino | |
| 6,647,289 B2 | 11/2003 | Prutchi | |
| 6,651,652 B1 | 11/2003 | Ward | |
| 6,907,293 B2 | 6/2005 | Grill | |
| 6,904,320 B2 | 7/2005 | Park | |
| 6,907,295 B2 | 7/2005 | Gross | |
| 6,928,324 B2 | 8/2005 | Park | |
| 6,978,171 B2 | 12/2005 | Goetz | |
| 7,054,692 B1 | 5/2006 | Whitehurst et al. | |
| 7,065,410 B2 | 7/2006 | Bardy | |
| 7,082,331 B1 | 7/2006 | Park | |
| 7,082,336 B2 | 7/2006 | Ransbury et al. | |
| 7,087,053 B2 | 8/2006 | Vanney | |
| 7,117,036 B2 | 10/2006 | Florio | |
| 7,128,717 B1 | 10/2006 | Thatch | |
| 7,149,573 B2 | 12/2006 | Wang | |
| 7,160,255 B2 | 1/2007 | Saadat | |
| 7,200,440 B2 | 4/2007 | Kim | |
| 7,248,930 B1 * | 7/2007 | Woloszko | A61N 1/05 |
| | | | 600/377 |
| 7,366,572 B2 | 4/2008 | Heruth | |
| 7,395,119 B2 | 7/2008 | Hagen et al. | |
| 7,463,928 B2 | 12/2008 | Lee | |
| 7,463,934 B2 | 12/2008 | Tronnes et al. | |
| 7,473,227 B2 | 1/2009 | Hsu | |
| 7,499,742 B2 | 3/2009 | Bolea et al. | |
| 7,591,265 B2 | 9/2009 | Lee | |
| 7,596,413 B2 | 9/2009 | Libbus | |
| 7,596,414 B2 | 9/2009 | Whitehurst | |
| 7,630,771 B2 | 12/2009 | Cauller | |
| 7,634,315 B2 | 12/2009 | Cholette | |
| 7,644,714 B2 | 1/2010 | Atkinson et al. | |
| 7,662,105 B2 | 2/2010 | Hatlestad | |
| 7,672,728 B2 | 3/2010 | Libbus | |
| 7,680,538 B2 | 3/2010 | Durand et al. | |
| 7,717,848 B2 | 5/2010 | Heruth | |
| 7,734,340 B2 | 6/2010 | DeRidder | |
| 7,747,323 B2 | 6/2010 | Libbus | |
| 7,751,880 B1 | 7/2010 | Cholette | |
| 7,783,353 B2 | 8/2010 | Libbus | |
| 7,787,959 B1 | 8/2010 | Morgan | |
| 7,809,442 B2 * | 10/2010 | Bolea | A61N 1/3606 |
| | | | 607/42 |
| 7,818,063 B2 | 10/2010 | Wallace | |
| 7,974,705 B2 * | 7/2011 | Zdeblick | A61N 1/0551 |
| | | | 607/117 |
| 8,155,757 B1 * | 4/2012 | Neisz | A61N 1/0556 |
| | | | 607/118 |
| 8,311,645 B2 * | 11/2012 | Bolea | A61N 1/37229 |
| | | | 607/118 |
| 8,340,785 B2 * | 12/2012 | Bonde | A61N 1/0558 |
| | | | 607/118 |
| 9,227,053 B2 * | 1/2016 | Bonde | A61N 1/0558 |
| 10,898,092 B2 * | 1/2021 | Schuttler | A61B 5/24 |
| 2001/0010010 A1 | 7/2001 | Richmond et al. | |
| 2002/0010495 A1 | 1/2002 | Freed et al. | |
| 2002/0049479 A1 | 4/2002 | Pitts | |
| 2002/0156507 A1 | 10/2002 | Lindenthaler | |
| 2003/0093128 A1 | 5/2003 | Freed et al. | |
| 2003/0114895 A1 | 6/2003 | Gordon et al. | |
| 2003/0114905 A1 | 6/2003 | Kuzma | |
| 2003/0195571 A1 | 10/2003 | Burnes et al. | |
| 2003/0216789 A1 | 11/2003 | Deem et al. | |
| 2004/0024439 A1 * | 2/2004 | Riso | A61N 1/0556 |
| | | | 607/117 |
| 2004/0073272 A1 | 4/2004 | Knudson et al. | |
| 2004/0111139 A1 | 6/2004 | McCreery | |
| 2005/0004610 A1 | 1/2005 | Kim | |
| 2005/0010265 A1 | 1/2005 | Baru Fassio | |
| 2005/0085865 A1 | 4/2005 | Tehrani | |
| 2005/0085866 A1 | 4/2005 | Tehrani | |
| 2005/0085868 A1 | 4/2005 | Tehrani | |
| 2005/0085869 A1 | 4/2005 | Tehrani | |
| 2005/0101833 A1 | 5/2005 | Hsu | |
| 2005/0165457 A1 | 7/2005 | Benser | |
| 2005/0209513 A1 | 9/2005 | Heruth | |
| 2005/0209643 A1 | 9/2005 | Heruth | |
| 2005/0234523 A1 | 10/2005 | Levin | |
| 2005/0261747 A1 | 11/2005 | Schuler | |
| 2005/0027800 A1 | 12/2005 | Strother | |
| 2005/0267380 A1 | 12/2005 | Poezevara | |
| 2005/0277844 A1 | 12/2005 | Strother | |
| 2005/0277999 A1 | 12/2005 | Strother | |
| 2006/0030919 A1 * | 2/2006 | Mrva | A61N 1/0556 |
| | | | 607/118 |
| 2006/0058852 A1 | 3/2006 | Koh | |
| 2006/0064029 A1 | 3/2006 | Arad | |
| 2006/0078902 A1 | 4/2006 | Jensen | |
| 2006/0095088 A1 | 5/2006 | DeRidder | |
| 2006/0103407 A1 | 5/2006 | Kakizawa et al. | |
| 2006/0135886 A1 | 6/2006 | Lippert | |
| 2006/0142815 A1 | 6/2006 | Tehrani | |
| 2006/0167497 A1 | 7/2006 | Armstrong | |
| 2006/0184204 A1 | 8/2006 | He | |
| 2006/0195170 A1 | 8/2006 | Cohen | |
| 2006/0247729 A1 | 11/2006 | Tehrani | |
| 2006/0259079 A1 | 11/2006 | King | |
| 2006/0266369 A1 | 11/2006 | Atkinson et al. | |
| 2006/0271137 A1 * | 11/2006 | Stanton-Hicks | A61N 1/0551 |
| | | | 607/118 |
| 2006/0282127 A1 | 12/2006 | Zealear | |
| 2006/0293720 A1 | 12/2006 | DiLorenzo | |
| 2006/0293723 A1 | 12/2006 | Whitehurst | |
| 2007/0021785 A1 | 1/2007 | Inman | |
| 2007/0255379 A1 | 1/2007 | Williams et al. | |
| 2007/0027482 A1 | 2/2007 | Parnis | |
| 2007/0038265 A1 | 2/2007 | Tcheng | |
| 2007/0043411 A1 | 2/2007 | Foster | |
| 2007/0129780 A1 | 6/2007 | Whitehurst et al. | |
| 2007/0233204 A1 | 10/2007 | Lima et al. | |
| 2007/0239243 A1 | 10/2007 | Moffitt et al. | |
| 2008/0046055 A1 | 2/2008 | Durand et al. | |
| 2008/0103407 A1 * | 5/2008 | Bolea | A61N 1/3606 |
| | | | 600/529 |
| 2008/0103545 A1 * | 5/2008 | Bolea | A61N 1/37229 |
| | | | 607/42 |
| 2008/0103570 A1 | 5/2008 | Gerber | |
| 2008/0132987 A1 | 6/2008 | Westlund et al. | |
| 2008/0172101 A1 | 7/2008 | Bolea et al. | |
| 2008/0172116 A1 | 7/2008 | Mrva et al. | |
| 2008/0177348 A1 | 7/2008 | Bolea et al. | |

(56) References Cited

U.S. PATENT DOCUMENTS

| | | | |
|---|---|---|---|
| 2008/0319506 A1 | 12/2008 | Cauller | |
| 2009/0099439 A1 | 4/2009 | Barolat | |
| 2009/0210042 A1 | 8/2009 | Kowalczewski | |
| 2009/0308395 A1 | 12/2009 | Lee | |
| 2009/0326408 A1 | 12/2009 | Moon | |
| 2010/0010603 A1 | 1/2010 | Ben-David et al. | |
| 2010/0094379 A1* | 4/2010 | Meadows | A61B 5/08 607/48 |
| 2010/0114240 A1 | 5/2010 | Guntinas-Lichlus et al. | |
| 2010/0121405 A1 | 5/2010 | Ternes et al. | |
| 2010/0125310 A1 | 5/2010 | Wilson | |
| 2010/0137931 A1 | 6/2010 | Hopper | |
| 2010/0145221 A1 | 6/2010 | Brunnett et al. | |
| 2010/0152553 A1 | 6/2010 | Ujhazy | |
| 2010/0174341 A1 | 7/2010 | Bolea et al. | |
| 2010/0198103 A1 | 8/2010 | Meadows et al. | |
| 2010/0222844 A1 | 9/2010 | Troosters et al. | |
| 2010/0228133 A1 | 9/2010 | Averina | |
| 2010/0228317 A1 | 9/2010 | Libbus | |
| 2010/0241195 A1 | 9/2010 | Meadows et al. | |
| 2010/0241207 A1* | 9/2010 | Bluger | A61B 5/287 607/118 |
| 2011/0066254 A1* | 3/2011 | Forsell | A61M 60/873 623/23.64 |
| 2011/0093036 A1* | 4/2011 | Mashiach | A61N 1/0553 607/48 |
| 2011/0147046 A1* | 6/2011 | Bonde | A61N 1/0558 174/126.1 |
| 2012/0130463 A1 | 5/2012 | Ben-David et al. | |
| 2013/0123895 A1* | 5/2013 | Bonde | A61N 1/0558 607/118 |
| 2013/0231726 A1* | 9/2013 | Johnson | A61N 1/37217 607/118 |
| 2014/0074213 A1* | 3/2014 | Neisz | A61N 1/0556 607/118 |
| 2017/0239462 A1* | 8/2017 | Govea | A61N 1/3752 |
| 2018/0221660 A1 | 8/2018 | Suri et al. | |
| 2018/0318578 A1 | 11/2018 | Ng et al. | |
| 2019/0060646 A1 | 2/2019 | Ng et al. | |
| 2020/0230399 A1 | 7/2020 | Zaidi et al. | |
| 2020/0230421 A1 | 7/2020 | Zaidi et al. | |
| 2020/0316372 A1 | 10/2020 | Bashirullah et al. | |
| 2020/0384265 A1 | 12/2020 | Donega et al. | |
| 2021/0085964 A1 | 3/2021 | Zaidi et al. | |
| 2021/0085965 A1 | 3/2021 | Zaidi et al. | |
| 2021/0093867 A1 | 4/2021 | Donega et al. | |
| 2021/0093868 A1 | 4/2021 | Hunsberger | |
| 2021/0138238 A1 | 5/2021 | Holder et al. | |

FOREIGN PATENT DOCUMENTS

| | | |
|---|---|---|
| WO | 2008025155 | 3/2008 |
| WO | 2008048471 | 4/2008 |
| WO | 2009048580 | 4/2009 |
| WO | 2009048581 | 4/2009 |
| WO | 2009135138 | 11/2009 |
| WO | 2009135140 | 11/2009 |
| WO | 2009135142 | 11/2009 |
| WO | 2009140636 | 11/2009 |
| WO | 2010039853 | 4/2010 |
| WO | 2010059839 | 5/2010 |
| WO | 2010117810 | 10/2010 |
| WO | 2011112843 | 9/2011 |
| WO | 2017087681 | 5/2017 |
| WO | 2020128748 A1 | 6/2020 |
| WO | 2021105699 A1 | 6/2021 |

OTHER PUBLICATIONS

Taghipour, Hamed & Frounchi, Javad & Ahmadiasl, Nasser & Shahabi, Parviz & Salekzamani, Yaghoub. (2015). Effect of contacts configuration and location on selective stimulation of cuff electrode. Bio-Medical Materials and Engineering. 25. 237-248. 10.3233/BME-151281. (Year: 2015).*

Eisele Article—David W. Eisele, MD et al., "Tongue neuromuscular and direct hypoglossal nerve stimulation for obstructive sleep apnea," Otolaryngologic Clinics of North America, Otolayngol Clin N Am 36 (2003) 501-510 (10 pages).

Goodall Article—Eleanor V. Goodhall et al., "Position-Selective Activation of Peripheral Nerve Fibers with a Cuff Electrode," IEEE Transaction on Biomedical Engineering, vol. 43, No. 8, Aug. 1996, pp. 851-856.

Oliven Article—Arie Oliven et al., "Upper airway response to electrical stimulation of the genioglossus in obstructive sleep apnea," Journal of Applied Physiology, vol. 95, pp. 2023-2029, Nov. 2003, www.jap.physiology.org on Sep. 18, 2006. (8 pages).

Schwartz Article—Alan R. Schwartz MD et al., Theraputic Electrical Stimulation of the Hypoglossal Nerve in Obstructive Sleep Apnea, Arch Otolaryngol HeadAnd Neck Surg., vol. 127, Oct. 2001, pp. 1216-1223. Copyright 2001 American Medical Association. (8 pages).

PARK Article—"Preoperative Percutaneous Cranial Nerve Mapping in Head and Neck Surgery," Arch Facial Plast Surg/vol. 5, Jan./Feb. 2003, www.arctifacial.compp. 86-91.

Naples Article—Gregory G. Naples et al., "A Spiral Nerve Cuff Electrode for Peripheral Nerve Stimulation," 8088 IEEE Transactions on Biomedical Engineering, 35. Nov. 1988, No. 11, New York, NY, pp. 905-915.

Yoo Article—Paul B. Yoo et al., "Effects of Selective Hypoglossal Nerve Stimulation on Canine Upper Airway Mechanics," J Appl Physiol 99, Apr. 2005, pp. 937-943.

Yoo Article—Paul B. Yoo et al., "Selective Stimulation of the Canine Hypoglossal Nerve Using a Multi-Contact Cuff Electrode," Annals of Biomedical Engineering, vol. 32, No. 4, Apr. 2004, pp. 511-519.

* cited by examiner

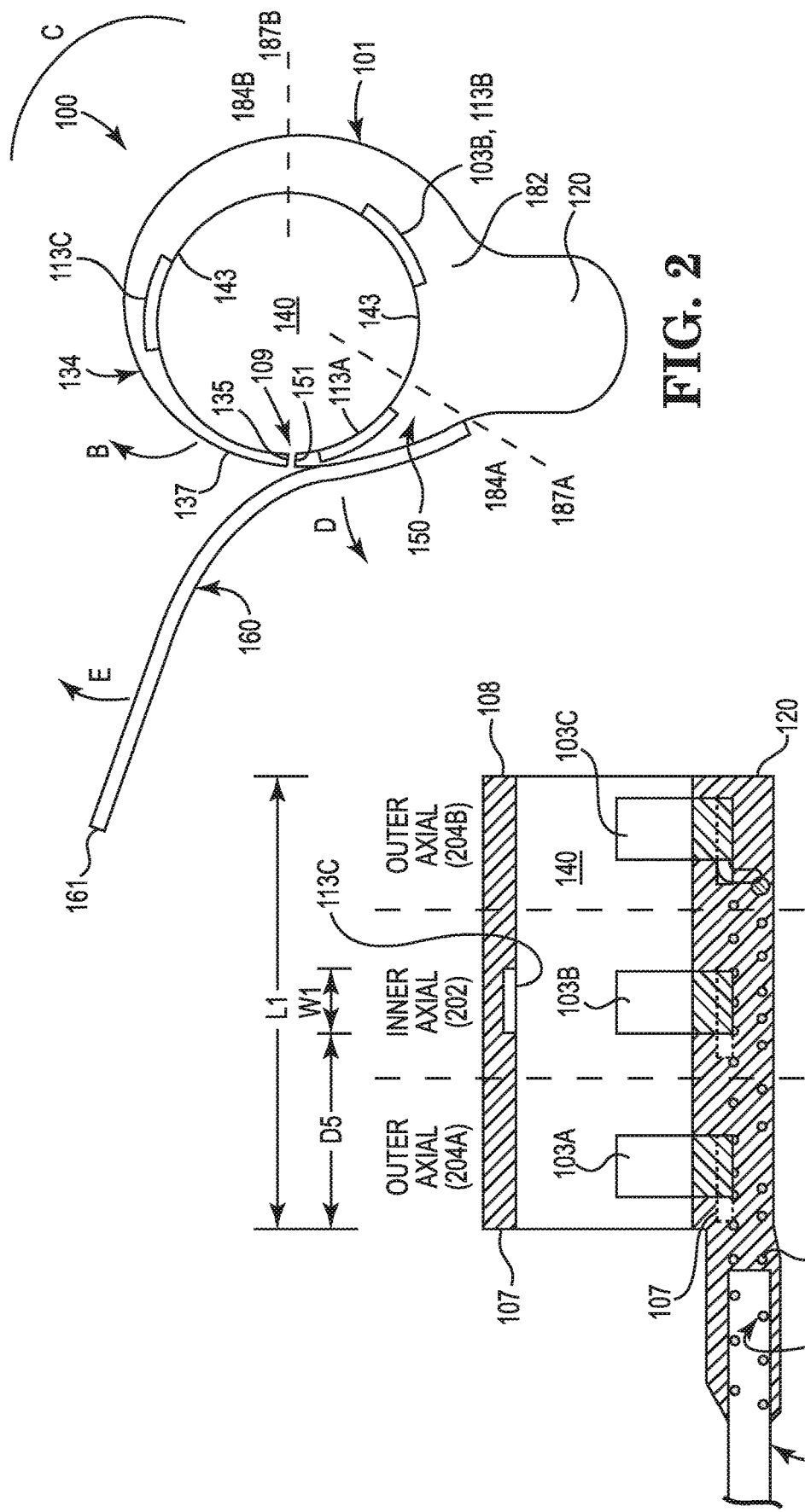

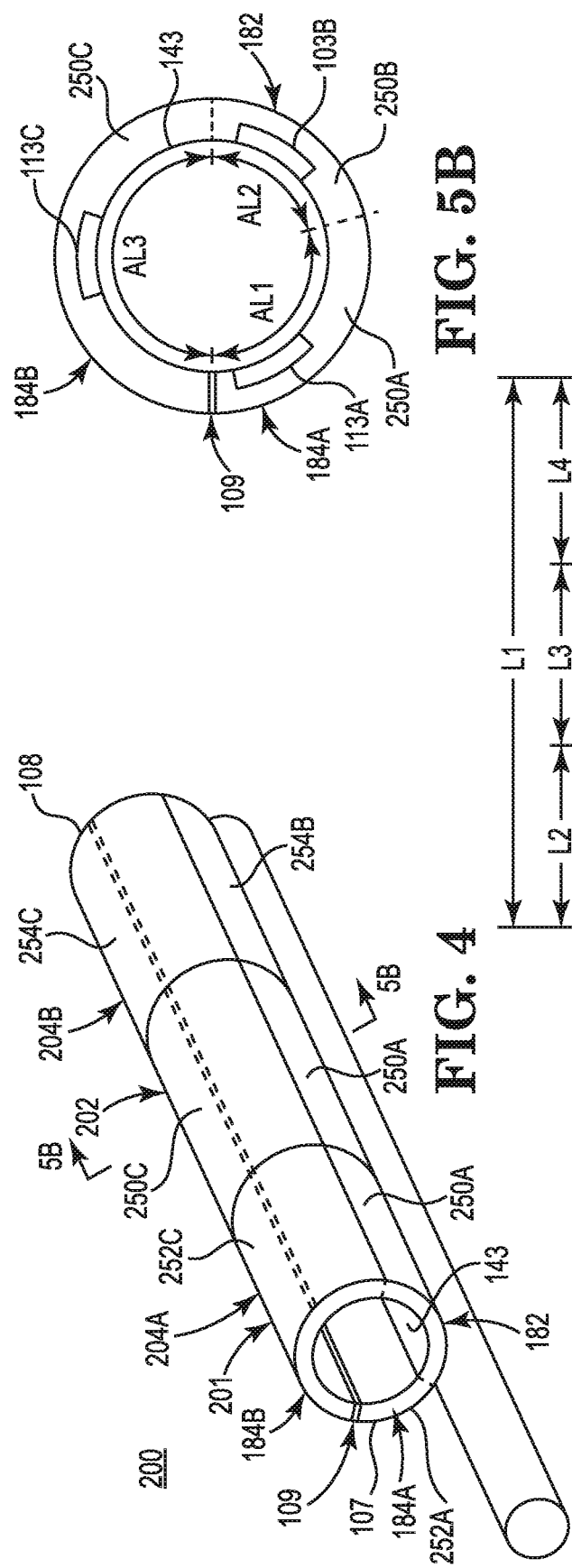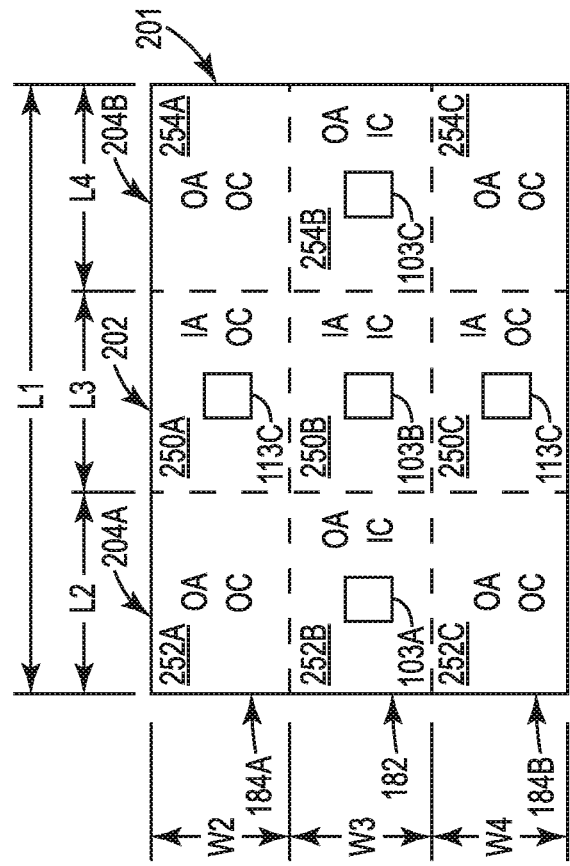
FIG. 5B
FIG. 4
FIG. 5A

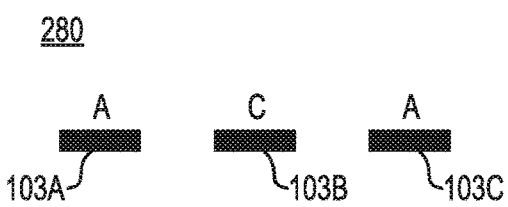 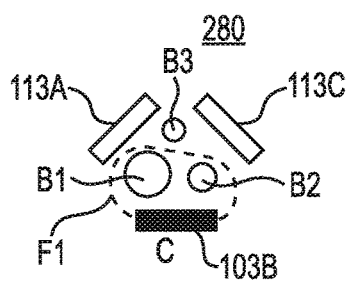
FIG. 7A    FIG. 7B
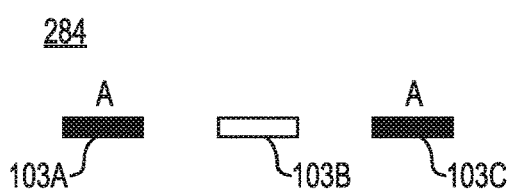 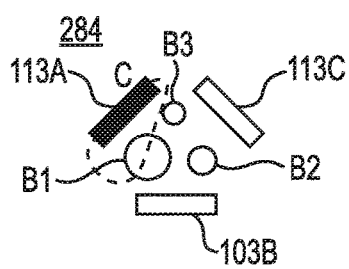
FIG. 7C    FIG. 7D
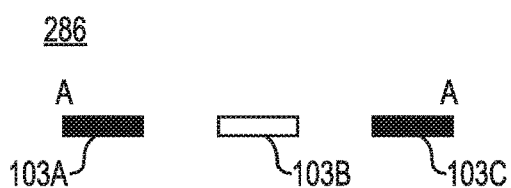 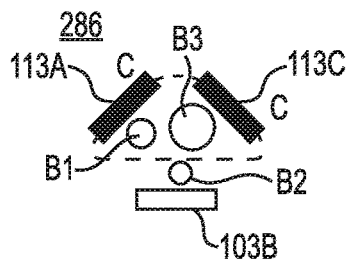
FIG. 7E    FIG. 7F
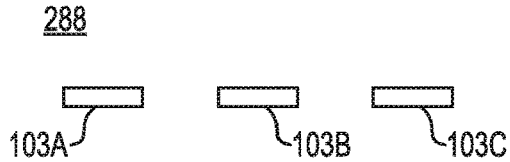 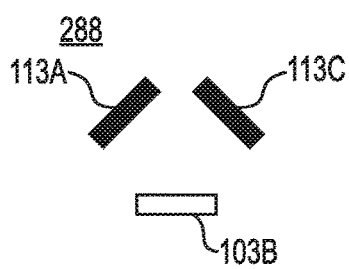
FIG. 7G    FIG. 7H
 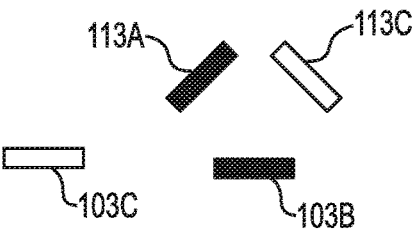 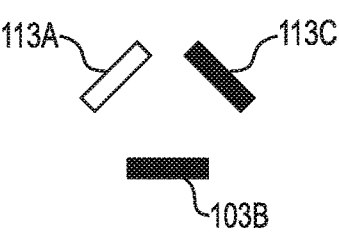
FIG. 7I    FIG. 7J    FIG. 7K

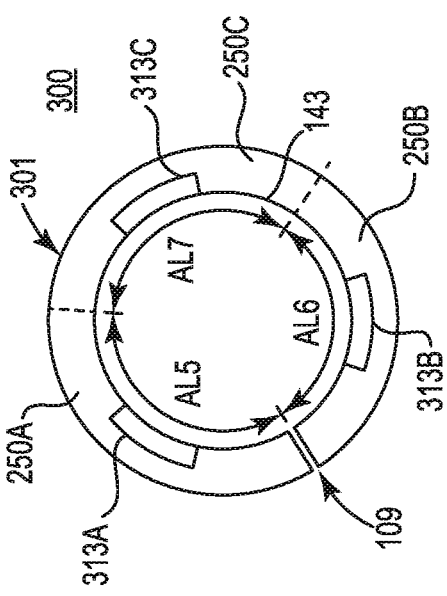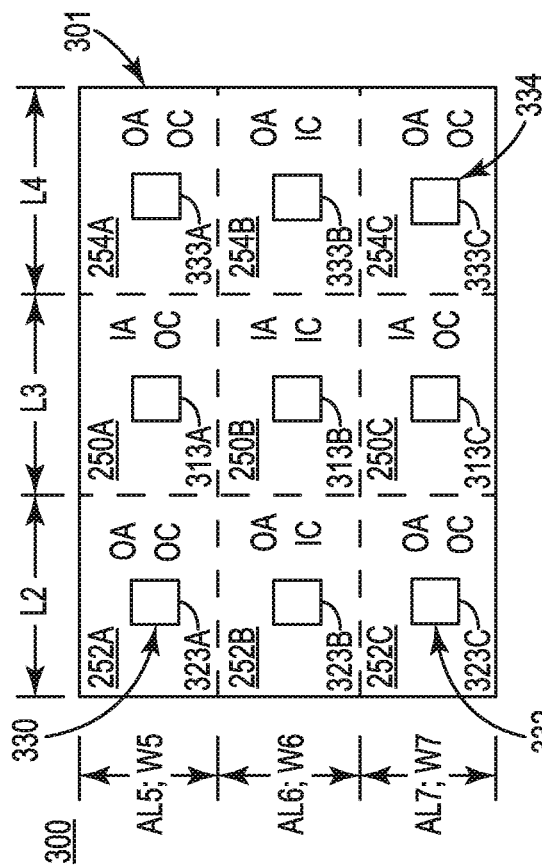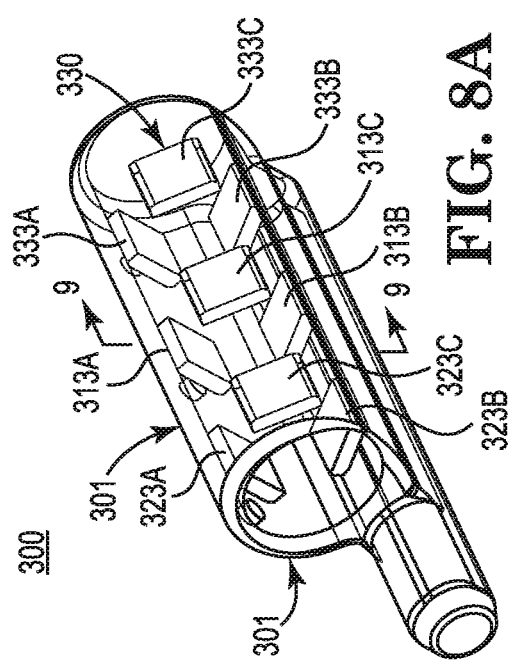

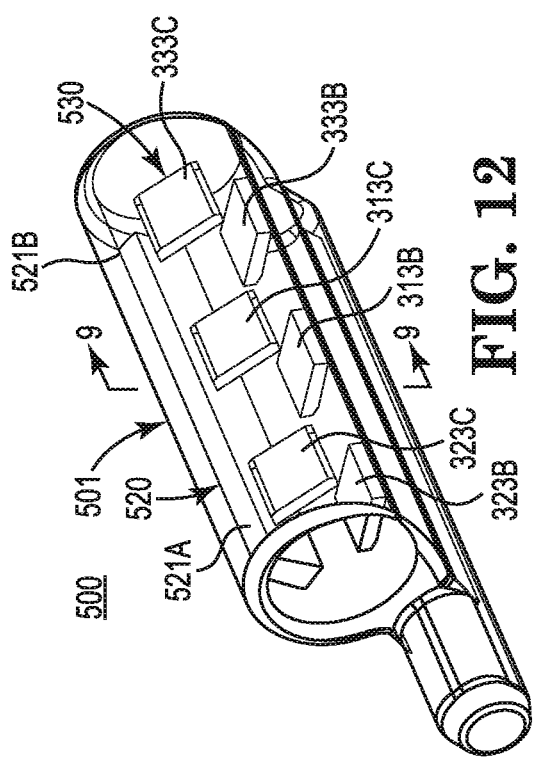
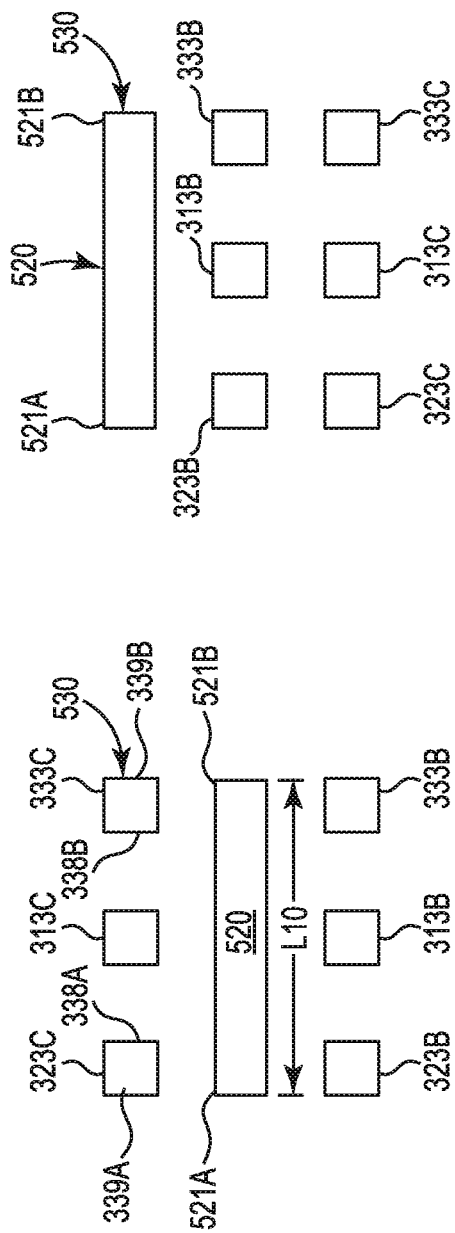

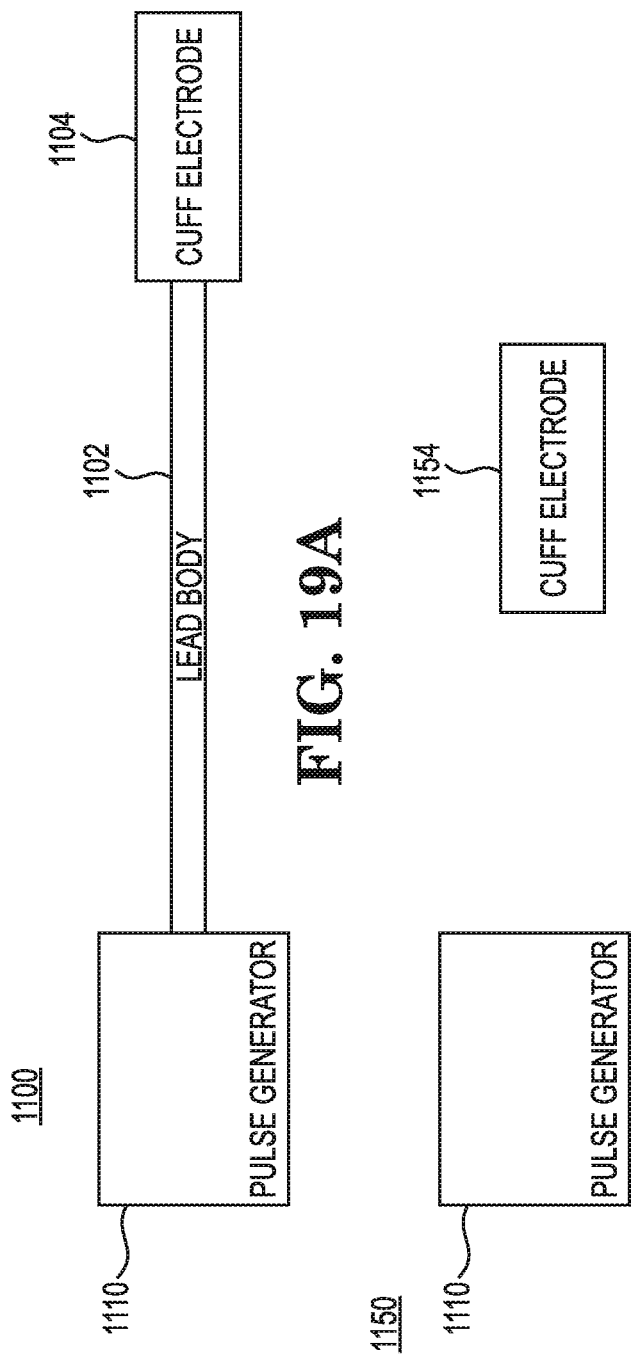
FIG. 19A
FIG. 19B
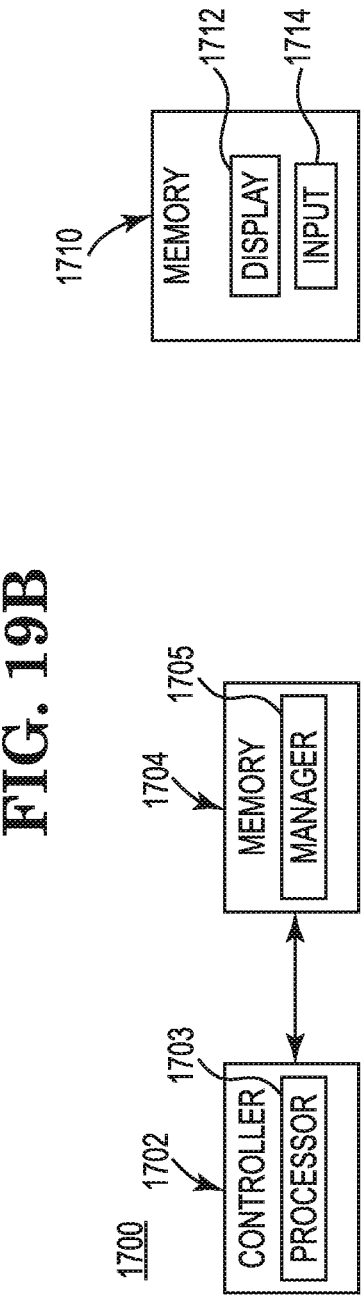
FIG. 20
FIG. 21

2020 — ARRANGING A SECOND ARRAY OF AT LEAST TWO OUTER ELECTRODES AXIALLY ALONG A FIRST ORIENTATION PERPENDICULAR TO THE SECOND ORIENTATION AND ON RESPECTIVELY OPPOSITE ENDS OF THE FIRST ARRAY, WITH EACH RESPECTIVE OUTER ELECTRODE SPACED AXIALLY APART FROM THE FIRST ARRAY

FIG. 22B

2025 — SELECTIVELY STIMULATING AT LEAST THE FIRST NERVE BRANCH WITH TWO ELECTRODES OF THE FIRST ARRAY WHILE GENERALLY EXCLUDING A SECOND NERVE BRANCH FROM STIMULATION

FIG. 22C

2030 — AT LEAST ONE OF NOT ACTIVATING A THIRD ELECTRODE OF THE FIRST ARRAY AND ACTIVATING THE THIRD ELECTRODE OF THE FIRST ARRAY TO SELECTIVELY AT LEAST PARTIALLY HYPERPOLARIZE THE SECOND NERVE BRANCH

FIG. 22D

2035 — SELECTIVELY STIMULATING AT LEAST THE FIRST NERVE BRANCH VIA SELECTIVELY STIMULATING THE FIRST NERVE BRANCH VIA A FIRST ELECTRODE OF THE FIRST ARRAY AND SEPARATELY SELECTIVELY STIMULATING A THIRD NERVE BRANCH VIA AN ADJACENT SECOND ELECTRODE OF THE FIRST ARRAY

FIG. 22E

2040 — ARRANGING THE SECOND ARRAY TO COMPRISE AT LEAST THREE ELECTRODES, INCLUDING THE AT LEAST TWO OUTER ELECTRODES, ARRANGED AXIALLY ALONG THE FIRST ORIENTATION AND FURTHER COMPRISING ARRANGING AN INNER ELECTRODE AXIALLY BETWEEN THE AT LEAST TWO OUTER ELECTRODES

2110 — ARRANGING AT LEAST ONE ARRAY OF FIRST ELECTRODES TO EXTEND AXIALLY ON A CUFF BODY IN A FIRST ORIENTATION ALONG LENGTH OF A NERVE

2120 — ARRANGING A SECOND ARRAY OF SECOND ELECTRODES TO EXTEND CIRCUMFERENTIALLY ON THE CUFF BODY IN A SECOND ORIENTATION GENERALLY PERPENDICULAR TO THE FIRST ORIENTATION

FIG. 22G

2140 — SELECTIVELY STIMULATING AT LEAST A FIRST NERVE BRANCH VIA SELECTIVELY ACTIVATING AT LEAST ONE SECOND ELECTRODE IN COMBINATION WITH SELECTIVE ACTIVATION WITH AT LEAST SOME OF THE FIRST ELECTRODES

FIG. 22H

2150 — ARRANGING THE CUFF BODY TO INCLUDE AN INNER AXIAL PORTION AND TWO OUTER AXIAL PORTIONS ON OPPOSITE ENDS OF THE INNER AXIAL PORTION

FIG. 22I

2155 — ARRANGING THE CUFF BODY SUCH THAT EACH RESPECTIVE AXIAL PORTION INCLUDES AN INNER CIRCUMFERENTIAL PORTION AND TWO OUTER CIRCUMFERENTIAL PORTIONS ON OPPOSITE ENDS OF THE INNER CIRCUMFERENTIAL PORTION

FIG. 22J

2160 — ARRANGING THE OUTER CIRCUMFERENTIAL PORTIONS TO BE SHAPED, AND BIASED FOR RELEASABLE ENGAGEMENT OF THE OUTER CIRCUMFERENTIAL PORTIONS RELATIVE TO EACH OTHER TO DEFINE A RECLOSABLE LUMEN TO ENCIRCLE A NERVE

FIG. 22K

2170 — ARRANGING A RESPECTIVE ONE OF THE FIRST ELECTRODES TO BE IN EACH OF THE RESPECTIVE INNER AND OUTER AXIAL PORTIONS

FIG. 22L

2175 — ARRANGING THE OUTER CIRCUMFERENTIAL PORTIONS OF EACH RESPECTIVE OUTER AXIAL PORTION OF THE CUFF BODY TO BE ELECTRODE-FREE

FIG. 22M

2180 — ARRANGING THE SECOND ELECTRODES TO BE LOCATED IN AT LEAST ONE OF THE RESPECTIVE OUTER CIRCUMFERENTIAL PORTIONS OF THE INNER AXIAL PORTION OF THE CUFF BODY

FIG. 22N

2185 — ARRANGING TWO SECODD ELECTRODES ON ONE OUTER CIRCUMFERENTIAL PORTION OF THE INNER AXIAL PORTION

FIG. 22O

2190 — ARRANGING THE OTHER RESPECTIVE OUTER CIRCUMFERENTIAL PORTION TO BE ELECTRODE-FREE

FIG. 22P

2195 — ARRANGING A STIMULATION SIGNAL VECTOR TO INCLUDE ONE SECOND ELECTRODE IN THE OUTER CIRCUMFERENTIAL PORTION OF THE INNER AXIAL PORTION AND THE OUTER FIRST ELECTRODE IN EACH RESPECTIVE OUTER AXIAL PORTION OF THE CUFF BODY

FIG. 22Q

2200 — ARRANGING AT LEAST THREE SECOND ELECTRODES ON ONE OUTER CIRCUMFERENTIAL PORTION OF THE INNER AXIAL PORTION

FIG. 22R

2210 — ARRANGING THE ONE OUTER CIRCUMFERENTIAL PORTION TO INCLUDE AT LEAST ONE INCREASED THICKNESS PORTION TO HOUSE THE SECOND ELECTRODE(S) AND EXPOSE A PORTION OF THE SECOND ELECTRODE WITHIN THE LUMEN DEFINED BY THE CUFF BODY

FIG. 22S

2220 — ARRANGING THE TWO SECOND ELECTRODES AND AN INNER AXIAL ELECTRODE TO BE EQUALLY SPACED APART CIRCUMFERENTIALLY, IN THE SECOND ORIENTATION, ABOUT THE CONTACT SURFACE OF CUFF BODY

FIG. 22T

2230 — ARRANGING ONE SECOND ELECTRODE TO BE LOCATED ON ONE OUTER CIRCUMFERENTIAL PORTION IN THE INNER AXIAL PORTION OF THE CUFF BODY AND THE OTHER SECOND ELECTRODE ON THE OTHER RESPECTIVE OUTER CIRCUMFERENTIAL PORTION IN THE INNER AXIAL PORTION OF THE CUFF BODY

FIG. 22U

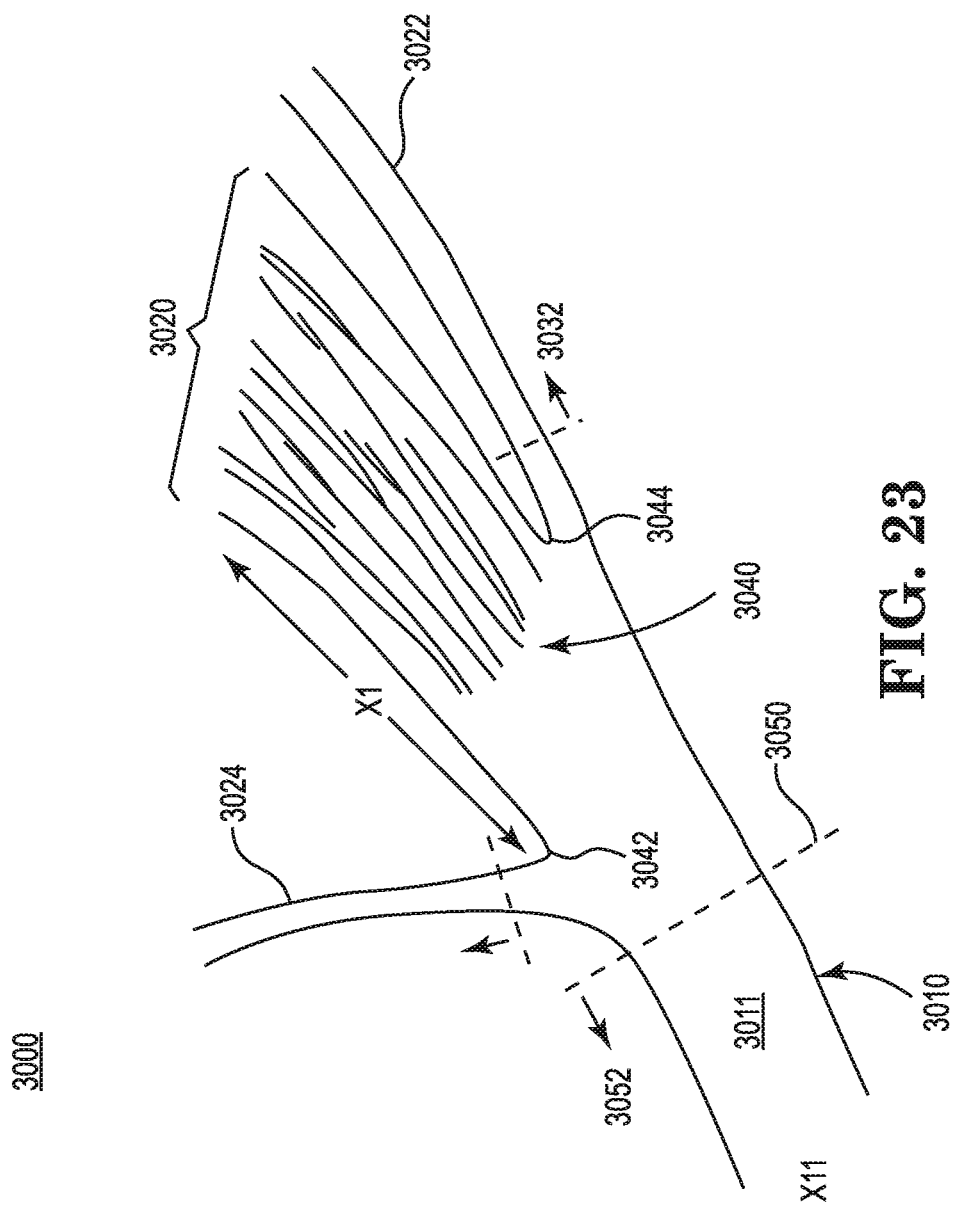

5530 — PERFORMING THE SELECTIVE STIMULATION IN COMBINATION WITH ANOTHER ELECTRODE SUPPORTED BY THE DISTAL EXTENSION AND/OR THE MAIN CUFF BODY

FIG. 28B

5535 — UTILIZING AT LEAST SOME ELECTRODES OF A MAIN CUFF BODY TO STIMULATE A MAIN NERVE IN A COMPLEMENTARY MANNER WITH STIMULATING A PARTICULAR NERVE BRANCH VIA AT LEAST ONE OF THE ELECTRODES OF THE DISTAL EXTENSION

FIG. 28C

5540 — ARRANGING THE DISTAL EXTENSION TO BE AT LEAST PARTIALLY SELF-WRAPPABLE ABOUT THE FIRST NERVE BRANCH WITHOUT ENCIRCLING THE MAIN NERVE

FIG. 28D

5550 — ARRANGING THE DISTAL EXTENSION TO EXTEND ALONG A PORTION OF THE FIRST NERVE BRANCH WITHOUT AT LEAST PARTIALLY WRAPPING ABOUT THE FIRST NERVE BRANCH

FIG. 28E

CUFF ELECTRODE

CROSS-REFERENCE TO RELATED APPLICATIONS

This 35 U.S.C. § 371 National Phase application claims priority to International Application No. PCT/US18/46100, filed Aug. 9, 2018, which claims the benefit of U.S. Provisional Patent Application No. 62/544,140, filed Aug. 11, 2017; which are both incorporated herein by reference in their entirety.

BACKGROUND

Treating sleep disordered breathing has led to improved sleep quality for some patients.

BRIEF DESCRIPTION OF THE DRAWINGS

FIG. 2 is a sectional view schematically representing the example cuff electrode of FIG. 1 as taken along lines 2-2.

FIG. 3 is a sectional view schematically representing the example cuff electrode FIG. 1 as taken along lines 3-3.

FIG. 4 is a diagram including an isometric view schematically representing different portions of an example cuff electrode.

FIG. 5A is a diagram including an isometric view schematically representing an example device including different portions of a cuff body and an electrode pattern of the cuff electrode of FIG. 4.

FIG. 5B is a diagram including a sectional view schematically representing relative arc lengths of circumferential portions of an example cuff body.

FIGS. 7A-7K is a series of diagrams, each schematically representing different example electrical stimulation vectors and/or example methods.

FIG. 8A is an isometric view schematically representing an example cuff electrode.

FIG. 8B is a diagram schematically representing an example electrode pattern of the cuff electrode of FIG. 8A.

FIG. 9 is a sectional view schematically representing the example cuff electrode of FIG. 8A, as taken along lines 9-9.

FIG. 12 is an isometric view schematically representing an example cuff electrode.

FIG. 13A is a diagram schematically representing an example electrode pattern of the cuff electrode of FIG. 12.

FIG. 13B is a diagram schematically representing an example electrode pattern of the cuff electrode of FIG. 12.

FIG. 19A is block diagram schematically representing an example fully implantable neurostimulation system including a pulse generator, lead, and cuff electrode.

FIG. 19B is block diagram schematically representing an example neurostimulation system including a pulse generator and leadless cuff electrode.

FIG. 20 is a block diagram schematically representing an example control portion.

FIG. 21 is a block diagram schematically representing an example user interface.

FIGS. 22A-22U are each a flow diagram, or a portion of a flow diagram, schematically representing an example method.

FIG. 23 is a diagram schematically representing an example nerve branch configuration at which an example cuff electrode may be mounted.

FIGS. 28A-28E are each a flow diagram, or a portion of a flow diagram, schematically representing an example method.

DETAILED DESCRIPTION

Figure 1:
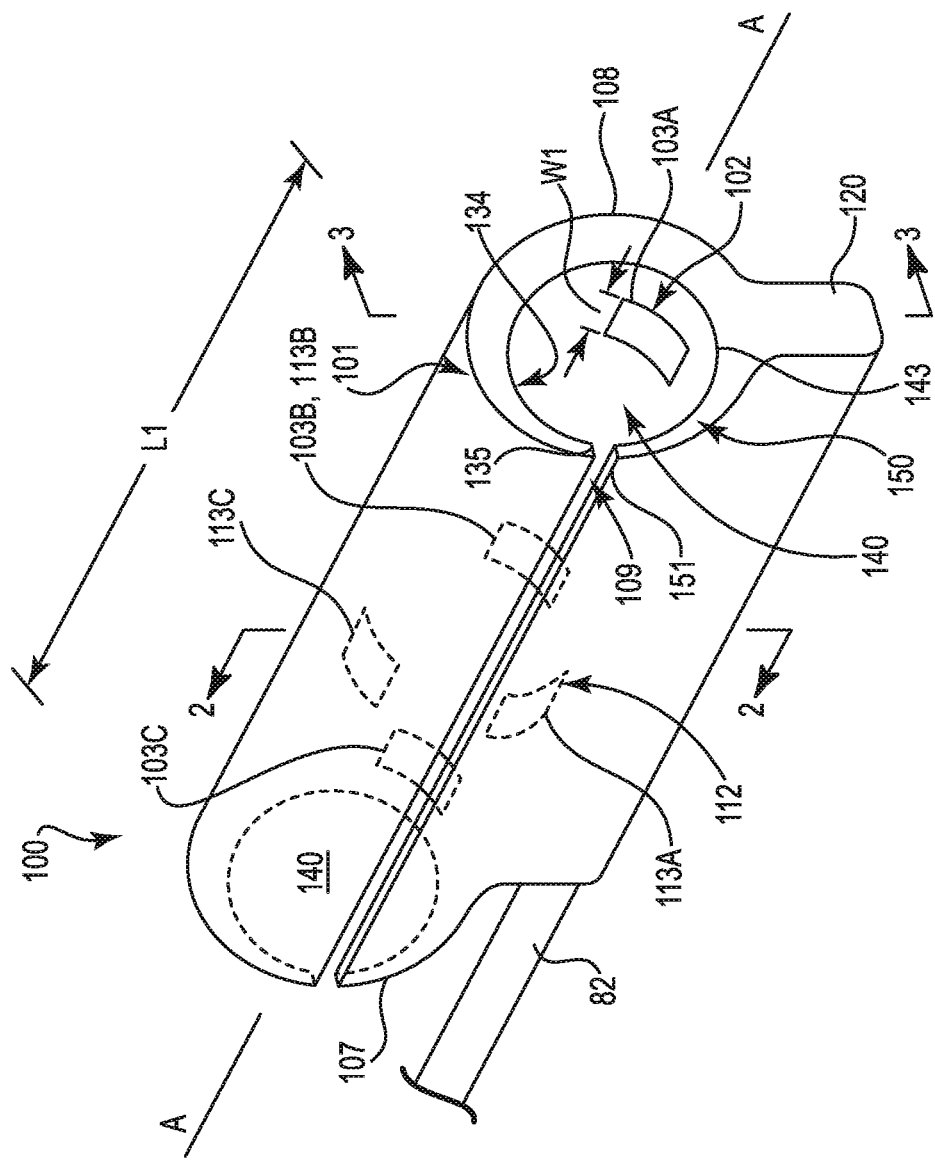
FIG. 1 is an isometric view schematically representing an example cuff electrode.

In the following Detailed Description, reference is made to the accompanying drawings which form a part hereof, and in which is shown by way of illustration specific examples of the present disclosure which may be practiced. In this regard, directional terminology, such as "top," "bottom," "front," "back," "leading," "trailing," etc., may be used with reference to the orientation of the Figure(s) being described. Because components of at least some examples of the present disclosure can be positioned in a number of different orientations, the directional terminology is used for purposes of illustration and is in no way limiting. It is to be understood that other examples may be utilized and structural or logical changes may be made without departing from the scope of the present disclosure. The following detailed description, therefore, is not to be taken in a limiting sense.

In at least some examples, a cuff electrode includes an electrode array suited to selective stimulation profiles which may enhance electrical stimulation of a nerve. In some examples, the nerve comprises an airway-patency-related nerve to treat sleep disordered breathing behavior. In some examples, the airway-patency-related nerve comprises a nerve which innervates a tongue muscle. In some examples, the nerve comprises the hypoglossal nerve. Accordingly, in at least some instances, the airway-patency-related nerve may sometimes be referred to as an upper-airway-patency-related nerve.

In some examples, the cuff electrode comprises a cuff body supporting at least one array of first electrodes extending axially along a length of the cuff body in a first orientation. In some examples, the cuff electrode includes at least one array of second electrodes extending in a second orientation generally perpendicular to the first orientation. The second orientation may sometimes be referred to as a circumferential orientation while the first orientation may sometimes be referred to as an axial orientation. In some examples, one of the first electrodes of the axially-extending array functions as one of the second electrodes of the circumferentially-extending array.

In some examples, other than the array of axially-extending first electrodes, the cuff electrode omits any other electrodes (or other electrically conductive materials) in the portions of the cuff body which extend proximally and extend distally relative to the array of circumferentially-extending second electrodes. Via this arrangement, such electrically-conductive-free portions of the cuff body may act as electrical insulative portions to minimize stimulation toward non-targeted nerve branches and surrounding non-nerve tissues. In addition, as part of the overall cuff body, these electrically-conductive-free portions act to mechanically secure the electrodes relative to the nerve. Moreover, via this arrangement, the cuff body retains high flexibility in its distal and proximal portions, thereby contributing to maneuverability of the cuff electrode during implantation.

In various other examples, a cuff electrode comprises additional electrodes and/or electrode arrays to provide more combinations of selectable electrodes.

These examples, and additional examples, are described in more detail in association with at least FIGS. 1-29B.

FIG. 1 is an isometric view schematically representing a cuff electrode 100, according to one example of the present disclosure. As shown in FIG. 1, the cuff electrode 100 comprises a cuff body 101 including a first arm 134 and a second arm 150, which together form a re-closable lumen 140. In some examples, an end 135 of the first arm 134 and an end 151 of the second arm 150 are releasably engageable relative to each other to at least partially define the re-closable lumen 140. It will be understood that in some examples, the point of releasable engagement 109 may be located at other positions about the circumference of the re-closable lumen 140, with the respective arms 134, 150 having different relative lengths (than shown in FIG. 1) to implement the particular location of releasable engagement of the ends of the respective arms 134, 150. It will be understood that for illustrative clarity FIG. 1 depicts a small gap at the point of releasable engagement 109, even though in at least some examples the ends 135, 151 may be touching each other.

In some examples, cuff body 101 comprises a third arm 160 which overlaps second arm 150 and first arm 134, as further described later in association with at least FIG. 2.

As shown in FIG. 1, in some examples, cuff electrode 100 comprises a first array 102 of spaced apart electrodes 103A, 103B, 103C extending axially along a length of the cuff body 101 and a second array 112 of electrodes 113A-113C, which extends circumferentially about a nerve-contact surface 143 of lumen 140. In some examples, the electrodes 103A, 103B, 103C of the example first array 102 may sometimes be referred to as first electrodes. In some examples, the electrodes 113A, 113B, 113C of the example second array 112 may sometimes be referred to as second electrodes.

In some examples, the electrodes 113A, 113B, 113C extend in the same cross-sectional plane (e.g. a single cross-sectional plane), as further shown later in at least FIGS. 2, 5B, 6A, etc. The respective electrodes 103A-103C, 113A-113C are at least partially exposed on nerve-contact surface 143 of lumen 140, such as shown in FIG. 1 and later shown in at least FIGS. 6A-6B and/or FIG. 9. In some examples, electrode 103B of first array 102 functions as (i.e. is the same physical element) electrode 113B in the second array 112. In some examples, the various electrodes have generally the same size and/or shape. In some examples, at least some of various electrodes may be differently sized and/or differently shaped than other electrodes.

In some examples, electrode 113A is supported on second arm 150 while electrode 113C is supported on first arm 134 while electrodes 103A-103C are supported on a proximal portion of first arm 134 and/or a top portion of base 120. The base 120 supports and/or at least partially defines a junction of the proximal portions of the respective first and second arms 134, 150. While not shown for illustrative clarity, base 120 may house electrically conductive elements which extend from lead 82 and at least partially through a length (e.g. L1) of the base 120 for connection to electrodes 103A-103C, 113A-113C. In some instances, base 120 also may sometimes be referred to as a spine.

In some examples, an electrode of the cuff electrode 100 may sometimes be referred to as an electrode contact because each electrode includes an electrically conductive contact surface intended to engage tissue, such as an outer surface of a nerve, through which electrical stimulation is to be applied.

Accordingly, with reference to at least FIG. 1, in some examples the inner electrodes 113A, 113B (103B), 113C of the circumferentially-oriented array 112 comprises three independently programmable electrodes while the outer electrodes 103A, 103C are electrically common with each other, such that the cuff electrode 100 has four independently programmable functional electrodes. In some examples, via this arrangement the outer electrodes 103A, 103C may be operated as anodes such that cuff electrode 100 provides a guarded cathode arrangement with the inner axial electrodes 113A, 113B (103B), 113C selectively operable as cathodes.

In some examples, the three axially arranged electrodes (e.g. electrode 103A, electrode 103C, and at least one of 113A, 113B, 113C electrodes) may implement a guarded bipolar configuration in which positive electrodes on the ends of the cuff hyperpolarize the nerve to prevent stimulation of non-target tissues. In some examples, the reference to positive electrodes and negative electrodes may refer to the first phase of biphasic stimulation, e.g. the phase of stimulation intended to depolarize the target nerve.

In some examples, having three inner electrodes 113A, 113B, 113C which are equally spaced apart in a circumferential orientation may enhance selective stimulation of particular targeted and non-targeted branches of a nerve bundle. For instance, via such selective stimulation one may exclude (e.g. non-target) one of the branches of a target nerve (e.g. hypoglossal nerve). For instance, it may be beneficial in some examples to not stimulate a branch of the hypoglossal nerve, which would cause retraction of the tongue, with such nerve branches being referred to herein as a retractor nerve branch.

For example, supposing just two circumferentially oriented electrodes were equally spaced apart (e.g. 180 degrees apart) and a non-target branch were located at 90 degree angle relative to each of the respective pair of electrodes, then it may sometimes be difficult to apply a signal with sufficient strength to capture the target nerve branches to achieve the desired muscle response (e.g. tongue protrusion) while still excluding the non-target nerve branches (e.g. tongue retractors).

For example, in some instances a retractor nerve branch may split off from the main nerve bundle early such that the retractor nerve is external to the remaining nerve bundle at the point at which the cuff body/electrode 100 is releasably engaged about the main nerve bundle. In some instances a retractor nerve branch remains within the main nerve bundle but is in close proximity to one of the inner electrodes 113A, 113B, 113C such that non-activation of the particular electrode 113A, 113B, 113C closest to the retractor nerve branch may serve to exclude the retractor nerve branch from stimulation, while activation of the remaining two electrodes (of the three electrodes 113A, 113B, 113C) are sufficient to depolarize the protrusor-related branches of the main nerve bundle.

In some examples, in some instances in which a targeted nerve branch may be located at an intermediate position between two of the circumferentially spaced apart electrodes, an adequate depolarization of the target nerve branch may be implemented via applying a high strength signal at one electrode. In some examples, application of a low or moderate strength signal at the remaining two electrodes may contribute to depolarization of the target nerve branches, as desired. Accordingly, regardless of the particular position of the main target nerve branches within the main nerve bundle, the availability of three electrodes 113A, 113B, 113C (which are equally spaced in the circumferential orientation) may ensure some combination of activation of at least some of such electrodes to achieve adequate depolarization of target nerve branches.

In some such examples, as noted above and throughout examples of the present disclosure, such an electrode configuration may also serve to exclude non-target nerve branches from stimulation in some instances. Moreover, in some examples, via at least some of the electrodes 113A, 113B, 113C, hyperpolarization may be implemented to inhibit stimulation of some nerve branches (e.g. retractor nerve branches) or other nerve branches exhibiting a negative response.

In some examples, cuff electrode 100 may be implemented having at least some of substantially the same features and attributes as one of the cuff electrodes described in Bonde et al. U.S. Pat. No. 9,227,053, "Self-Expanding Electrode Cuff", issued on Jan. 5, 2016, and/or in Bonde et al. U.S. Pat. No. 8,340,785, "Self-Expanding Electrode Cuff", issued on Dec. 25, 2012, both of which are herein incorporated by reference.

In some examples, the array of first electrodes 103A, 103B, 103C and the array of second electrodes 113A, 113B (same as 103B), 113C together exclusively define all the electrodes supported on the cuff body. In some examples, the array of first electrodes 103A, 103B, 103C and the array of second electrodes 113A, 113B (same as 103B), 113C together exclusively define all the electrodes supported on an implantable medical device, which includes the cuff body. In some examples, this implantable medical device includes a cuff electrode and an implantable pulse generator. In some examples, this implantable medical device includes a cuff electrode, an implantable pulse generator, and lead extending between the cuff electrode and implantable pulse generator. In some examples, this implantable medical device includes a cuff electrode, an implantable pulse generator, a lead extending between the cuff electrode and implantable pulse generator, and a separate respiration sensor/lead.

FIG. 2 is a sectional view schematically representing the cuff electrode of FIG. 1 as taken along lines 2-2, according to one example of the present disclosure. In some examples, the cuff electrode 100 in FIG. 2 comprises at least some of substantially the same features and attributes as cuff electrode 100 in FIG. 1, except for further depicting the third arm 160 in addition to the respective first and second arms 134, 150. As shown in FIG. 2, the distal portion 137 of the first arm 134 is bendable (per directional arrow B) and the second arm 150 is bendable (per directional arrow D) to open cuff body 101 to enclose a nerve within lumen 140. In addition, in FIG. 2 the third arm 160 is shown in an already-bent position (per directional arrow E) to permit access to lumen 140 and to permit selective movement of the first and second arms 134, 150. It will be understood that, after manipulation to open the cuff electrode 100 for mounting a nerve, each of the respective arms 134, 150, 160 are biased to return to their "closed" position forming the re-closable lumen 140.

As shown in FIG. 2 and as further described in association with at least FIGS. 4-5B, in some examples the cuff body 101 may be understood as having different portions with boundaries between the respective portions represented via dashed lines. It will be understood that in at least some examples the dashed lines shown in the Figures do not represent actual seams or discontinuities in the cuff body. It will be further understood that other conventions for allocating different portions of cuff body 101 may be adopted.

For instance, in some examples the cuff body 101 may be viewed as having different portions along a circumferential orientation (line C), which is generally perpendicular to an axial orientation (line A in FIGS. 1, 3) of the cuff body 101. In some examples, the cuff body 101 may be viewed as having an inner circumferential (IC) portion 182 and two outer circumferential portions 184A, 184B with the respective portions 182, 184A, 184B extending throughout the entire length of the cuff body 101. Boundaries between the respective inner circumferential (IC) portion 182 and the outer circumferential (OC) portions 184A, 184B are represented via dashed lines 187A, 187B. The inner circumferential and outer circumferential designations will be further described in association with at least FIGS. 5A-5B.

In some examples, the inner circumferential portion 182 corresponds to a location of the nerve-contact surface 143 at which the electrodes 103A, 103B, 103C are located. In one aspect, the inner circumferential portion 182 provides for the electrode 113B (i.e. 103B) to have an intermediate position relative to the respective outer electrodes 113A, 113C.

FIG. 3 is a sectional view schematically representing a cuff electrode as taken along lines 3-3 of FIG. 1, according to one example of the present disclosure. As shown in FIG. 3, in some examples the cuff body 101 may be viewed as having different portions extending along an axial orientation, which is generally parallel to a longitudinal axis (line A in FIG. 1) of the cuff body 101. In some examples, the different portions may be referred to as an inner axial portion 202 and two outer axial portions 204A, 204B with each axial portion including one of the electrodes 103A, 103B, 103C. As further shown at least partially in FIG. 3, the inner axial portion 202 also includes the electrodes 113A, 113B, 113C of the second array 112.

As further shown in FIG. 3, in some examples an electrically conductive element 170 extends through a length of a base 120 of the cuff body 101 and is electrically coupled relative to each of the respective electrodes 103A, 103B, 103C. In some examples, the electrically conductive element 170 may take the form of coil, and includes several electrically independent conductive strands 171 such that each electrode 103A, 103B, 103C is independently programmable/controllable.

While not shown in FIG. 3 for illustrative simplicity, it will be understood that in some examples additional electrically independent conductive elements (e.g. wires) extend from a portion of the electrically conductive element 170 and are electrically connected to the electrodes 113A, 113B 113C of the second array 112 in the inner axial portion 202 of the cuff body 101 such that each electrode 113A, 113B (same as 103B), 113C is also independently programmable/controllable.

In some examples, the additional electrically independent conductive elements may promote flexibility of the overall cuff structure and may withstand expected flexing of the cuff body. In some such examples, the additional electrically independent conductive elements extending through at least a portion of the cuff body may comprise at least some undulating portions and/or otherwise designed to flex.

However, in at least some examples, the "additional" electrically independent conductive elements extend circumferentially within the inner axial portion 202 of the cuff body 101. Moreover, in some examples these "additional" electrically independent conductive elements do not extend circumferentially within the outer axial portions 204A, 204B of the cuff body 101, as further described later in association with at least FIGS. 4, 5A-5B.

FIGS. 4-5A provide further illustrations of the respective different portions of cuff body 101. FIG. 4 is a diagram including an isometric view schematically representing different portions of a cuff electrode 200 including a cuff body 201, according to one example of the present disclosure. Portions of the cuff body 201 are akin to the cuff body 101 (FIG. 2). In one aspect, the diagram in FIG. 4 expands on designations associated with the schematic representation of the inner and outer circumferential portions 184A, 184B in FIG. 2 and of the inner and outer axial portions in the sectional view of FIG. 3. In some examples, the point of releasable engagement 109 is used as a reference point to define a boundary between at least some of the different portions of the cuff body 101, 201. However, in some examples other reference points may be used.

FIG. 5A is a plan view schematically representing a nerve-contact surface of the cuff electrode 200 of FIG. 4 with the cuff body 201 fully opened and laid out flat for illustrative purposes.

FIG. 5A depicts different portions of the cuff body 101 with portions 252A, 252B, 252C corresponding to a first outer axial (OA) portion 204A and with portions 254A, 254B, 254C corresponding to a second outer axial (OA) portion 204B. Moreover, portions 250A, 250B, 250C in FIG. 5A correspond to inner axial (IA) portion 202. Meanwhile, portions 252B, 250B, 254B in FIGS. 4-5A correspond to inner circumferential (IC) portion 182 in FIG. 2. Portions 252A, 250A, 254A in FIGS. 4-5A correspond to a first outer circumferential (OC) portion 184A and portions 252C, 250C, 254C in FIGS. 4-5A correspond to a second outer circumferential (OC) portion 1848. With this in mind, in viewing FIG. 5A it can be seen that any given portion (e.g. 252C) includes both an axial and circumferential designation (e.g. OA and OC).

In some examples, the outer axial portions (e.g. 252A, 252C, 254A, 254C) omit any electrically conductive elements, such as electrodes and/or electrically conductive elements (e.g. wires) extending to/from an electrode in a different portion of the cuff body 201. Stated differently, any wires which extend in or through the inner axial, outer circumferential portions 250A, 250C of the cuff body 101, 201 do not pass through the outer axial, outer circumferential portions 252A, 252C, 254C, 254C of the cuff body 101, 201. In other words, the outer axial, outer circumferential portions of the cuff body 101, 201 are free from any electrically conductive elements (e.g. wires, traces, etc.). In this way, these respective portions (e.g. 252A, 252C, 254A, 254C) act as electrically insulative portions, which in some examples, may contribute to selective stimulation of a target nerve portion by minimizing inadvertent stimulation of non-targeted surrounding tissues.

In addition, the omission of electrodes and/or conductive elements (e.g. wires) in the proximal outer axial portions 252A, 252C and the distal outer axial portions 254A, 254C of the cuff electrode 100 may enhance flexibility of the respective distal and proximal ends of the cuff body 101. In some examples, this enhanced flexibility may permit easier placement of the cuff electrode 100 relative to the nerve and/or may enhance gentler contact with the nerve. In some examples, the effect of these flexibility enhancements may be greater when the cuff electrode 101 is placed on more distal portions of the target nerve, such as a hypoglossal nerve. In some such examples, the proximal outer axial portions (e.g. 252A, 252C) and the distal outer axial portions (e.g. 254A, 254C) may sometimes be referred to as being more flexible than inner axial portion (e.g. 250A, 250B, 250C) and/or may sometimes be referred to as being electrically-conductive-free portions. In some such examples, the proximal outer axial portions (e.g. 252A, 252C) and the distal outer axial portions (e.g. 254A, 254C) are substantially more flexible, such as 25%, 50%, 75% more flexible, than the inner axial portions (e.g. 252A, 252C). In some such examples, the term substantially more flexible may correspond to being 2×, 3×, 4× more flexible.

While the cuff body 101 is made of a polymeric material which is generally electrically non-conductive, in some examples, the proximal outer axial portion 252C and distal outer axial portion 254C further includes additive electrically insulative material to further protect non-targeted surrounding tissues from unintended stimulation.

By providing this arrangement of just a single array of circumferentially-oriented electrodes 113A, 113B, 113C (in addition to the axially-oriented array of first electrodes 103A-103C) instead of a fully cylindrical array (e.g. 3×3, 4×4, etc.), fewer wires extend through/within the lead body 82 up to and through the length of the cuff body 101, which in turn provides for a highly flexible lead suited to the highly mobile neck structure. By providing a lead body 82 with relatively high flexibility as it extends through/within the neck region (upon implantation), patient comfort and longevity of the lead body 82 may be enhanced because the lead body 82 is able to flex well with the many different positions and frequency of movement of the neck region.

In some examples, as shown in at least FIG. 3, D5 represents the axial length of the electrically-conductive-free portions (e.g. 252C, 254C, etc.) of cuff body from the inner axial, circumferentially-oriented electrodes 113A, 113B, 113C to an end 107 of the cuff body 101. In some examples, this axial length (D5) is substantially greater than a width (W1) of the electrodes 113A, 113B, 113C. In some examples, the axial length D5 is at least 3 times the width W1. In some examples, the axial length D5 is at least 4 times the width W1.

In addition, once the cuff electrode 100 is implanted at a desired location along a length of the target nerve (e.g. hypoglossal nerve), in some examples the opposite ends 107, 108 of the cuff body 101, 201 may sometimes lie in close proximity to other nerve branches extending off the target nerve. By omitting additional electrodes in the proximal outer axial portion (252A, 252C) and the distal outer axial portion (254A, 254C) of the cuff body 201, selective stimulation may be confined primarily in an area interior to the opposite ends 107, 108 of the cuff body 201, which in turn may minimize incidental stimulation of the non-target nerve branches and/or other surrounding non-nerve tissues.

As further shown in FIG. 5A, the various different portions of cuff body 201 are depicted as having a generally uniform width (W2, W3, W4) and generally uniform length (L2, L3, L4). However, in some examples the widths and/or lengths of the various different portions may be non-uniform, such that W3 is greater than W2, W4 is greater than W2, etc. as some non-limiting examples. Moreover, while FIG. 4 depicts the thickness of the wall of the cuff body 101 as having a generally uniform thickness for illustrative simplicity, it will be understood that the thickness of a given portion (e.g. 252A) may vary along its length and/or width in some examples and that thickness of one portion (e.g. 252A) need not necessarily match a thickness of another portion (e.g. 254C).

As shown in the sectional view of FIG. 5B, in some examples, according to the circumferential orientation the three respective outer and inner circumferential portions 184A, 184B, 182 have generally equal arc lengths (AL1, AL2, AL3), such that each extends about 120 degrees arc of a 360 degree circumference. It will be understood that the reference numerals AL1, AL2, AL3 in FIG. 5B correspond to the designators W2, W3, W4 in FIG. 5A. In some examples, the inner circumferential portion 182 extends less than a 120 degree arc, such as a 100 degree arc. In some examples, a first outer circumferential portion 184A (e.g. OC portions 252A, 250A, 254A) has a circumferential arc length (AL1; W2) that is substantially the same as a circumferential arc length (AL3; W4) of the second outer circumferential portion 184B (e.g. OC portions 252C, 250C, 254C).

However, in some examples, the first outer circumferential portion 184A (e.g. OC portions 252A, 250A, 254A) has a circumferential arc length (AL1; W2) that is different from the circumferential arc length (AL3; W4) of the second outer circumferential portion 184B (e.g. OC portions 252C, 250C, 254C). In some examples, the first outer circumferential portion 184A (e.g. OC portions 252A, 250A, 254A) has a circumferential arc length (AL1; W2) that is substantially less than a circumferential arc length (AL3; W4) of the second outer circumferential portion 184B (e.g. OC portions 252C, 250C, 254C) as shown in FIG. 4.

In some examples associated with at least FIGS. 1-5B, a size and/or shape of each of the inner axial portion 202 (portions 250A, 250B, 250C) of the cuff body 201 may be at least partially characterized by having no more than one electrode (e.g. 113A, 113B (also known as 103B), 113C) and a size and/or shape of each portion 252B, 254B (inner circumferential IC, outer axial OA) of the cuff body 201 may be characterized as having no more than one electrode (e.g. 103A, 103C, respectively).

However, as later described in association with at least FIGS. 14A, 14B, 18A, 18B, in some examples a portion 250A (outer circumferential OC, inner axial IA) of the cuff body 201 omits an electrode (e.g. 113A) while a portion 250C (outer circumferential OC, inner axial IA) of the cuff body 201 includes two electrodes (e.g. 113A, 113C).

While cuff electrode 100 is shown in FIG. 1 as extending from a lead body 82, it will be understood that in some examples the cuff electrode 100 may comprise a leadless cuff electrode 1100, as later shown in FIG. 19B. Accordingly, in some examples, the leadless cuff electrode 1100 may comprise an antenna and/or circuitry for wirelessly communicating with a control portion (FIG. 20) and/or a pulse generator 1110 located external to the patient's body (FIG. 19B) and/or located elsewhere in the patient's body (FIG. 19A). In some examples, the antenna and/or circuitry is housed within the base 120 of the cuff body of cuff electrode 1100.

Accordingly, with reference to at least FIGS. 1-5B, in some examples the inner electrodes 113A, 113B (103B), 113C of the circumferentially-oriented array comprises three independently programmable electrodes while the outer electrodes 103A, 103C are electrically common with each other, such that the cuff electrode 100, 200 has four independently programmable functional electrodes. In some examples, via this arrangement the outer electrodes 103A, 103C may be operated as anodes such that cuff electrode 100 provides a guarded cathode arrangement with the inner axial electrodes 113A, 113B (103B), 113C selectively operable as cathodes.

In some examples, as later shown in FIG. 19A-19B, the cuff electrode 100, 200 is associated with an implantable pulse generator (IPG) 1110 having an external conductive case, which may selectively act as an electrode in cooperation with the functional electrodes of cuff electrode 100.

Via the arrangement of the axial array of electrodes 103A, 103C, and the circumferentially-oriented array of electrodes 113A, 113B (same as 103B), 113C of cuff electrode 100, effective selective stimulation may be achieved without unduly complicating the associated programming to do so. Moreover, a high degree of selectivity in stimulating various nerve fiber groups may be achieved with a relatively small number of electrodes.

In some examples, the particular arrangement of electrodes 113A-113C, 103A-103C depicted in at least FIGS. 1-5B may be implemented in a cuff body having a different configuration of arms than the particular arrangement of arms of cuff body 101, 201 shown in FIGS. 1-5B.

Figure 6A:
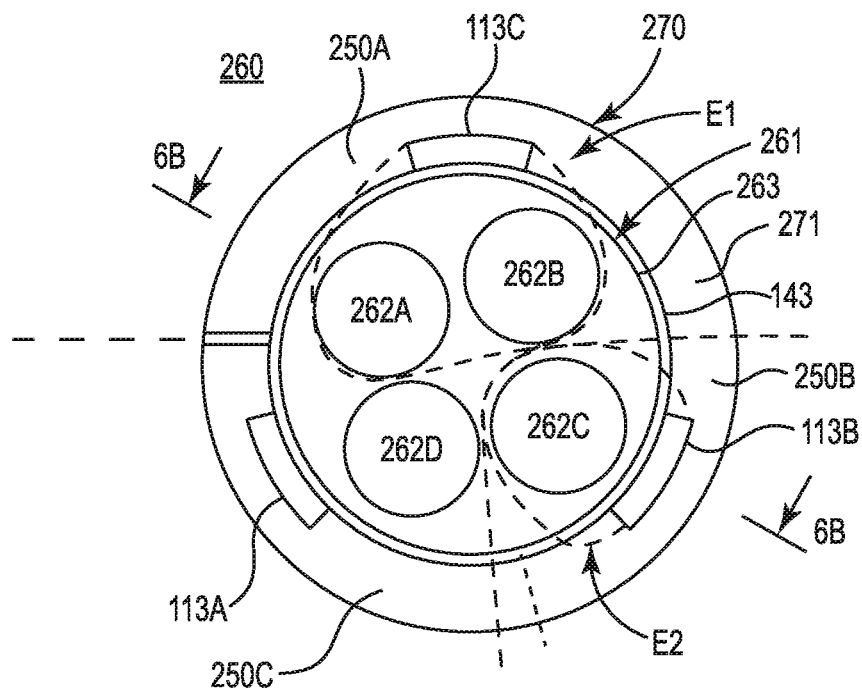
FIG. 6A is a diagram including a sectional view schematically representing an example cuff electrode relative to nerve groups within a nerve.

FIG. 6A is a sectional view schematically representing a cuff electrode 270 engaged about a nerve 261, according to one example of the present disclosure. In at least some examples, FIG. 6A also may be viewed as schematically representing a method of neurostimulation and/or therapy to treat sleep disordered breathing, such as but not limited to obstructive sleep apnea. In some examples, cuff electrode 270 comprises at least some of substantially the same features and attributes of cuff electrodes 100, 200 as described in association with at least FIGS. 1-5B. This sectional view generally corresponds to the sectional view of FIG. 2 as taken through inner axial portions 250A, 250B, 250C of cuff body 101, 201. Among other features, FIG. 6A illustrates that, in at least some examples, the circumferentially-oriented array of electrodes 113A, 113B, 113C are equally spaced apart about circumference of nerve-contact surface 143 of cuff body 101, 271. It will be understood that a nerve-contact surface 143 of cuff electrode 270 is in releasable contact against an outer surface 263 of nerve 261 with FIG. 6A and that the minor spacing shown between the nerve-contact surface 143 and outer surface 263 of nerve 261 are provided for illustrative clarity.

Figure 6B:
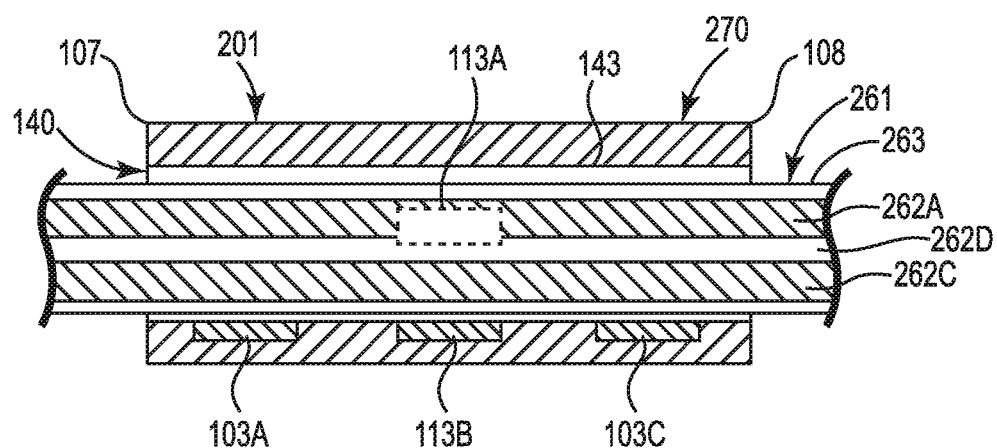
FIG. 6B is diagram including a sectional view as taken along lines 6B-6B of FIG. 6A and schematically representing an electrode array of an example cuff electrode.

As shown in FIG. 6A, the nerve 261 comprises several nerve fiber groups 262A-262D, with the exact number (e.g. 3, 4) of nerve fiber groups varying from nerve-to-nerve and dependent on a location along the nerve. In some instances, more nerve fiber groups are present in more proximal portions of a nerve and fewer nerve fiber groups are present in more distal portions of a nerve pathway. In general terms, the nerve fiber groups 262A-262D may be considered as being arranged in a generally circumferential pattern. However, the depiction in FIGS. 6A-6B provides just one example pattern with it being further understood that the various nerve fiber groups may have different diameters from each other and/or may have positions within the nerve casing which vary from the positions shown in FIG. 6A.

In attempting to electrically stimulate the nerve 261 as a whole, each of the nerve fiber groups may exhibit different responses than each other. In some examples, the different responses may be characterized as a non-response, a positive response, or a negative response. A wide variety of factors may influence the degree to which a particular nerve branch responds to electrical stimulation. In some examples, a non-response of a nerve group to electrical stimulation may be caused by a lack of physical contact between an electrode and the nerve or caused by a fluid presence between the electrode and the nerve. In some examples, a non-response also may be caused by a temporary neurapraxia, in which normal nerve conduction fails for some period of time. In some examples, a non-response may be caused by prior permanent damage to the nerve bundle or the nerve as a whole. In some examples, other factors affecting a non-response may comprise nerve diameter and/or relative degree of myelination. In some examples, some combination of these factors and/or other factors may cause a non-response of a nerve fiber group(s) to electrical stimulation.

In some examples, a negative response (to electrical stimulation of the nerve via a cuff electrode) may be characterized as a response in which some behavior detracts from the intended response. For instance, in some examples, a negative response may be characterized as an uncomfortable muscle response, such as an uncomfortable motion of a tongue muscle, and/or abrasion on teeth adjacent to the stimulated tongue muscle. In some examples, a negative response may be characterized as an undesirable tongue motion, such as retraction of the tongue when a tongue protrusion was the intended response.

In some examples, a positive response may be characterized by muscle contraction of a muscle innervated by a target nerve to which stimulation was intentionally applied via the cuff electrode. In some examples, a positive response may be characterized by at least one muscle causing protrusion of the tongue to maintain or restore airway patency upon electrical stimulation of an upper airway patency-related nerve (e.g. hypoglossal nerve) via a particular stimulation vector(s) via one or more electrode combinations of the cuff electrode.

When observing a response to determine whether it is a positive response, a negative response, or a non-response, in at least some examples the primary response is observed near a cathode of a cuff electrode and a non-response observed near an anode of the cuff electrode. In some examples, such as a guarded cathode configuration, the cathode corresponds to one of electrodes 113A, 113B (same as 103B), and/or 113C while the anode corresponds to electrodes 103A, 103C.

Via the circumferentially arranged electrodes 113A, 113B (same as 103B), 113C, the various nerve groups may be selectively stimulated to recruit nerve fiber groups which exhibit a positive response and avoid recruitment of nerve fiber groups which exhibit negative responses or a non-response.

In doing so, in some examples the targeting of stimulation to induce positive responses may be implemented via selective stimulation. However, in some examples, the targeting of stimulation may be implemented via selective hyperpolarization which may act to suppress negative responses of some nerve fiber groups. In some examples, a combination of selective stimulation and selective hyperpolarization may be implemented to result in the desired recruitment of and/or inhibiting of particular nerve fiber groups.

In some examples, the path of stimulation may be implemented as a short stimulation path or as a long stimulation path based on the position of the electrodes of the cuff electrode which being employed as anodes. In some examples, a short stimulation path may provide for better isolation of nerve fiber groups within a nerve. Stated differently, a short stimulation path may permit more precise targeting of particular nerve fiber groups. In some examples, a short stimulation path may be implemented via using at least some inner electrodes as the anode(s). For instance, in some examples, a short stimulation path may include one or more of the inner axial electrodes 113A, 113B, 113C as a cathode and at least one of the inner axial electrodes 113A, 113B, 113C as an anode. The later described FIGS. 7G-7H and FIGS. 7I-7K provide some examples of a short stimulation path.

In some examples, a long stimulation path may permit an increased response level in the targeted nerve fiber groups for a given energy level delivered to the nerve. In some examples, a long stimulation path may include the outer axial electrodes 103A, 103C as anodes and one of the inner axial electrodes 113A, 113B (same as 103B), 113C as a cathode. The later described FIGS. 7C-7D and FIGS. 7E-7F provide examples of a long stimulation path.

As previously noted, the absence of electrically conductive elements (e.g. electrodes, related connections/wires, etc.) in regions of at least the "upper" portions (e.g. 252C, 254C) of the cuff body, which are distal and proximal to the inner axial, circumferentially-oriented array of electrodes 113A, 113B, 113C may help to minimize or avoid eliciting a response by other nerves and/or other tissue (e.g. muscles) external to the boundaries of the cuff body.

With such arrangements in mind, as shown in FIG. 6A, in some examples electrode 113C may be used to primarily or exclusively stimulate nerve fiber group 262A, 262B (e.g. nerve branches 262A, 262B within main nerve 261) while electrode 113B may be used to primarily or exclusively stimulate nerve fiber group 262C. Meanwhile, via such a selective stimulation arrangement, nerve fiber group 262D may be excluded from stimulation at least by not activating electrode 113A and controlling the intensity and area of stimulation field E1, E2 (shown in dashed lines) from electrodes 113C, 113B, respectively so as to not capture and stimulate nerve fiber group 262D. Alternatively, in some examples, hyperpolarization may be applied via electrode 113A to the nerve fiber group 262D to inhibit activation of nerve fiber group 262D. In examples in which the particular nerve may be the hypoglossal nerve, in some examples nerve fiber group 262D may correspond to a nerve fiber group (e.g. branch) controlling retraction of the tongue while in some examples nerve fiber groups 262A, 262B, and/or 262C may correspond to a nerve fiber group (e.g. branch) controlling protrusion of the tongue.

FIG. 6B is side partial sectional view as taken along lines 6B-6B of FIG. 6A and schematically representing a cuff electrode 270 engaging a nerve 261, according to one example of the present disclosure.

FIGS. 7A-7K are a series of diagrams schematically representing stimulation vectors in association with various electrode array configurations, according to one example of the present disclosure. In FIGS. 7A-7K, an electrode shown in black indicates that the electrode is being utilized as part of a selected electrode configuration to produce a particular stimulation vector. Electrodes label as "A" are used as anodes, while electrodes labeled as "C" are used as a cathode. It will be understood that in some examples, during a single treatment period (e.g. one nighttime therapy), multiple different electrode configurations can be employed such that the designation of a particular electrode(s) as a cathode or anode may change over time depending on which electrode configuration is employed at a particular point in time. In some examples, FIGS. 7A-7K also may be viewed as schematically representing at least an example method of neurostimulation and/or of therapy to treat sleep disordered breathing, such as but not limited to obstructive sleep apnea.

As shown in FIGS. 7A-7B, in this particular configuration 280 of active electrodes, solely the first array of electrodes 103A-103C is employed and in which the outer two electrodes 103A, 103C act as anodes while the inner electrode 103B (same as 113B) acts as a cathode. The two electrodes 113A, 113C remain inactive.

This active electrode configuration 280 may produce an electrical stimulation pattern as shown. As shown in FIG. 7B, in some such examples configuration 280 may produce a field (shown in dashed lines) in which targeted protrusor branches B1, B2 of a nerve (e.g. a hypoglossal nerve) may be captured and stimulated while generally excluding a non-targeted branch B3 from stimulation. In some examples, the non-targeted branch B3 may be non-responsive or exhibit a negative response, as previously described. In some examples, a negative response may include being a retractor branch.

As shown in FIGS. 7C-7D, in this particular configuration 284 of active electrodes, the outer two electrodes 103A, 103C act as anodes while one of the inner electrodes 113A or 113C acts as a cathode. Electrode 103B remains inactive, as well as one of the electrodes 113A or 113C.

This active electrode configuration 284 may produce an example electrical stimulation pattern as shown in which a target protrusor branch B1 may be captured and stimulated while generally excluding non-targeted branches B2 and B3, which may exhibit a negative response or non-response.

As shown in FIGS. 7E-7F, in this particular configuration 286 of active electrodes, the outer two electrodes 103A, 103C act as anodes while both of the inner electrodes 113A and 113C may act cathodes. Electrode 103B (same as 113B) remains inactive.

This active electrode configuration 286 may produce an electrical stimulation pattern as shown in which targeted protrusor branches B1 and B3 may be captured and stimulated while generally excluding branch B2 which may exhibit a negative response or a non-response. In some examples, a negative response may include being a retractor branch.

However, in some examples, all three inner electrodes 113A, 113B, 113C may be act as cathodes.

As shown in FIGS. 7G-7H, in this particular configuration 288 of active electrodes, only the inner electrodes 113A, 113C are active while the outer electrodes 103A, 103C remain inactive.

As shown in FIGS. 7I-7K, in this particular configuration 290 of active electrodes, inner electrode 113B (same as 103B) is active along with one of electrodes 113A (FIG. 7J) or 113C (FIG. 7K) while the outer electrodes 103A, 103C remain inactive.

With regard to the examples of FIGS. 7A-7K, it will be understood that in each instance in which stimulation of a particular nerve branch/group is said to be excluded from stimulation, in some examples hyperpolarization may be applied to the particular nerve branch/group to inhibit its activation.

FIG. 8A is an isometric view schematically representing a cuff electrode 300, according to one example of the present disclosure. In some examples, cuff electrode 300 comprises at least some of substantially the same features and attributes as cuff electrode 100, 200 as previously described in association with at least FIGS. 1-7K, except having additional electrodes in portions of cuff body 101, 201 in which they were omitted in cuff electrode 100, 200. In particular, as shown in FIG. 8B, electrodes 323A and 323C are present in portions 252A, 252C of cuff body 301 while electrodes 333A and 333C are present in portions 254A, 254C of cuff body 301. With this in mind, cuff electrode 300 in FIG. 8A includes an array 330 of electrodes 323A-323C, 313A-313C, 333A-333C in which, in some examples, electrodes 313A, 313C correspond to electrodes 113A, 113B (also 103B), 113C in FIG. 2.

In some examples, each one of the various electrodes 323A-323C, 313A-313C, 333A-333C is independently programmable/controllable. Accordingly, in general terms, a large variety of different combinations of the electrodes of cuff electrode 300 may be activated to stimulate the nerve.

In some examples, the array 332 of outer electrodes 323A, 323B, 323C are electrically common with each other in the circumferential orientation and the array 334 of outer electrodes 333A, 333B, 333C are electrically common with each other in a circumferential orientation.

In some examples, the first array 332 of electrodes and the second array 334 of electrodes are electrically common with each other such that all of the respective electrodes 323A-323C of the first array 332 and the respective electrodes 333A-333C of the second array 334 are programmable together as a single electrical element. Meanwhile, each of the inner electrodes 313A, 313B, 313C are programmable independently relative to each other, and independent of the respective outer electrodes 323A-323C, 333A-333C. Accordingly, in this example the inner electrodes 313A, 313B, 313C comprises three independently programmable electrodes while the group of electrodes 323A-323C, 333A-333C comprise a single programmable electrode, such that the cuff electrode 300 has four independently programmable functional electrodes. In some such examples, this configuration may exhibit lower impedance, which may result in more efficient and/or effective stimulation, such as via more effective hyperpolarization of nearby tissues.

In some examples, the cuff electrode 300 is associated with an implantable pulse generator (IPG) 1110 (FIG. 19A-B) having an external conductive case, which may selectively act as an electrode comparable with the four functional electrodes of cuff electrode 300.

However, in some examples, the first array 332 of outer electrodes 323A, 323B, 323C are electrically common with each other in a circumferential orientation, but electrically independent of the second array 334 of outer electrodes 333A, 333B, 333C, with the respective electrodes 333A, 333B, 333C being electrically common with each other in a circumferential orientation. Via this arrangement, the first array 332 of outer electrodes 323A, 323B, 323C may be activated via a stimulation signal separate from, and independent of the second array 334 of outer electrodes 333A, 333B, 333C such that the activation of the first array 332 is axially unique relative to activation of the second array 334. In some such examples, this configuration may exhibit lower impedance, which may result in more efficient and/or effective stimulation, such as via more effective hyperpolarization of nearby tissues.

FIG. 8B is a diagram including a plan view of the comprehensive array 330 of electrodes 323A-323C, 313A-313C, 333A-333C while FIG. 9 provides a sectional view (as taken along lines 9-9 in FIG. 8A) of electrodes 313A, 313B, 313C. In some examples, the electrodes 313A, 313B, 313C shown in FIG. 9 are representative of electrodes 323A, 323B, 323C and electrodes 333A, 333B, 333C having generally uniform circumferential spacing relative to each other. However, in some examples, the circumferential spacing of the electrodes 313A, 313B, 313C may be non-uniform. Moreover, in some examples, instead of having a 3×3 electrode matrix, cuff electrode 300 may comprise a 4×4 or 3×5, 4×6, etc. electrode matrix.

In some examples, as shown in FIGS. 8B-9, the cuff body 301 includes circumferential portions (e.g. 250A, 250B, 250C) having substantially equal arc lengths (AL5 or W5; AL6 or W6; AL7 or W7). In some examples, at least some of the different circumferential portions have arc lengths which vary from each other.

In some examples, the particular arrangement of electrodes depicted in at least FIGS. 8A-9 may be implemented in a cuff body having a different configuration than the cuff body 301 shown in FIGS. 8A-9. In some examples, the particular arrangement of electrodes depicted in FIGS. 8A-9 may be implemented in the cuff body 101 shown in FIGS. 1-3 and/or the respective cuff bodies shown in FIGS. 14A-14B, 18A, 18B.

In some examples, in a manner similar to that depicted in FIGS. 6A-6B (in which the cuff body releasably contacts a nerve 261) and/or FIGS. 7A-7K, the arrangements shown in FIGS. 8A, 8B, 9 also may be viewed as schematically representing a method of neurostimulation and/or therapy to treat sleep disordered breathing, such as but not limited to obstructive sleep apnea. It will be understood that the nerve 261 is omitted in FIGS. 8A, 9 for illustrative clarity in such examples.

Figure 10:
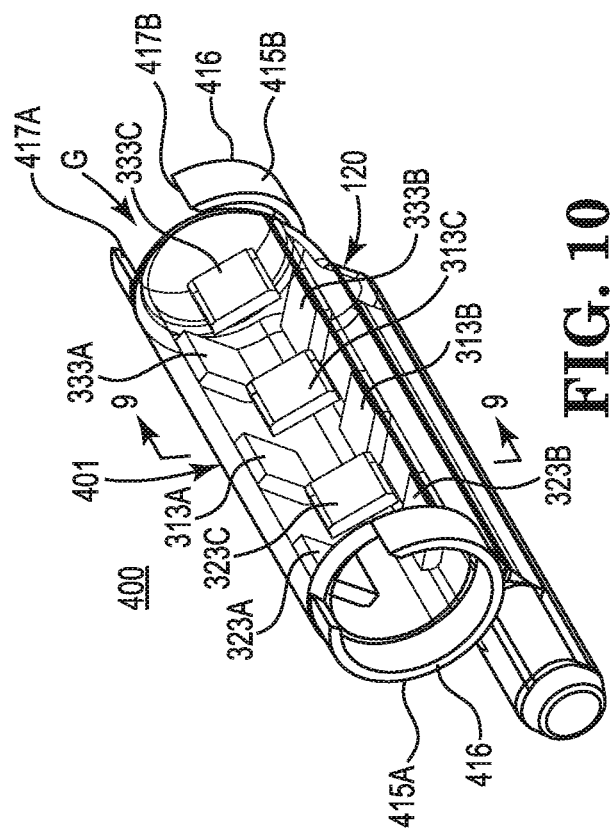
FIG. 10 is an isometric view schematically representing an example cuff electrode.

FIG. 10 is an isometric view schematically representing a cuff electrode 400, according to one example of the present disclosure. In some examples, cuff electrode 400 comprises at least some of substantially the same features and attributes as cuff electrode 300 of FIGS. 8A-9, except for additionally including a pair of ring electrodes 415A, 415B on opposite ends of the cuff body 401 and on opposite ends of the array 330 of electrodes 323A-323C, 313A-313C, 333A-333C. FIG. 10 retains the section lines 9-9 to reflect that a cuff electrode 400 depicted in FIG. 10 may exhibit at least some of substantially the same features and attributes as the cuff electrode 300 represented in the sectional view of FIG. 9. Moreover, it will be understood that, in a manner similar to that depicted in FIGS. 6A-6B (in which the cuff body releasably contacts a nerve 261) and/or FIGS. 7A-7K, the arrangements shown in FIGS. 10-11 also may schematically represent a method of neurostimulation and/or therapy to treat sleep disordered breathing, such as but not limited to obstructive sleep apnea. It will be understood that the nerve 261 is omitted in FIGS. 10-11 for illustrative clarity in such examples.

With further reference to FIG. 10, in some examples, each ring electrode 415A, 415B comprises a split ring electrode having a body 416 extending between two opposite ends 417A, 417B, which in turn define a gap G. In some examples, the gap G is sized and positioned to facilitate opening and closing of the cuff body 401 during implanting the cuff electrode 400 to removably encircle a nerve. Accordingly, the gap G in the ring electrodes 415A, 415B generally corresponds to and/or overlaps with a point of releasable engagement (e.g. 109 in FIGS. 1-5B) between opposing arms of the cuff body (e.g. 101 in FIGS. 1-5B).

In some examples, the gap G may have a different circumferential position than shown in FIG. 10. For instance, gap G may have a circumferential position such as the particular circumferential position for point of releasable engagement 109 of cuff electrode 100 shown in at least FIGS. 1-5B.

In some examples, the ring electrodes 415A, 415B have an inner diameter generally corresponding to a diameter of the lumen 140 defined by cuff body 401 in its closed position. In some examples, the body 416 of each ring electrode 415A, 415B has an arc length which corresponds to 70 to 90 percent of a circle.

In some examples, the respective ring electrodes 415A, 415B are retained in position relative to cuff body 401 and electrodes 323A-323C, 313A-313C, 333A-333C via an overmolding, which is independent of the cuff body 401. In some examples, the overmolding comprises a polyurethane material. In some examples, the overmolding extends from a lead body which extends proximally and/or distally from the cuff body 101. In some examples, this lead body is the same lead body which supports cuff electrode 400 and which is at least partially incorporated within base 120 of cuff body 101.

In some such examples, the lead body and/or cuff electrode 400 may be molded, extruded, adhesively assembled, and/or formed. However, in some such examples, the electrode array and non-conduction portions of the cuff electrode 400 may be manufactured via a printed circuitry manufacturing process and opposing arms of the cuff electrode (and/or other features which may wrap about a nerve) being formed in a complementary manner with the printed electrode array and non-conductive portions of the cuff electrode 400.

In some examples, the ring electrodes 415A, 415B are formed from an electrically conductive material. In some examples, the ring electrodes 415A, 415B may be formed from a material which is resilient and/or semi-rigid.

In some examples, the ring electrodes 415A, 415B may facilitate maintaining a particular position of cuff electrode 400 along a length of the nerve, and may contribute to long term retention of the cuff electrode 400 on the nerve. In one aspect, the resilient and/or semi-rigid material forming the ring electrodes 415A, 415B contribute to such position maintenance and long term retention. In some examples, the semi-rigid material forming the ring electrodes 415A, 415B exhibits sufficient stiffness to resist undue bending or flexing during maneuvering the cuff electrode 400 into encircling engagement about the nerve.

In some examples, the respective ring electrodes 415A, 415B are independently programmable/controllable, while in some examples, the respective ring electrodes 415A, 415B are electrically common with each other.

In some such examples associated with FIG. 10, a greater degree of selectivity may be implemented via the increased number of electrode surfaces. In some examples and as previously noted in association with FIG. 10, the respective electrodes 323A, 313A, 333A comprise a first axial array 440 while respective electrodes 323B, 313B, 333B comprise a second axial array 442, and respective electrodes 323C, 313C, 333C comprise a third axial array 444.

In some examples, cuff electrode 400 comprises the ring electrodes 415A, 415B and just one of the axial arrays 440, 442, 444. In other words, two of the axial arrays 440, 442, 444 are omitted from cuff electrode 400 while retaining the two ring electrodes 415A, 415B.

In some examples, cuff electrode 400 comprises just two of the respective axial arrays 440, 442, 444. In other words, just one of the axial arrays 440,442, 444 is omitted from cuff electrode 400 while retaining the two ring electrodes 415A, 415B.

Figure 11:
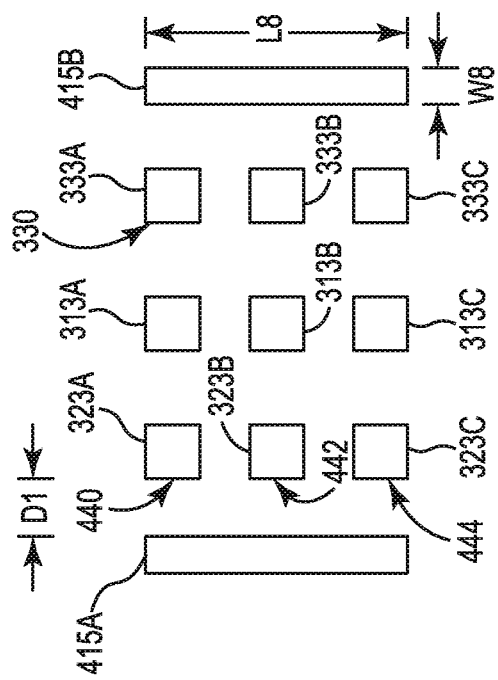
FIG. 11 is a diagram schematically representing an example electrode pattern of the cuff electrode of FIG. 10.

In such examples, in which one or two of the axial arrays 440, 442, 444 are omitted, the remaining axial arrays 440, 442, 444 may be have a different position (according to a circumferential orientation) than shown in FIGS. 10-11.

FIG. 11 is a plan view schematically representing the comprehensive array 330 of electrodes 323A-323C, 313A-313C, 333A-333C and the pair of ring electrodes 415A, 415B, according to one example of the present disclosure. In some examples, each ring electrode 415A, 415B has an arc length (L8) and a width (W8). In some examples, each ring electrode 415A, 415B is spaced apart by a distance D1 from an end of the comprehensive array 330 of electrodes 323A-323C, 313A-313C, 333A-333C.

In some examples, the particular arrangement of electrodes depicted in at least FIGS. 10-11 may be implemented in a cuff body having a different configuration of than the cuff body 401 shown in FIG. 10. In some examples, the particular arrangement of electrodes depicted in FIG. 10 may be implemented in the cuff body 101 shown in FIGS. 1-5B and/or the respective cuff bodies shown in at least FIGS. 14A-14B, 18A-18B.

FIG. 12 is an isometric view schematically representing a cuff electrode 500, according to one example of the present disclosure. FIG. 13A is a plan view schematically representing the array 530 of electrodes 520, 323B-323C, 313B-313C, and 313B-313C of cuff electrode 500 when laid out flat, according to one example of the present disclosure. FIG. 13B is a plan view schematically representing the array 530 of electrodes 520, 323B-323C, 313B-313C, and 313B-313C of cuff electrode 500 as in FIG. 13B, except with elongate electrode 520 in a different circumferential position relative to the other rows of electrodes (in their axial orientation).

In some examples, cuff electrode 500 comprises at least some of substantially the same features and attributes as cuff electrode 300 as previously described in association with at least FIG. 8A-9, except having a single elongate electrode 520 in cuff electrode 500 (FIG. 12) instead of electrodes 323A, 313A, 333A in cuff electrode 300 (FIG. 8A). With this in mind, cuff electrode 500 in FIG. 12 includes an array 530 of electrodes 520, 323B-323C, 313B-313C, and 333B-333C. Via this arrangement, the elongate electrode 520 is common axially to all of the other electrodes 323B-323C, 313B-313C, and 333B-333C of array 530. In some examples, each one of the various electrodes 520, 323B, 323C, 313B, 313C, 333B, and 333C is independently programmable/controllable. Accordingly, in general terms, a large variety of different combinations of the electrodes of cuff electrode 300 may be activated to stimulate the nerve.

In some examples, electrodes 323B, 323C are electrically common with each other to function as a single activatable electrical element, electrodes 313B, 313C are electrically common with each other to function as a single activatable electrical element, and electrodes 333B, 333C are electrically common with each other to function as a single activatable electrical element. Via this arrangement, different axial points along length of nerve may be stimulated.

In some such examples, this configuration may permit use of lower stimulation amplitudes via the relatively larger surface area of the elongate third electrode 520. Upon positioning the electrode configuration in at least some locations, this effect, may in turn, increase generator efficiency and may increase nerve capture. In some examples, the elongate third electrode 520 has a length at least substantially equal to the distance of spacing between two outer electrodes (e.g. 323C, 333C) of one of the axial arrays of electrodes. As such, in some examples, the elongate third electrode 520 may sometimes be referred to as being generally coextensive with one or more of the axial arrays of electrodes (e.g. 323C, 313C, 333C). More particularly, in some examples, the elongate third electrode 520 is generally coextensive with outer ends 339A, 339B of electrodes 323C, 333C. In some examples, the elongate third electrode 520 is generally coextensive at least through inner ends 338A, 338B of the outer electrodes (e.g. 323C, 333C) of one of the axial arrays of electrodes.

In some examples, the elongate third electrode 520 has an arc length (in the circumferential orientation) which is substantially the same as an arc length of the other electrodes of the cuff electrode. However, in some examples, the elongate third electrode 520 has an arc length (in the circumferential orientation) which substantially greater than the arc length of the other electrodes of the cuff electrode. In some such examples, this greater arc length may enable a reduction in overall cuff length, which in turn may enable greater maneuverability of the cuff body to enhance surgical delivery of the cuff. In some examples, an elongate third electrode 520 may located, in a circumferential orientation, closer to or overlapping with a spine (e.g. base 120 in FIG. 1) of the cuff/lead so as to minimize any impact on overall cuff flexibility.

In some examples, the particular arrangement of electrodes depicted for cuff electrode 501 in FIG. 12 may be implemented in a cuff body having a different configuration than the cuff body 501 shown in FIG. 12. In some examples, the particular arrangement of electrodes depicted in FIG. 12 may be implemented in the cuff body 101, 201 shown in FIGS. 1-6B and/or the respective cuff bodies shown in FIGS. 14A-14B and 18A, 18B.

FIG. 12 retains the section lines 9-9 to reflect that a cuff electrode 500 may exhibit at least some of substantially the same features and attributes as the cuff electrode 300 represented in the sectional view of FIG. 9. Moreover, it will be understood that, in a manner similar to that depicted in FIGS. 6A-6B (in which the cuff body releasably contacts a nerve 261) and/or FIGS. 7A-7K, the arrangements shown in FIGS. 12-13B also may schematically represent a method of neurostimulation and/or therapy to treat sleep disordered breathing, such as but not limited to obstructive sleep apnea. It will be understood that the nerve 261 is omitted in FIGS. 12-13B for illustrative clarity in such examples.

Figure 14A:
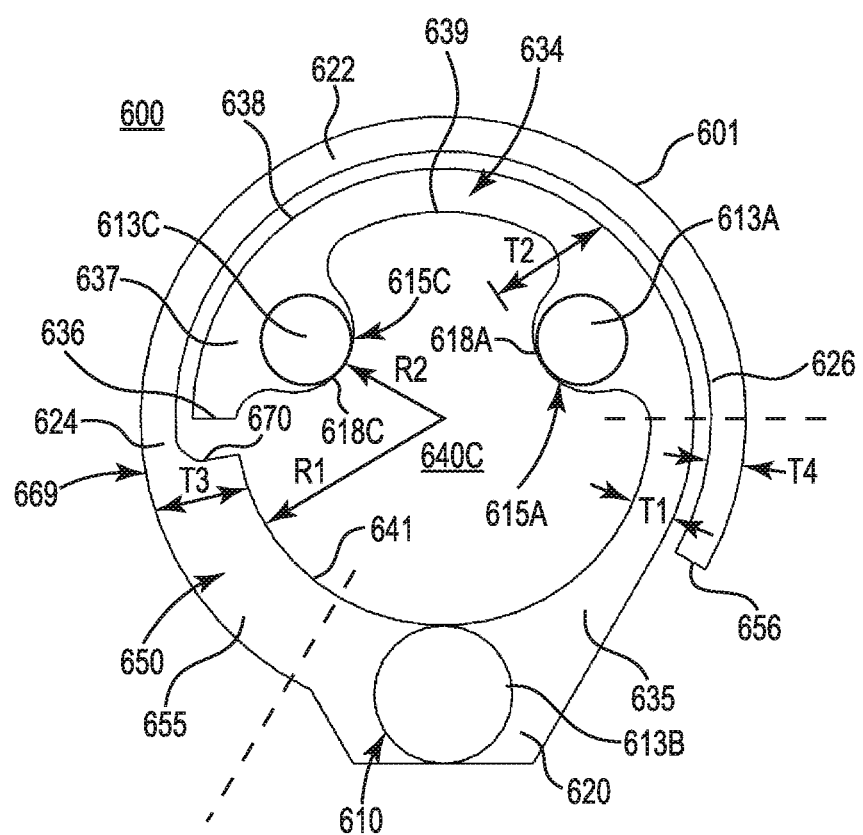
FIG. 14A is a sectional view schematically representing an example cuff electrode including some electrodes partially housed within inwardly-oriented protrusions of a nerve-contact surface.

FIG. 14A is a sectional view schematically representing a cuff electrode 600, according to one example of the present disclosure.

As shown in FIG. 14A, in at least some examples, cuff electrode 600 comprises at least some of substantially the same features and attributes as the cuff electrode 100, 200 of FIGS. 1-6B and FIGS. 7A-7K. For instance, in some examples cuff electrode 600 may have a first array 610 of electrodes 603A, 603B, 603C (e.g. first electrodes) extending axially like electrodes 103A, 103B, 103C (FIGS. 1-2) and a second array 612 of electrodes 613A, 613B, 613C (e.g. second electrodes) extending in a circumferential orientation perpendicular to the axial orientation with electrode 613B also acting as electrode 603B. Accordingly, in such a configuration some portions (e.g. 252A, 254A, 252C, 254C in FIG. 5A) of a cuff body 601 omits electrodes and define cuff body portions free from electrically conductive elements.

However, unlike the configuration of electrodes 113A, 113B, 113C in FIGS. 1-6B, in the cuff electrode 600 of FIG. 14A two electrodes 613C, 613A are included on a single arm (e.g. first arm 634) while the other arm 650 omits any electrodes. Moreover, the third electrode 613B (same as 103B) is located at or near base 620. In such a configuration, the electrodes 613C, 613A are located away from the lead body attachment/spine, which in some examples may contribute to generally equal circumferential spacing between the three inner electrodes 613C, 613A, 613B. Other differences relative to the cuff electrode 100, 200 in FIGS. 1-6B are described further below and/or are observable from FIG. 14A.

As further shown in FIG. 14A, the cuff body 601 comprises a first arm 634 and a second arm 650. The first arm 634 has a proximal portion 635 and an opposite distal portion 637 having distal end 636. The first arm 634 also comprises an outer surface 638 and an inner surface 639, which at least partially defines nerve-contact surface 641 of cuff body 601. The proximal portion 635 of first arm 634 extends from the base 620 and has a thickness T1. In some examples, the first arm 634 has at least one segment with a thickness which varies. In some such examples, the at least one segment of varying thickness comprises at least one segment of increased thickness relative to other portions of the first arm 634. In some examples, the at least one segment of varying thickness may be implemented to house electrodes 613C, 613A. In some examples, the at least one segment of first arm 634 having the varying thickness corresponds to an outer circumferential portion of a cuff body, such as portion 651C in FIG. 15A, portions 652C, 651C, 654C in FIGS. 15B, 15C, 15D, portion 721B in FIG. 17A, and portions 722B, 721B, 724B in FIG. 17B-17C.

In some examples, the at least one segment of first arm 634 exhibiting varying thickness may be implemented as protrusions 615B, 615C which are oriented inwardly within the lumen 640C defined by the cuff body 601 and which partially define nerve-contact surface 641 of lumen 640C. In some instances, these inwardly-oriented protrusions 615A, 615C may be referred to as inward protrusions or internal protrusions. In some examples, each inwardly-oriented protrusion 615A, 615C comprises a generally convex shape, which stands in contrast to the generally concave shape of portions of the nerve-contact surface 641 other than inwardly-oriented protrusions 615A, 615C. In some examples, at its apex, each protrusion 615A, 615C has a thickness T2, which is substantially greater than the thickness T1 of the non-protruding portions of the first arm 634. In some examples, T2 is at least two times T1. In some such examples, this increased thickness may ease molding of electrodes (e.g. 613C, 613A) into the arm 634 of the cuff body, and the cuff body generally. In some examples, the protrusions 615A, 615C are circumferentially spaced apart by a distance equal to the equal circumferential spacing of electrodes 613A, 613B, 613C.

Figure 14B:
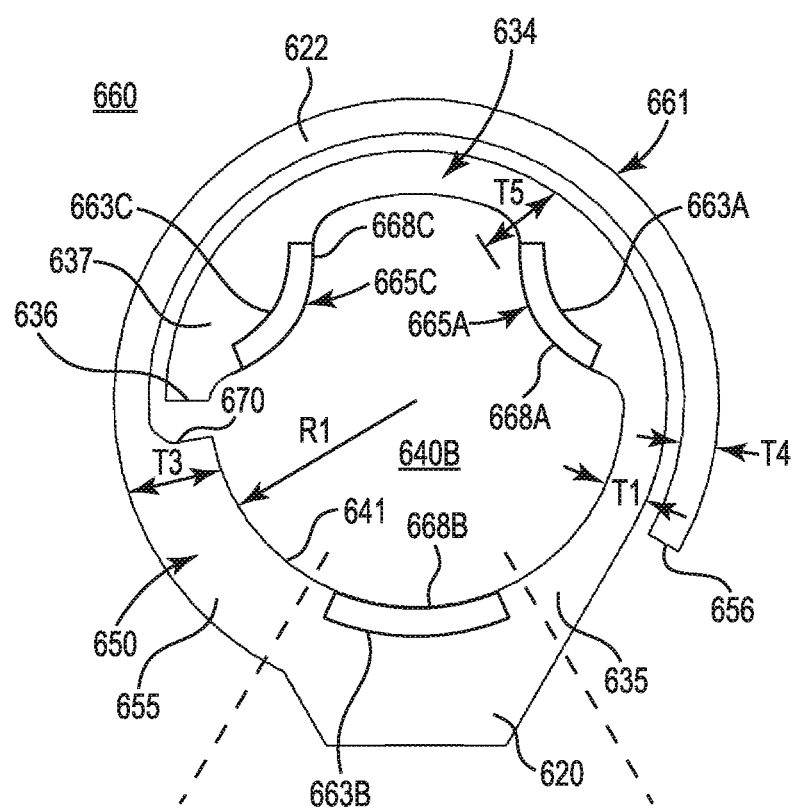
FIG. 14B is a sectional view schematically representing an example cuff electrode including some electrodes partially housed within inwardly-oriented protrusions of a nerve-contact surface.
Figure 18A:
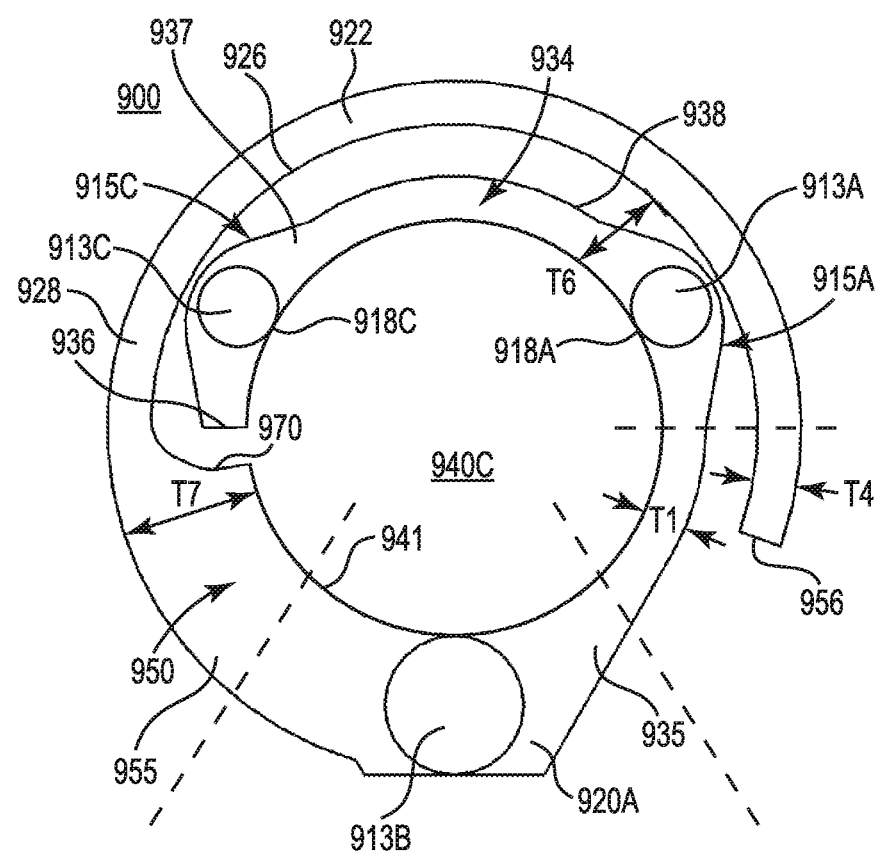
FIG. 18A is a sectional view schematically representing an example cuff electrode including some electrodes partially housed within outwardly-oriented protrusions.
Figure 18B:
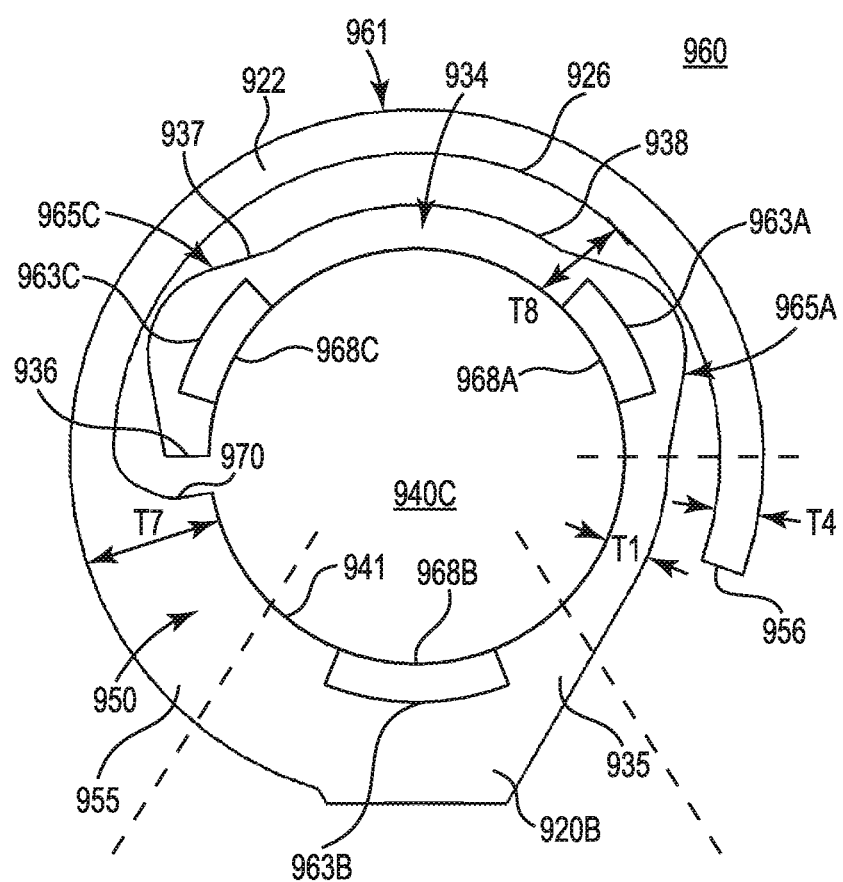
FIG. 18B is a sectional view schematically representing an example cuff electrode including some electrodes partially housed within outwardly-oriented protrusions.

While FIG. 14A-14B depicts inwardly-oriented protrusions 615C, 615A, and while FIGS. 18A-18B depict outwardly-oriented protrusions, it will be understood that some examples may include similar protrusions in which one or more such protrusions (housing electrodes 613C, 613A) may include both an inwardly-oriented portion and an outwardly-oriented portion and/or may include shapes other than those shown in FIGS. 14A-14B or 18A-18B to provide a relatively increased thickness in an area of the arm to at least partially house electrodes.

Each protrusion 615C, 615A at least partially houses the respective electrodes 613C, 613A. In some examples, each protrusion 615C, 615A has a volume sufficient to securely retain each electrode 613C, 613A, associated hardware, and conductive lead wires that extend through select portions (e.g. inner axial portions (651C, 651B in FIG. 15A) of cuff body 601. As shown in FIG. 14A, each protrusion 615C, 615A may be formed and/or shaped to expose at least a portion of the respective electrodes 613C, 613A at the nerve-contact surface 641 of the cuff body 601 to engage the nerve.

The electrodes 613C, 613A may be implemented in a variety of shapes, such as but not limited to the spherical shape shown in the sectional view of FIG. 14A. For instance, the electrodes may have a cylindrical shape with an outer curved surface exposed at the nerve-contact surface 641 of the lumen 640. In other instances, as shown later in FIG. 14B, electrodes 663C, 663A may have an arc shape which matches the general contour of the protrusions 665C, 665A.

In some examples, the inwardly-oriented protrusions 615C, 615A may cause the exposed electrode surface 618C, 618A to define a radius R2 relative to center of lumen 640C that is less than a radius R1 of remainder of nerve-contact surface 641 of the lumen. In some examples, R2 is substantially less than R1. In some examples, the varying thickness and radius of the first arm 634 may sometimes be referred to as a circumferential profile of the nerve-contact surface 641 extending along first arm 634.

In some examples, the inwardly-oriented protrusions in which the electrodes are housed may enhance operable coupling of the electrode relative to one or more nerve groups within the nerve. For instance, in at least some examples, at least some branches/fibers within the nerve may adapt and flow around/about the respective protrusions, thereby resulting in the various nerve branches being in close proximity to the respective electrodes (within the respective protrusions) to establish good connectivity between the nerve (branches) and the electrodes.

The second arm 650 comprises a proximal portion 655 and a distal portion 622 with a distal end 656. The proximal portion 655 has a thickness T3 while the distal portion 622 has a thickness T4. In some examples, an arc length of the distal portion 622 of second arm 650 overlaps a substantial majority of the arc length of the first arm 634. In some examples, the overlap corresponds to at least about 30 degrees of arc length.

In some examples, second arm 650 comprises a transition portion 669 defining a transition between the proximal portion 655 and distal portion 622. In some examples, transition portion 669 includes a shelf 670 defined by an end of proximal portion 655 of second arm 650 and includes a proximal end 624 of distal portion 622 of second arm 650.

While generous spacing is shown in FIG. 14A between distal end 636 of first arm 634 and the shelf 670 of second arm 650, it will be understood that it is intended that shelf 670 provides an area by which distal end 636 of first arm 634 may make releasable contact with second arm 650. This arrangement limits the extent of rotational movement of first arm 634, which may bolster structural integrity of cuff body 101 and also defines minimum diameter of lumen 640C so as to prevent undue pressure and/or constriction on a nerve.

Moreover, the greater thickness T3 of the proximal portion 655 of second arm 650 provides additional structural strength to support releasable contact from distal end 636 of first arm 634 and/or to maintain a shape of lumen 640C.

In some examples, the shelf 670 has a width W generally the same as or wider than the width W of the distal end 636 of the first arm 634.

In addition to the shelf 670, the transition portion 669 includes the distal portion 622 extending directly from the proximal portion 655. In some examples, the distal portion 622 has a generally uniform thickness T4 throughout its length. In some examples, the distal portion 622 of the second arm 650 has an inner surface 626 defining a generally constant radius of curvature while the outer surface 638 of the first arm 634 has a generally constant radius of curvature that generally matches the radius of curvature of the inner surface 626 of the distal portion 622 of the second arm 650. Via this arrangement, in its overlapping relation with the at least the first arm 634, the distal portion 622 of the second arm 650 lies generally flat against the first arm 634. This arrangement may enhance the integrity and holding strength of cuff body 601 relative to the nerve, while simultaneously accommodating any temporary nerve swelling upon implantation and/or accommodating different size nerves.

Each arm 634, 650 is shaped and formed of a resilient material such that the opposingly-oriented arms 634, 650 are biased into the configuration shown in FIG. 14A to remain in a releasably secured position about a nerve. However, each arm 634, 650 has sufficient flexibility to permit being manipulation of the distal portion 622 of second arm 650 and distal portion 637 of first arm 634 to enable opening cuff body 601 to receive nerve within lumen 640C, and upon release of the respective arms 634, 650, to return the cuff body 601 to the closed configuration shown in FIG. 14A.

In defining different circumferential portions and/or different axial portions of the cuff body 601 of FIG. 14A, it will be understood that in comparison to the example of FIGS. 1-6B, in some examples the first arm 634 and the proximal portion 655 of the second arm 650 may be considered analogous to the first arm 134 and to the second arm 150, respectively.

FIG. 14B is sectional view schematically representing a cuff electrode 660, according to one example of the present disclosure. In some examples, the cuff electrode 660 (including cuff body 661) comprises at least some of substantially the same features and attributes of cuff electrode 600 of FIG. 14A (including cuff body 601), except for the inwardly-oriented protrusions 665C, 665A having a lower radial profile (i.e. less thickness) and the electrodes 663C, 663B, 663A having an arc shape instead of a spherical or cylindrical shape. In some examples, a thickness T5 of each inwardly-oriented protrusion 665C, 665A has a thickness T5 is substantially less than a thickness T2 of the inwardly-oriented protrusions 615C, 615A of the cuff electrode 600 in FIG. 14A. In some examples, the thickness T5 is no more than twice the thickness T1 of the proximal portion 635 of the first arm 634.

In some examples, the arc-shaped electrodes 663C, 663A comprise a convex-shaped electrode contact surface 668C, 668A within lumen 640B for releasably contacting a nerve. In some examples, the arc-shaped electrode 663B comprises a concave-shaped electrode contact surface 668B for releasably contacting the nerve within lumen 640B.

It will be understood that in some examples, electrodes 663C, 663A may have shapes other than an arc-shape. For instance, the electrodes 663C, 663A may be concave or even flat (e.g. not curved), or other convex-shaped, disc-shaped, etc. with adjacent portions of the protrusion supporting the electrode shape in a complementary manner to yield a suitable nerve-electrode interface.

Figure 15A:
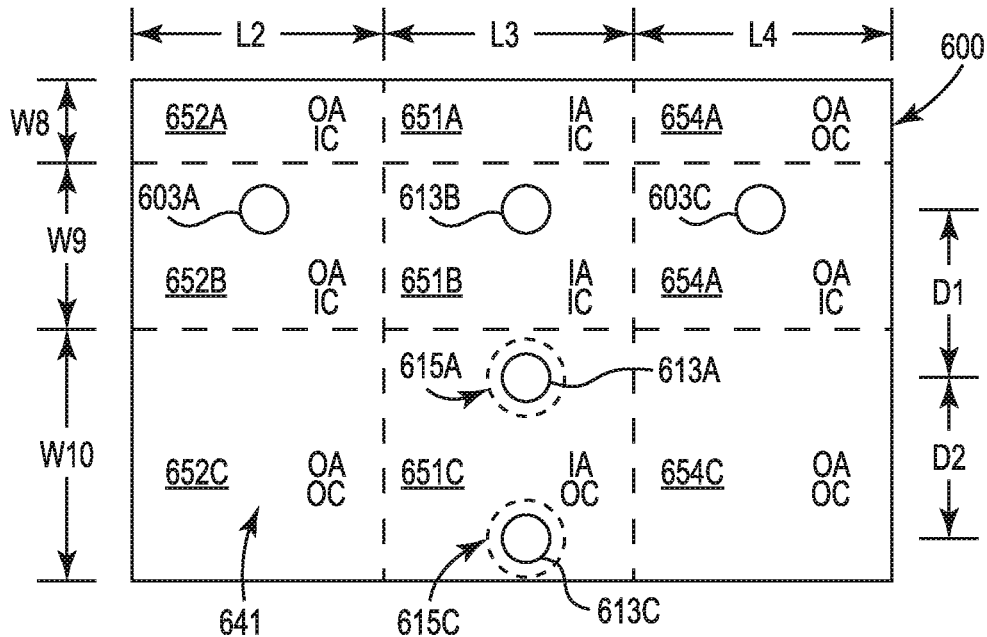
FIG. 15A is a diagram including a plan view schematically representing a nerve-contact surface of an example cuff electrode and example electrode pattern relative to some circular-shaped and inwardly-oriented protrusions of the nerve-contact surface.

FIG. 15A is a diagram including a plan view schematically representing a nerve-contact surface 641 and an electrode pattern associated with the cuff electrodes 600, 660 in FIGS. 14A-14B, according to one example of the present disclosure. In some examples, the cuff electrode 600 of FIG. 15A comprises at least some of substantially the same features and attributes as cuff electrode 600 (FIG. 14A) and cuff electrode 660 (FIG. 14B). For simplicity, further discussion regarding FIG. 15A will refer solely to cuff electrode 600 even though it will be applicable to both cuff electrodes 600 (FIG. 14A), 660 (FIG. 14B).

In some examples, the cuff electrode 600 in FIG. 15A comprises different circumferential portions and axial portions of a cuff body 601 in the substantially the same manner as the different portions of the cuff body 101, 201 for the cuff electrode in FIG. 3-5B. With this in mind, the inner circumferential portions 652B, 651B, 654B of cuff body 101 house electrodes 603A, 603B (same as 613B), 603C, respectively, while the outer circumferential portion 651C (also an inner axial portion) houses electrodes 613A, 613C. In some examples, the outer circumferential portion 651C generally corresponds to at least the distal portion 637 of first arm 634 (FIG. 14A).

As shown in FIG. 15A, in some examples the circumferential array of electrodes 613B, 613A, 613C are equally spaced apart, as represented by distances D1 and D2.

Meanwhile, the dashed lines 615A, 615C in FIG. 15A represent the inner protrusions 615A, 615C (FIG. 14A) when the inner protrusions are implemented as generally circular elements within portion 651C of cuff body 601. In some such configurations, the generally circular elements may facilitate molding and/or retention of the electrodes within the cuff body.

Figure 15B:
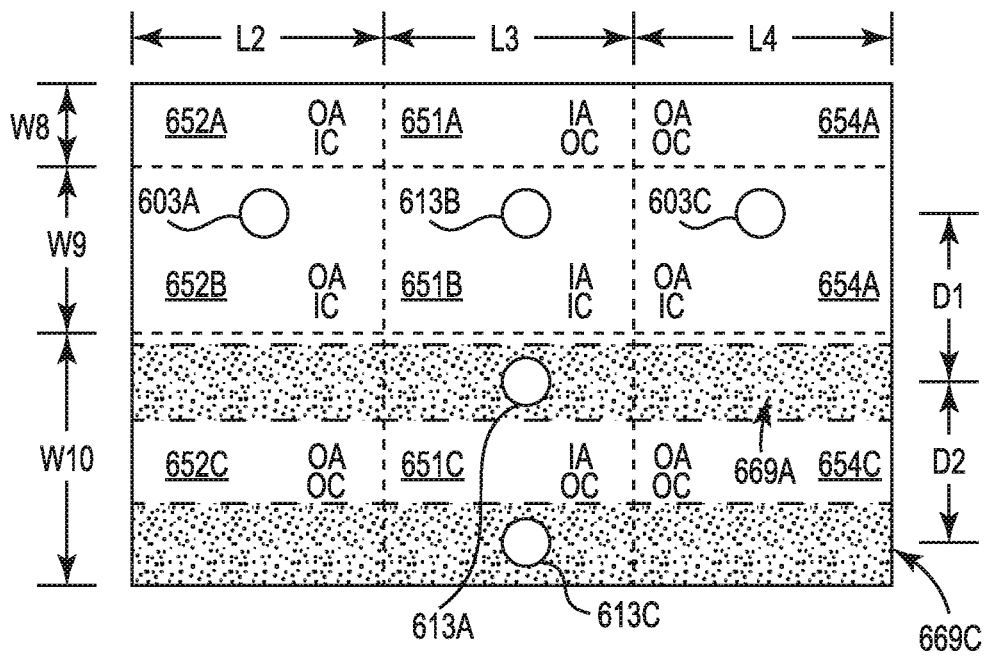
FIG. 15B is a diagram including a plan view schematically representing a nerve-contact surface of an example cuff electrode and example electrode pattern relative to some elongate inwardly-oriented protrusions of the nerve-contact surface.

However, in some examples, as shown in FIG. 15B, the inner protrusions 615A, 615C are implemented as elongate elements represented by shaded regions 669A, 669C which may extend a length (L1) of the cuff body 601. In some such configurations, the elongate elements may facilitate molding and/or retention of the electrodes within the cuff body, as well as routing of wires within/through the cuff body.

Figure 15C:
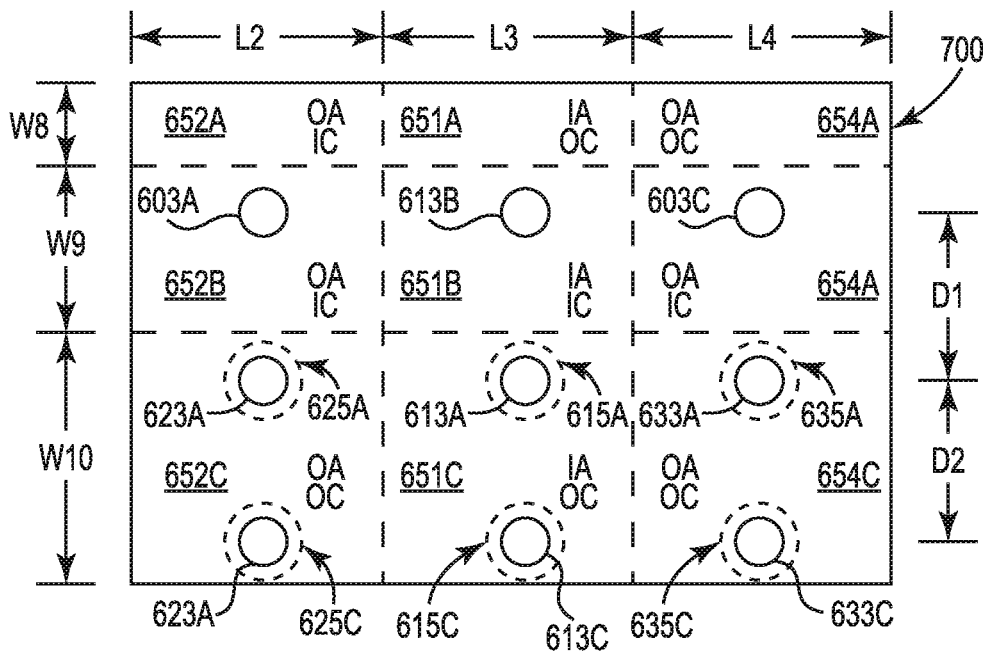
FIG. 15C is a diagram including a plan view schematically representing a nerve-contact surface of an example cuff electrode and example electrode pattern relative to some circular-shaped inwardly-oriented protrusions of the nerve-contact surface.

FIG. 15C is a diagram including a plan view schematically representing a nerve-contact surface of a cuff electrode 700 and electrode pattern relative to some circular-shaped, inwardly-oriented protrusions of a nerve-contact surface, according to one example of the present disclosure. The cuff electrode 700 comprises at least some of substantially the same features as cuff electrode 600 in FIG. 15A, except having electrodes 623A, 623C in portion 652C and electrodes 633A, 633C in portion 654C with each of these electrodes housed in an inwardly-oriented protrusion 625A, 625C, 635A, 635C, respectively with inwardly-oriented protrusions 625A, 625C, 635A, 635C having substantially the same features as inwardly-oriented protrusions 615A, 615C (FIG. 14A) or 665A, 665C (FIG. 14B).

In some examples, the general electrode pattern in cuff electrode 700 comprises at least some of substantially the same features and attributes as cuff electrode 300 in FIG. 8A-9, as least to the extent that cuff electrode 700 comprises three axial arrays of electrodes and the manner in which they may operate together or independently.

Figure 15D:
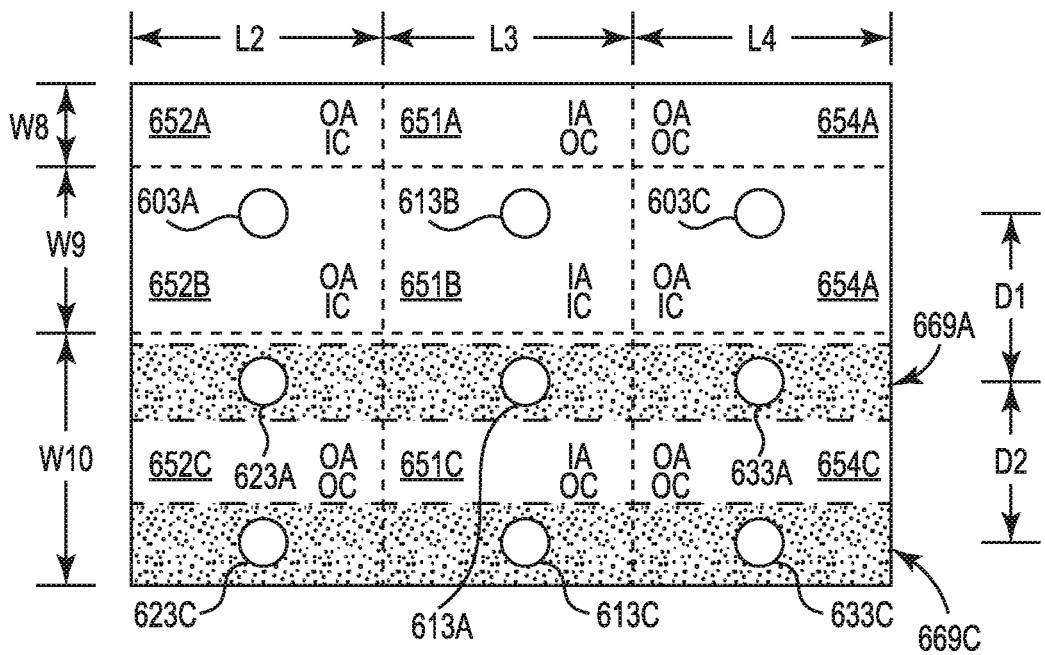
FIG. 15D is a diagram including a plan view schematically representing a nerve-contact surface of an example cuff electrode and example electrode pattern relative to some elongate inwardly-oriented protrusions of the nerve-contact surface.

In some examples, as shown in FIG. 15D, the inwardly-oriented protrusions housing the electrodes 623A, 623C (in portion 652C), 613A, 613C (in portion 651C), 633A, 633C (in portion 654C) are implemented as elongate elements represented by shaded regions 669A, 669B in a manner similar to that shown in FIG. 15B.

It will be understood that, in a manner similar to that depicted in FIGS. 6A-6B (in which the cuff body releasably contacts a nerve 261) and/or FIGS. 7A-7K, the arrangements shown in FIGS. 14A-14B, 15A-15C also may schematically represent a method of neurostimulation and/or therapy to treat sleep disordered breathing, such as but not limited to obstructive sleep apnea. It will be understood that the nerve 261 is omitted in FIGS. 14A-14B, 15A-15C for illustrative clarity in such examples.

Figure 16:
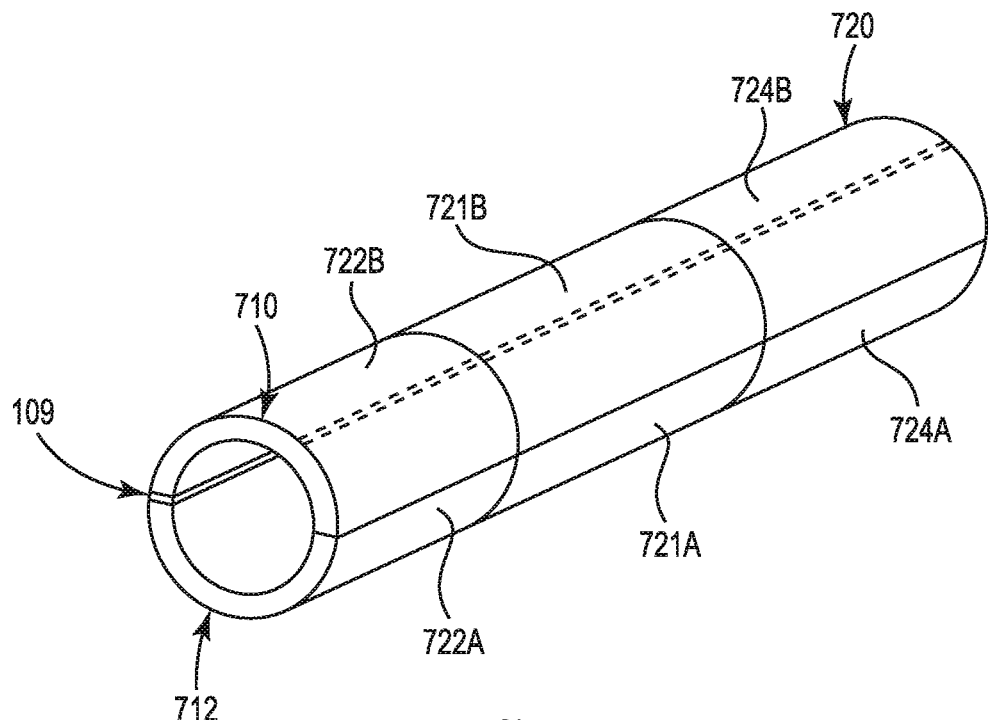
FIG. 16 is a diagram including an isometric view schematically representing different portions of an example cuff body.

FIG. 16 is a diagram including an isometric view schematically representing different portions of a cuff body 720 for a cuff electrode like that of FIGS. 14A-14B, according to one example of the present disclosure. In some examples, the cuff body 720 comprises at least some of substantially the same features and attributes as the cuff body 101, 201 (FIGS. 1-6B), except with cuff body apportioned as two circumferential portions instead of as three (two outer, one inner) circumferential portions. Accordingly, in some examples, the cuff body 720 includes a first circumferential portion 710 and a second circumferential portion 712. In some examples, the respective first and second circumferential portions 710, 712 may sometimes be referred to as first and second half portions or as an upper half portion 710 and lower half portion 712. In some instances, the lower half portion 712 may sometimes be referred to as a lower circumferential portion while the upper half portion 710 may sometimes be referred to as an upper circumferential portion.

In some examples, the lower half portion 712 has an arc length or width W11, while the upper half portion 710 has an arc length or width W12, which is generally equal to W11.

Figure 17A:
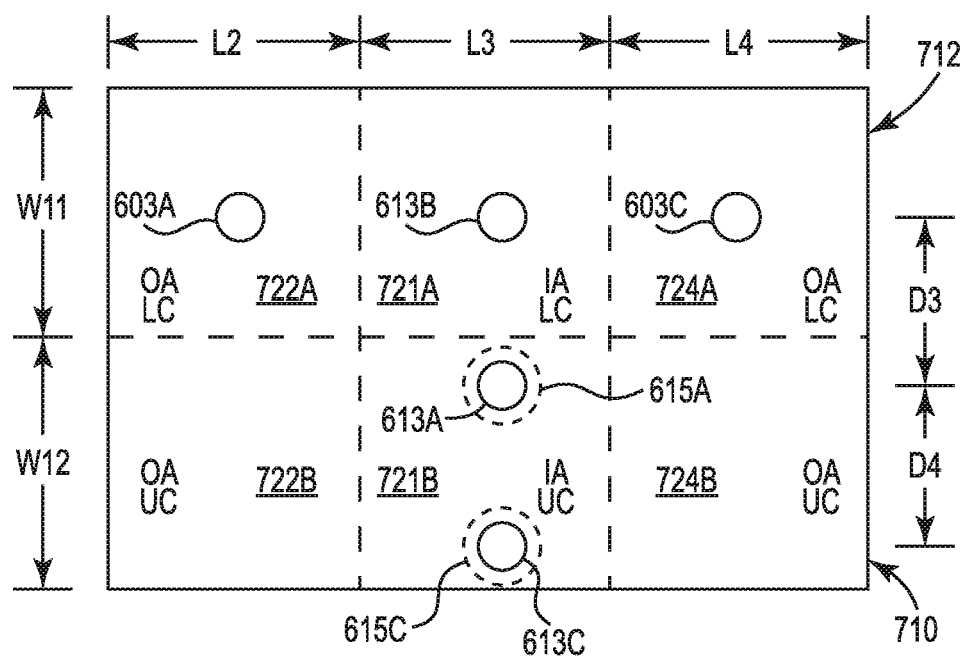
FIG. 17A is a diagram including a plan view schematically representing a nerve-contact surface of an example cuff electrode and example electrode pattern relative to some circular-shaped inwardly-oriented protrusions of the nerve-contact surface.

Accordingly, as shown in FIG. 17A, electrodes 603A, 603B, 603C extend axially with one electrode present in each of the portions 722A, 721A, 724A of cuff body 720 while electrodes 613A, 613B, 613C extend in a circumferential orientation with both electrodes 613A, 613C residing in portion 721B. Portions 722B, 724B omit any electrodes. As represented via the dashed lines 615A, 615C, each electrode 613A, 613C is housed in a circular-shaped inwardly-oriented protrusion in a manner as previously described in association with at least FIG. 15A, 15C to implement housing an electrode via the inwardly-oriented protrusions as in FIG. 14A or 14B.

In some examples, each of the upper circumferential, outer axial cuff body portions 722B, 724B omit electrodes (and therefore are generally electrically conductive-free portions).

Figure 17B:
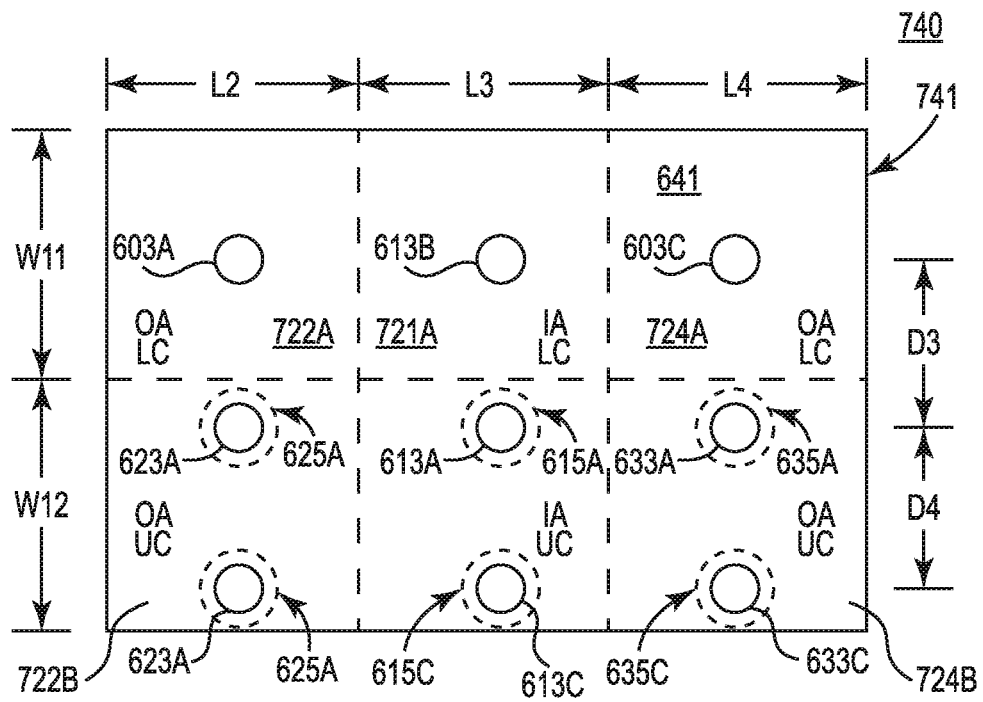
FIG. 17B is a diagram including a plan view schematically representing a nerve-contact surface of an example cuff electrode and example electrode pattern relative to some circular-shaped inwardly-oriented protrusions of the nerve-contact surface.

FIG. 17B is a diagram including a plan view schematically representing a nerve-contact surface 641 of a cuff electrode 740 and electrode pattern relative to some circular-shaped inwardly-oriented protrusions of a nerve-contact surface, according to one example of the present disclosure. The cuff electrode 740 comprises at least some of substantially the same features as cuff electrode 700 in FIG. 15C, except for cuff body 741 apportioned as two circumferential portions rather than thee circumferential portions (two outer, one inner) in FIG. 15C. Accordingly, as shown in FIG. 17B, in cuff electrode 740 the portion 722B includes electrodes 623A, 623C while portion 724B includes electrodes 633A, 633C. Each of these electrodes are housed in an inwardly-oriented protrusion 625A, 625C, 635A, 635C, respectively with inwardly-oriented protrusions 625A, 625C, 635A, 635C having substantially the same features as inwardly-oriented protrusions 615A, 615C (FIG. 14A) or 665A, 665C (FIG. 14B).

In some examples, the general electrode pattern in cuff electrode 740 in FIG. 17B comprises at least some of substantially the same features and attributes as cuff electrode 300 in FIG. 8A-9, as least to the extent that cuff electrode 740 comprises three axial arrays of electrodes and the manner in which they may operate together or independently.

Figure 17C:
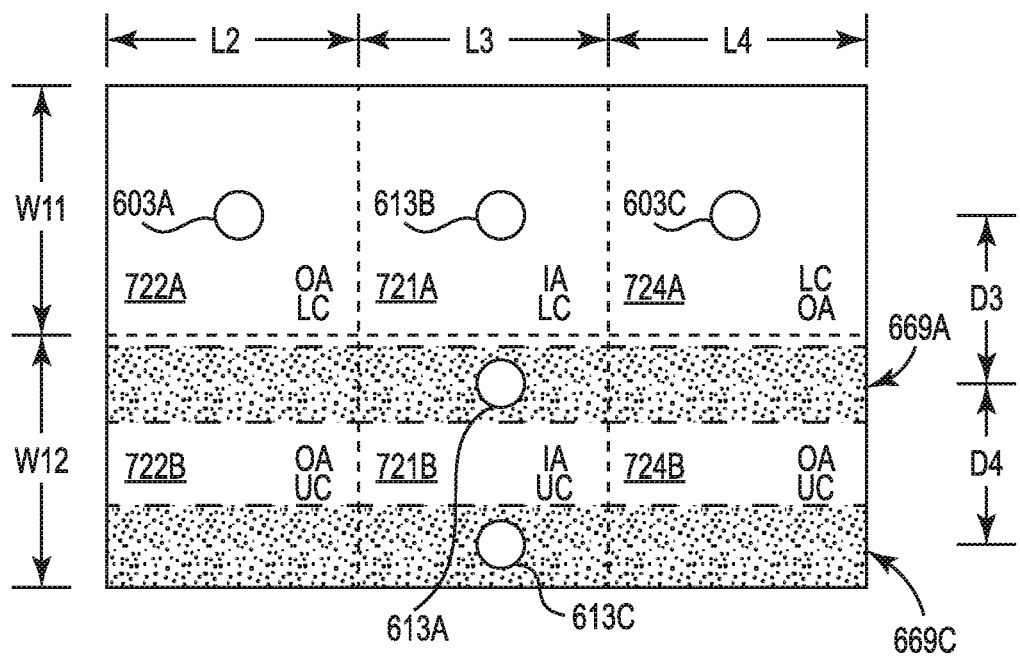
FIG. 17C is a diagram including a plan view schematically representing a nerve-contact surface of an example cuff electrode and example electrode pattern relative to some elongate inwardly-oriented protrusions of a nerve-contact surface.

In some examples, as shown in FIG. 17C, a cuff electrode 750 includes inwardly-oriented protrusions (to house the electrodes) implemented as elongate elements represented by shaded regions 669A, 669B in a manner similar to that shown in FIG. 15B.

With further reference to the example of FIG. 17C in which the inwardly-oriented protrusions are implemented as elongate elements (i.e. shaded regions 669A, 669C), additional electrodes 623A, 623C may be implemented in portion 722B) and additional electrodes 633A, 633C may be implemented in portion 724B. In such examples, the general electrode pattern in cuff electrode 750 in FIG. 17C comprises at least some of substantially the same features and attributes as cuff electrode 300 in FIG. 8A-9, as least to the extent that cuff electrode 700 would comprise three axial arrays of electrodes and the manner in which they may operate together or independently.

It will be understood that, in a manner similar to that depicted in FIGS. 6A-6B (in which the cuff body releasably contacts a nerve 261) and/or FIGS. 7A-7K, the arrangements shown in FIGS. 16-17C also may schematically represent a method of neurostimulation and/or therapy to treat sleep disordered breathing, such as but not limited to obstructive sleep apnea. It will be understood that the nerve 261 is omitted in FIGS. 16-17C for illustrative clarity in such examples.

FIG. 18A is a sectional view schematically representing cuff electrode 900, according to one example of the present disclosure. In some examples, cuff electrode 900 comprises at least some of substantially the same features and attributes as cuff electrode 600, 660 in FIG. 14A-14B, except for having outwardly-oriented protrusions 915C, 915A to at least partially house electrodes 913C, 913A instead of the inwardly-oriented protrusions 615C, 615A of the cuff electrode 600 in FIG. 14A-14B.

In some examples, the cuff electrode 900 has a second arm 950 like second arm 650 of cuff electrode 600 in FIG. 14A-14B, except with the second arm 950 having a proximal portion 955 with a thickness T7 greater than a thickness T3 (FIG. 14A) of proximal portion 655 of second arm 650 of cuff body 601. In some examples, the greater thickness T7 is provided so that the inner surface of proximal portion 955 (of second arm 950) defining part of nerve-contact surface 941 will match and/or complement the radius of the other portions of the nerve-contact surface 941 of cuff body 901. This arrangement also positions the proximal portion 928 of the distal portion 922 of second arm 950 to orient the contour of the inner surface 926 of the distal portion 922 to accommodate the outwardly-oriented protrusions 915C, 915A in a manner such that the bias of the distal portion 922 will result in the distal portion 922 wrapping in a complementary relationship about the outer surface 938 (including the outward protrusions 915C, 915A) of the first arm 934.

As further shown in FIG. 18A, like in the example of FIG. 14A the first arm 934 comprises a proximal portion 935 extending from a base 920A of cuff electrode 900 and comprises an opposite distal portion 937 having a distal end 936. Moreover, the second arm 950 comprises a proximal portion 955 and an opposite distal portion 922 having distal end 956.

In contrast with the examples in FIGS. 14A-14B, in the present arrangement of outwardly-oriented protrusions 915C, 915A, the extra space involved in housing the electrodes 913C, 913A (and related conductive wires) is oriented outward away from the nerve-contact surface 941. Via this arrangement the nerve-contact surface 941 of the cuff body 901 defined by lumen 940C maintains a generally uniform radius of curvature such that the contact surface 918C, 918A of the electrodes 913C, 913A are generally flush with other portions of the nerve-contact surface 941 of the cuff body 901. Via this arrangement, the nerve-contact surface 941 of the cuff electrode 900 as a whole is highly complementary of the outer surface/circumference of the nerve to which it is engaged.

FIG. 18B is a sectional view schematically representing a cuff electrode 960, according to one example of the present disclosure. In some examples, cuff electrode 960 comprises at least some of substantially the same features and attributes as cuff electrode 900 (FIG. 18A), except having arc-shaped electrodes 963C, 963A instead of spherically-shaped or cylindrically-shaped electrodes 913C, 913A (FIG. 18A). In some examples, a thickness T8 of the outward protrusions 965C, 965A is less than a thickness T6 of the outward protrusions 915C, 915A (FIG. 18A) because of a lower radial profile of the arc-shaped electrodes 963C, 963A. In some examples, the electrodes 963C, 963A have concave-shaped nerve-contact surfaces 968C, 968A which are generally flush with the nerve-contact surface 941 of the cuff body 961. Via this arrangement, while the outwardly-oriented protrusions 965C, 965A accommodate the volume of the electrodes 963C, 963A and connected conductive lead wires (and associated connection structures), the nerve-contact surface 941 of the cuff body 961 retains a generally uniform radius which may facilitate close engagement relative to the nerve.

As further shown in FIG. 18B, like in the example of FIG. 18A the first arm 934 comprises a proximal portion 935 extending from a base 920B of cuff electrode 960 and comprises an opposite distal portion 937 having a distal end 936. Moreover, the second arm 950 comprises a proximal portion 955 and an opposite distal portion 922 having distal end 956. As further shown in FIG. 18B, in some examples, the arc-shaped electrodes 963C, 963B, 963A comprise a concave-shaped electrode contact surface 968C, 968B, 968A of nerve-contact surface 941 within lumen 940C for releasably contacting a nerve.

In some examples, the respective cuff electrode 900 and 960 of FIGS. 18A, 18B may comprise any one of (or combinations of) the various electrode configurations and/or cuff body configurations as previously described in association with FIGS. 15A-15D, 16, 17A-17C, except for being implemented with outwardly-oriented protrusions (915C, 915A, 965C, 965A in FIGS. 18A, 18B) instead of with inwardly-oriented protrusions (615C, 615A, 665C, 665A in FIGS. 14A, 14B).

In some examples, the electrodes 613C, 613B, 613A (FIG. 14A), electrodes 663C, 663B, 663A (FIG. 14B), electrodes 913C, 913B, 913A (FIG. 18A), and/or electrodes 963C, 963B, 963A (FIG. 18B) may be implemented within a cuff body of a cuff electrode having at least some of substantially the same features and attributes as one of the cuff electrodes described in Bonde et al. U.S. Pat. No. 9,227,053, "Self-Expanding Electrode Cuff", issued on Jan. 5, 2016, and in Bonde et al. U.S. Pat. No. 8,340,785, "Self-Expanding Electrode Cuff", issued on Dec. 25, 2012, both of which are herein incorporated by reference.

In some examples, an implantable pulse generator (IPG) 1110 (FIG. 19A, 19B) forms part of a system including the cuff electrode 900, 960 and in which at least one electrode(s) may be located on a housing of the pulse generator IPG 1110.

It will be understood that, in a manner similar to that depicted in FIGS. 6A-6B (in which the cuff body releasably contacts a nerve 261) and/or FIGS. 7A-7K, the arrangements shown in FIGS. 18A, 18B also may be understood as schematically representing a method of neurostimulation and/or therapy to treat sleep disordered breathing, such as but not limited to obstructive sleep apnea, with nerve 261 omitted from FIGS. 18A-18B for illustrative clarity in such examples.

FIG. 19A is a block diagram schematically representing a neurostimulation system 1100, according to one example of the present disclosure. System 1100 comprises a pulse generator 1110, lead body 1102, and cuff electrode 1104 supported by the lead body 1102. In some examples, the cuff electrode 1104 comprises any one of the cuff electrodes as described in association with at least FIGS. 1-18B, FIGS. 24-27, and/or combinations of some features of such cuff electrodes. In some examples, neurostimulation system 1100 comprises a totally implantable system.

FIG. 19B is a block diagram schematically representing a neurostimulation system 1150, according to one example of the present disclosure. System 1150 comprises a pulse generator 1110 and a leadless cuff electrode 1154. In some examples, the cuff electrode 1154 comprises any one of the cuff electrodes as described in association with at least FIGS. 1-18B, FIGS. 24-27, and/or combinations of some features of such cuff electrodes. In some examples, neurostimulation system 1150 comprises a totally implantable system. However, in some examples, the pulse generator 1110 or a portion of the pulse generator 1110 is located external to the patient. The cuff electrode 1154 is in wireless communication with the pulse generator 1110 and/or related components to manage therapy, including applying electrical stimulation. Accordingly, in some examples the cuff electrode 1154 includes and/or is associated with an antenna and related circuitry to implement such wireless communication.

FIG. 20 is a block diagram schematically representing a control portion 1700, according to one example of the present disclosure. In some examples, control portion 1700 includes a controller 1702 and a memory 1704. In some examples, control portion 1700 provides one example implementation of a control portion forming a part of and/or implementing the implantable medical devices and methods as represented throughout the present disclosure in association with FIGS. 1-29B.

In general terms, controller 1702 of control portion 1700 comprises at least one processor 1703 and associated memories. The controller 1702 is electrically couplable to, and in communication with, memory 1704 to generate control signals to direct operation of at least some components of the devices, elements, components, functions, methods, etc. described throughout the present disclosure. In some examples, these generated control signals include, but are not limited to, employing manager 1705 stored in memory 1704 to manage therapy for sleep disordered breathing, including but not limited to applying nerve stimulation, in the manner described in at least some examples of the present disclosure. In some examples, such generated control signals may at least partially control selective stimulation via the different electrodes on a cuff electrode. It will be further understood that control portion 1700 (or another control portion) may also be employed to operate general functions of the various devices and/or components thereof described throughout the various examples of the present disclosure.

In response to or based upon commands received via a user interface (e.g. user interface 1710 in FIG. 21) and/or via machine readable instructions, controller 1702 generates control signals to implement therapy (including but not limited to nerve stimulation) and/or circuitry control in accordance with at least some of the previously described examples of the present disclosure. In some examples, controller 1702 is embodied in a general purpose computing device while in some examples, controller 1702 is incorporated into or associated with at least some of the associated components of the devices as described throughout the present disclosure.

For purposes of this application, in reference to the controller 1702, the term "processor" shall mean a presently developed or future developed processor (or processing resources) that executes sequences of machine readable instructions contained in a memory. In some examples, execution of the sequences of machine readable instructions, such as those provided via memory 1704 of control portion 1700 cause the processor to perform actions, such as operating controller 1702 to implement sleep disordered breathing (SDB) therapy (including but not limited to nerve stimulation), as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium, as represented by memory 1704. In some examples, memory 1704 comprises a computer readable tangible medium providing non-volatile storage of the machine readable instructions executable by a process of controller 1702. In some examples, hard wired circuitry may be used in place of or in combination with machine readable instructions to implement the functions described. For example, controller 1702 may be embodied as part of at least one application-specific integrated circuit (ASIC). In at least some examples, the controller 1702 is not limited to any specific combination of hardware circuitry and machine readable instructions, nor limited to any particular source for the machine readable instructions executed by the controller 1702.

FIG. 21 is a block diagram schematically representing user interface 1710, according to one example of the present disclosure. In some examples, user interface 1710 forms part or and/or is accessible via a device external to the patient and by which the implantable medical device (or portions thereof) may be at least partially controlled and/or monitored.

In some examples, user interface 1710 comprises a user interface or other display that provides for the simultaneous display, activation, and/or operation of features and attributes of an implantable medical device. In some examples, at least some portions or aspects of the user interface 1710 are provided via a graphical user interface (GUI). In some examples, as shown in FIG. 21, user interface 1710 includes display 1712 and input 1714.

Figure 22A:
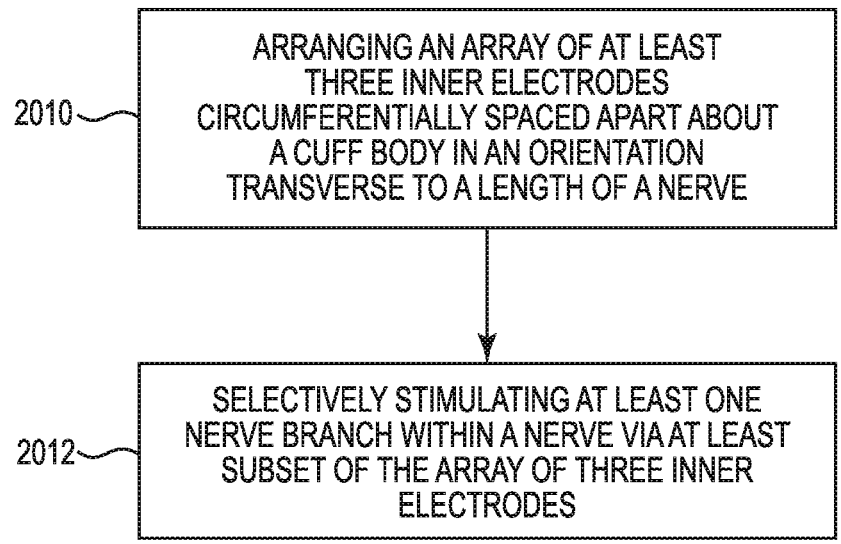

FIG. 22A is flow diagram schematically representing an example method 2000 of selective stimulation. As shown in FIG. 22A, in some examples method 2000 comprises arranging at least three inner electrodes circumferentially spaced apart about a cuff body (at 2010) and selectively stimulating at least one nerve branch within a nerve via a subset of the three inner electrodes in combination with two outer electrodes axially spaced apart from the inner electrodes (at 2012). In some examples, one or more of the inner electrodes may serve as an anode while the outer electrodes may serve as a cathode(s) to provide a guarded cathode arrangement.

In some examples, method 2000 may be implemented via at least some of substantially the same features and attributes as any one of (or a combination of) the devices, cuff electrodes, cuff bodies, electrode configurations, etc. as described in association with at least FIGS. 1-21 and/or 24-29B.

In addition, various additional aspects of method 2000 are presented below.

As shown in FIG. 22B at 2020, in some examples method 2000 may further comprise arranging a second array of at least two outer electrodes axially along a first orientation perpendicular to the second orientation and on respectively opposite ends of the first array, with each respective outer electrode spaced axially apart from the first array.

As shown at 2025 in FIG. 22C, in some examples method 2000 may further comprise selectively stimulating at least the first nerve branch with two electrodes of the first array while generally excluding a second nerve branch from stimulation.

As shown at 2030 in FIG. 22D, in some examples method 2000 may further comprise at least one of not activating a third electrode of the first array and activating the third electrode of the first array to selectively at least partially hyperpolarize the second nerve branch.

As shown at 2035 in FIG. 22E, in some examples method 2000 may further comprise selectively stimulating at least the first nerve branch via selectively stimulating the first nerve branch via a first electrode of the first array and separately selectively stimulating a third nerve branch via an adjacent second electrode of the first array.

As shown at 2040 in FIG. 22F, in some examples method 2000 may further comprise arranging the second array to comprise at least three electrodes, including the at least two outer electrodes, arranged axially along the first orientation and further comprising arranging an inner electrode axially between the at least two outer electrodes. In some such examples, the method 2000 further comprises arranging the inner electrode of the second array to also define one of the electrodes of the first array.

FIG. 22G is flow diagram schematically representing an example method 2100 of selective stimulation. As shown in FIG. 22G, in some examples method 2100 comprises arranging at least one array of first electrodes to extend axially on a cuff body in a first orientation along a length of a nerve (at 2110) and arranging a second array of second electrodes to extend circumferentially on the cuff body in a second orientation generally perpendicular to the first orientation (at 2120).

In some examples method 2100 may further comprise arranging the first electrodes to include an inner electrode and two outer electrodes on opposite ends of the inner electrode. In some such examples, one of the first electrodes selectively functions as one of the second electrodes. In some such examples, the three electrodes may be equally spaced apart.

As shown at 2140 in FIG. 22H, in some examples method 2100 may further comprise selectively stimulating at least a first nerve branch via selectively activating at least one second electrode in combination with selective activation with at least some of the first electrodes. In some such examples, the method 2100 at 2140 may comprise performing the selective activation via at least two second electrodes.

In some such examples, the method 2100 at 2110, 2120 may comprise selectively stimulating at least a first nerve branch via selectively activating at least some of the second electrodes without activating the first electrodes.

As shown at 2150 in FIG. 22I, in some examples method 2100 may further comprise arranging the cuff body to include an inner axial portion and two outer axial portions on opposite ends of the inner axial portion. In some such examples method 2100 may further comprise arranging the cuff body such that each respective axial portion includes an inner circumferential portion and two outer circumferential portions on opposite ends of the inner circumferential portion, as shown at 2155 in FIG. 22J.

Moreover, in some such examples, as shown at 2160 in FIG. 22K, method 2100 may further comprise arranging the outer circumferential portions to be shaped, and biased for releasable engagement of the outer circumferential portions relative to each other to define a reclosable lumen to encircle a nerve. In some such examples, method 2100 may comprise arranging the cuff body to form at least a 270 degree circumferential structure, which extends a full length of the cuff body. In some such examples, the cuff body may form an at least 360 degree circumferential structure.

With further reference to at least box 2150 in FIG. 22I, as shown at 2170 in FIG. 22L, method 2100 may further comprise arranging a respective one of the first electrodes to be in each of the respective inner and outer axial portions. As shown at 2175 in FIG. 22M, in some examples method 2100 may further comprise arranging the outer circumferential portions of each respective outer axial portion of the cuff body to be electrode-free. Moreover, in some such examples (such as at at least 2175), method 2100 may further comprise arranging the second electrodes to be located in at least one of the respective outer circumferential portions of the inner axial portion of the cuff body, as shown at 2180 in FIG. 22N.

In some such examples (such as at at least 2180), method 2100 may further comprise arranging the second electrodes comprises arranging two second electrodes on one outer circumferential portion of the inner axial portion, as shown at 2185 in FIG. 22O. In some such examples (such as at at least 2185), method 2100 may further comprise arranging the other respective outer circumferential portion to be electrode-free, as shown at 2190 in FIG. 22P. In some such examples (such as at at least 2190), method 2100 may further comprise arranging a stimulation signal vector to include one second electrode in an outer circumferential portion of the inner axial portion and the outer first electrode in each respective outer axial portion of the cuff body, as shown at 2195 in FIG. 22Q.

In some examples in which the second electrodes are to be located in at least one of the respective outer circumferential portions of the inner axial portion of the cuff body, some examples of method 2100 may further comprise arranging at least three second electrodes on one outer circumferential portion of the inner axial portion, as shown at 2200 in FIG. 22R. In some such examples, method 2100 may further comprise arranging the one outer circumferential portion to include at least one increased thickness portion to house the second electrode(s) and expose a portion of the second electrode within the lumen defined by the cuff body, as shown at 2210 in FIG. 22S.

In some such examples (such as at at least 2210), method 2100 may further comprise arranging the two second electrodes and an inner axial electrode to be equally spaced apart circumferentially, in the second orientation, about the contact surface of cuff body, as shown at 2220 in FIG. 22T. In some such examples (such as at 2220), method 2100 may further comprise arranging the at least one increased thickness portion to be oriented inwardly toward the nerve (e.g. FIGS. 14A, 14B, other). In some such examples (such as at 2220), method 2100 may further comprise arranging the at least one increased thickness portion to be oriented outwardly away from the nerve (e.g. FIGS. 18A, 18B, other).

With further reference to at least box 2150 in FIG. 22I, method 2100 may further comprise arranging one second electrode to be located on one outer circumferential portion in the inner axial portion of the cuff body and the other second electrode on the other respective outer circumferential portion in the inner axial portion of the cuff body, as shown at 2230 in FIG. 22U.

In some examples, the example method(s) (e.g. 2100, etc.) described in association with FIGS. 22G-22U may be implemented via at least some of substantially the same features and attributes as any one of (or a combination of) the devices, cuff electrodes, cuff bodies, electrode configurations, arrangements, methods, etc. as described in association with at least FIGS. 1-22F and/or 24-29B.

FIGS. 23-28 relate to several example cuff electrodes and/or associated methods including a distal extension for applying selective stimulation to at least some example nerve branch configurations. With this in mind, FIG. 23 is a diagram 3000 schematically representing an example nerve branch configuration 3010 at which an example cuff electrode may be mounted, such as at least some of the example cuff electrodes described in association with at least FIGS. 24-27. As shown in FIG. 23, nerve branch configuration 3010 comprises a main nerve 3011 from which various branches may diverge as the main nerve 3011 progresses distally. In some examples, nerve branch configuration 3010 may comprise a main branch 3020 (e.g. a protrusor branch) and one or more side branches, such as branch 3024 and/or branch 3032. In the particular example configuration 3010 shown in FIG. 23, branch 3024 corresponds to a retractor-related branch, which innervates a muscle to cause retraction of the tongue and branch 3022 causes neither protrusion nor retraction of the tongue, but may cause some deviation (3032) of the tongue from a resting position. As further shown in FIG. 23, branch 3024 and main branch 3020 may form a junction 3042 while branch 3020 and branch 3022 may form a junction 3044.

In examples in which one may desire to stimulate solely the main branch 3020, one desired placement of a cuff electrode (as represented by arrow 3040) may be distal of the dashed line 3050 such that the cuff electrode may solely engage the main branch 3020. However, in many instances, such a placement is not feasible because of the close proximity of the diverging branches 3032, 3024, surrounding non-nerve structures, etc. Accordingly, in some instances, at least one of the example cuff electrodes described below may enable securing the cuff electrode at site A (3052) while still positioning a distal extension of the cuff electrode in a position adjacent the main branch 3020 to stimulate solely (or primarily) the main branch 3020 to cause protrusion of the tongue without otherwise stimulating other deviation-causing nerve branches 3022, 3024.

It will be understood that the example nerve configuration shown in FIG. 23 is just one example and that other nerve configurations may be present, with the example devices and methods in FIGS. 24-27 being applicable for at least some alternate nerve configurations.

Figure 24:
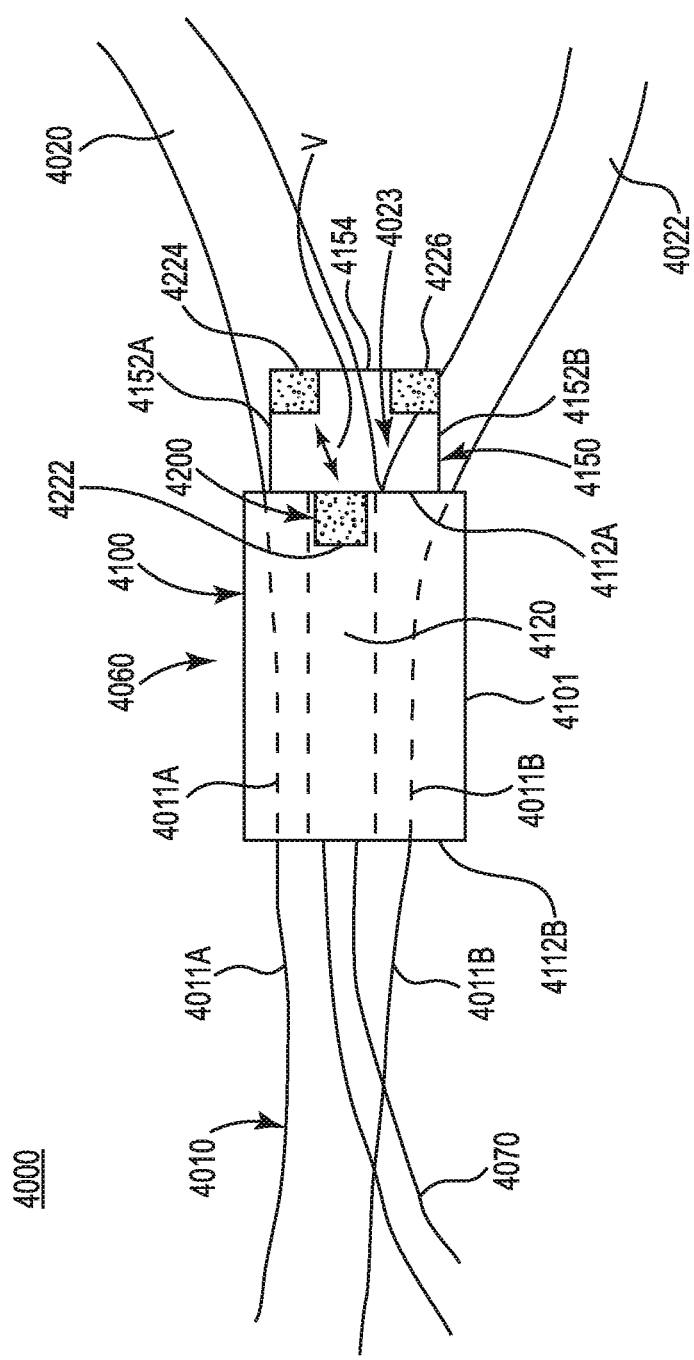
FIG. 24 is a diagram schematically representing an example cuff electrode including a distal extension engaged relative to an example nerve branch configuration.

FIG. 24 is a diagram 4000 schematically representing an example cuff electrode 4100 including a distal extension 4150 engaged relative to an example nerve branch configuration 4010. In some examples, example nerve branch configuration 4010 may comprise at least some of substantially the same features and attributes as example nerve branch configuration 3010 in FIG. 23.

In some examples, at least the cuff body 4101 (and cuff electrode generally) comprises at least some of substantially the same features and attributes of the cuff electrodes as previously described in association with FIGS. 1-18B.

As shown in FIG. 24, example implantable lead assembly 4060 includes an example cuff electrode 4100 releasably engaged about a main nerve 4010 in which the cuff electrode 4100 encircles the sides 4011A, 4011B of nerve 4010 and a spine 4120 of the cuff body 4101 extends generally parallel to the nerve 4010. The cuff body 4101 includes a main body extending between a proximal end 4112B and a distal end 4112A, with a distal extension 4150 extending distally from distal end 4112A. The distal extension 4150 may be formed of the same or similar material as cuff body 4101 in some examples, and comprises opposite sides 4152A, 4152B with distal end 4154. In some such examples, cuff electrode 4100 may extend from lead 4070 or other lead.

As further shown in FIG. 24, in some examples cuff electrode 4100 comprises an electrode array 4200 including multiple electrodes 4222, 4224, 4226. It will be understood that array 4200 may include a greater number or fewer number of electrodes than shown in FIG. 24, which may be distributed in patterns other than shown in FIG. 24. In the example shown in FIG. 24, one electrode 4222 may be located at or near a distal end 4112A of the main cuff body 4101 while the other two electrodes 4224, 4226 may be located on distal extension 4150, such as near distal end 4154. In the example array 4200 shown, the electrodes 4224 and 4226 are spaced apart laterally from each other such that one electrode 4224 is locatable adjacent first nerve branch 4020 and the other electrode 4226 is locatable adjacent second nerve branch 4022. In some examples, the first nerve branch 4020 corresponds to a nerve to be targeted for stimulation while the second nerve branch 4022 corresponds to a nerve branch to be excluded from stimulation, or at least not targeted for stimulation. In some examples, by utilizing a stimulation vector (V) between electrodes 4222 and 4224, the first nerve branch 4020 can be captured and stimulated while excluding stimulation of second nerve branch 4022. In some examples, the first nerve branch 4020 may correspond to a tongue protrusor nerve branch and the second nerve branch 4022 may correspond to a tongue retractor nerve branch or other nerve branch.

Among other features, via this electrode configuration distributed on the distal body extension 4150 and the main cuff body 4101, a specific nerve branch may be targeted for selective stimulation while still securing the cuff electrode 4100 in general on a main nerve 4010 proximal to the junction 4023 between the respective first and second nerve branches 4020, 4022. This avoids the complication of attempting to secure cuff body 4101 solely about first nerve branch 4020 and simplifies number and position of electrodes 4224, 4222 used to implement such stimulation.

In some examples, the main cuff body 4101 may omit any other electrodes besides electrode 4222. In some such examples, the main cuff body 4101 primarily acts to secure the cuff 4100 relative to the nerve while the distal extension 4150 carrying electrodes 4224, 4226 primarily acts as the active electrode portion of the cuff electrode 4100.

However, in some examples, in addition to the electrode 4222 (and the electrodes 4224, 4226 on distal extension 4150), the main cuff body 4101 may comprise at least some of substantially the same features and attributes of any one (or a combination of) of the example electrode configurations previously described in association with at least FIGS. 1-18B. In some such examples, at least some electrodes of the electrode array 4200 (of distal extension 4150) may be activated in a complementary manner with other electrodes of the main cuff body 4101.

Figure 25:
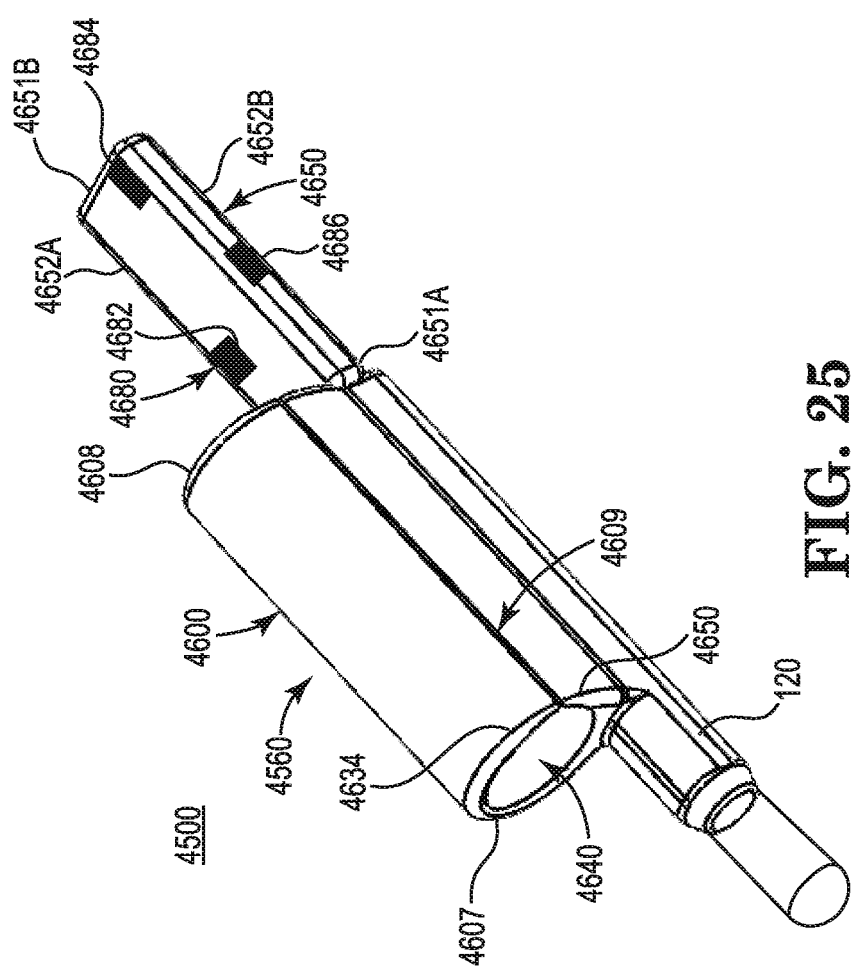
FIG. 25 is a diagram schematically representing an example cuff electrode including a distal extension.
Figure 26:
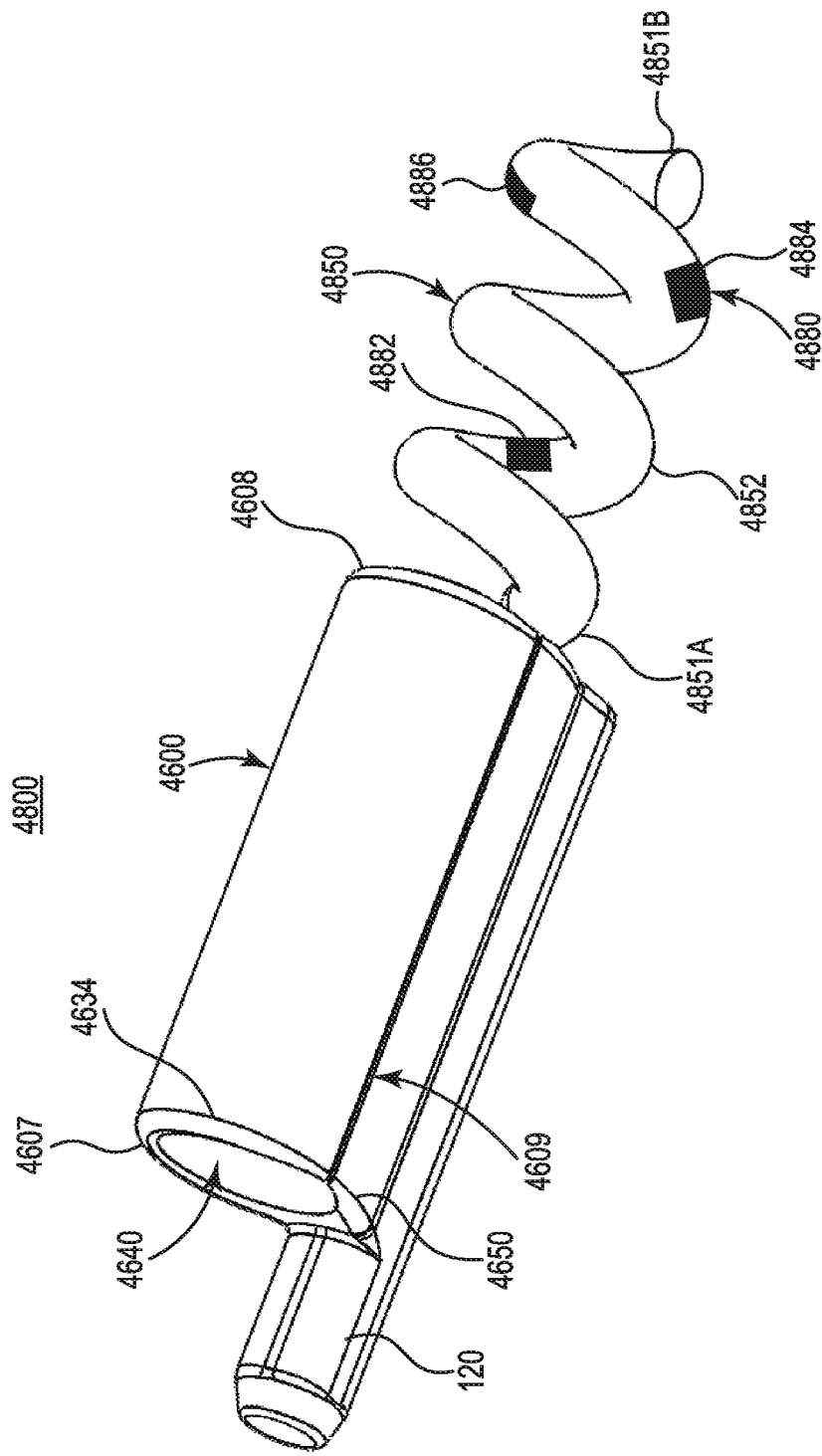
FIG. 26 is a diagram schematically representing an example cuff electrode including a distal extension.
Figure 27:
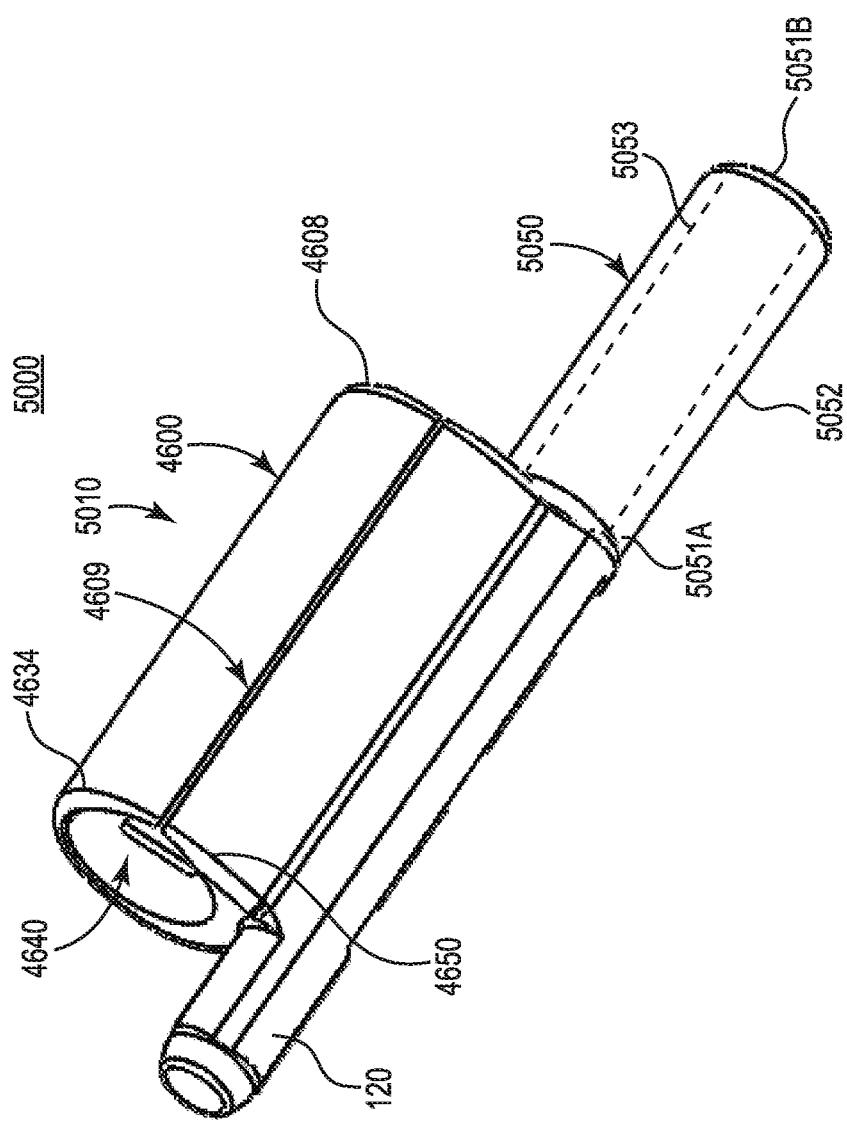
FIG. 27 is a diagram schematically representing an example cuff electrode including a distal extension.

As further illustrated in association with FIGS. 25-27, at least some more specific or alternate examples of a distal extension of an example cuff electrode 4100 may be positionable to be adjacent a nerve branch (e.g. 4020, 4022) without encircling the nerve branch (e.g. FIG. 25) and/or may be positionable to at least partially wrap about (e.g. encircle) the nerve branch (e.g. FIGS. 26, 27).

As apparent from the foregoing description associated with FIG. 24, it will be understood that FIG. 24 also may be viewed as schematically representing at least an example method of neurostimulation and/or therapy for treating sleep disordered breathing, such as but not limited to obstructive sleep apnea. In some examples, this arrangement and/or method may be employed other for treating bodily conditions and/or for other nerve structures.

FIG. 25 is a diagram 4500 schematically representing an example cuff electrode 4560 including a distal extension 4650, which in some examples may comprise at least some of substantially the same features and attributes as example cuff electrode 4100 including distal extension 4150 and/or the associated method of neurostimulation and/or therapy. As shown in FIG. 25, the cuff electrode 4560 comprises a main cuff portion 4600. In some examples, the main cuff portion 4600 comprises at least some of substantially the same features and attributes as the cuff body 101 (e.g., at least FIGS. 1-4), where similar reference numerals may refer to similar elements. For instance, main cuff portion 4600 may comprise opposing arms 4634, 4650 (like 134, 150) which are shaped and biased to define a lumen 4640 (like lumen 140) and which have ends in releasably contact at point 4609. The main cuff portion 4600 extends between a proximal end 4607 and distal end 4608. The main cuff body 4601 comprises and/or is supported by a base (e.g. 120 in FIG. 1), which in turn is supported by an elongate, resilient lead (not shown in FIG. 26).

As further shown in FIG. 25, distal extension 4650 extends from distal end 4608 of main cuff body 4601. In some examples, distal extension 4650 comprises an elongate generally rectangular element having a proximal end 4651A and opposite distal end 4651B, and opposite sides 4652A, 4652B.

The distal extension 4650 carries an array 4680 of electrodes 4682, 4684, 4686, which are distributed about a surface of the distal extension 4650. Via such configurations, one electrode 4684 may be at a distal end 4615B, while another electrode (e.g. 4682 or 4686) may be spaced proximally therefrom. In some examples, at least a pair of electrodes 4682, 4686 may be spaced apart laterally, such as being on or near opposite sides 4652A, 4652B of the distal extension 4650. Via at least some such example configurations, a given electrode may be locatable adjacent a target nerve branch or a non-target nerve branch (e.g. a branch to be excluded from stimulation or at which stimulation is inhibited). In some examples, just one electrode is carried on the distal extension 4650.

It will be understood that size, shape, and/or pattern of electrodes 4682, 4684, 4686 in FIG. 25 is merely one example, and that the electrodes 4682, 4684, 4686 may have different sizes, shape, and/or patterns than shown in FIG. 26. In addition, in some examples, the array 4680 may comprise a greater number or a fewer number of electrodes than shown in FIG. 25. Moreover, in some examples, the electrodes (e.g. 4682, 4684, 4686) on distal extension 4650 may comprise all of the electrodes for the entire cuff electrode 4560.

However, in some examples, the main cuff portion 4600 may comprise at least one electrode at its distal end 4608, similar to electrode 4222 in electrode array 4200 as shown in FIG. 24. Moreover, in some examples, the main cuff portion 4600 may comprise several electrodes, some of which may correspond to one of the example electrode configurations previously described in association with at least FIGS. 1-18B.

FIG. 26 is a diagram schematically representing an example cuff electrode 4800 including a distal extension 4850. In some examples, the cuff electrode 4800 may comprise at least some of substantially the same features and attributes as example cuff electrode 4100 including distal extension 4150 (FIG. 24) and/or main cuff portion 4600 (FIG. 25) and/or the associated method of neurostimulation and/or therapy. In some examples, example cuff electrode 4800 may comprise at least some of substantially the same features and attributes as example cuff electrode 4560 (FIG. 25), except having a distal extension 4850 having a different shape, size, etc. than distal extension 4650 in FIG. 25. As shown in FIG. 26, distal extension 4850 may comprise a helical coil body 4852 made of a resilient material biased to be at least partially self-wrappable about a first nerve branch (e.g. 4020 or 4022), without encircling the main nerve from which the first nerve branch extends.

The distal extension 4850 comprises a distal end 4851B and an opposite proximal end 4851A, which extends from the distal end 4608 of the main cuff portion 4600. An array 4880 of electrodes 4882, 4884, 4886 is distributed along various portions of the helical coil body 4852. As noted above, the electrodes 4882, 4884, 4886 may have a size, shape, position, and/or pattern different from shown in FIG. 26, and a greater number or fewer number of electrodes may comprise the array 4880.

In some examples, at least one of the electrodes 4882, 4884, 4886 is positioned on the coil body 4852 to be locatable adjacent a first nerve branch (e.g. 4020) targeted for stimulation. In some examples, at least one of the other/remaining electrodes 4882, 4884, 4886 is positioned on the helical coil body 4852 to be locatable adjacent a second nerve branch (e.g. 4022) to inhibit stimulation of the second nerve branch (e.g. via hyperpolarization). In some examples, the two different branches may be selective stimulated via some combination of the electrodes 4882, 4884, 4886 with or without inclusion of at least one electrode from main cuff portion 4600. With this in mind, in some examples the main cuff portion 4600 may omit electrodes while in some examples the main cuff portion 4600 may include at least some electrodes for stimulation, such as but not limited to any one of (or a combination of) the electrode configurations previously described in association with at least FIGS. 1-18B.

FIG. 27 is a diagram 5000 schematically representing an example cuff electrode 5010 including a distal extension 5050. In some examples, the cuff electrode 5010 may comprise at least some of substantially the same features and attributes as example cuff electrode 4100 including distal extension 4150 (FIG. 24) and/or the associated method of neurostimulation and/or therapy, and/or as example main cuff portion 4600 (FIG. 25). In some examples, cuff electrode 5010 may comprise at least some of substantially the same features and attributes as example cuff electrode 4560 (FIG. 25), except having a distal extension 5050 having a different shape, size, etc. than distal extension 4650 in FIG. 25. As shown in FIG. 27, distal extension 5050 may comprise a cylindrically-shaped body 5052 made of a resilient material biased to be at least partially self-wrappable about a nerve branch, such as first or second nerve branch 4020 or 4022, without encircling the main nerve from which the first nerve branch extends. In one aspect, body 5052 defines a lumen (as represented via dashed lines 5053) through one of the nerve branches (e.g. 4020, 4022) may extend.

The distal extension 5050 comprises a distal end 5051B and an opposite proximal end 5051A, which extends from the distal end 4608 of the main cuff portion 4600. The body 5052 may comprise a cuff body like main cuff body 4601 or another type of cuff body having arms or other elements biased to selectively wrap about a nerve branch. In some examples, an interior surface of the body 5052 (e.g. lumen 5053) may carry an array of electrodes distributed along various portions of the coil body 5052 such that at least one of such electrodes may be locatable adjacent a first nerve branch (e.g. 4020) targeted for stimulation. The array of electrodes may be arranged in a pattern as shown in FIG. 24, 25, or 26 or may be arranged in a different pattern.

In some examples, at least one other/remaining electrodes may be positioned on an exterior of body 5052 to be locatable adjacent a second nerve branch (e.g. 4022) to stimulate or to inhibit stimulation of the second nerve branch. In some examples, the two different branches (e.g.

4020, 4022) may be selectively stimulated via some combination of the electrodes of distal extension 5050 with or without inclusion of at least one electrode from main cuff portion 4600. With this in mind, in some examples the main cuff portion 4600 may omit electrodes while in some examples the main cuff portion 4600 may include at least some electrodes for stimulation, such as but not limited to any one of (or a combination of) the electrode configurations previously described in association with at least FIGS. 1-18B.

Figure 28A:
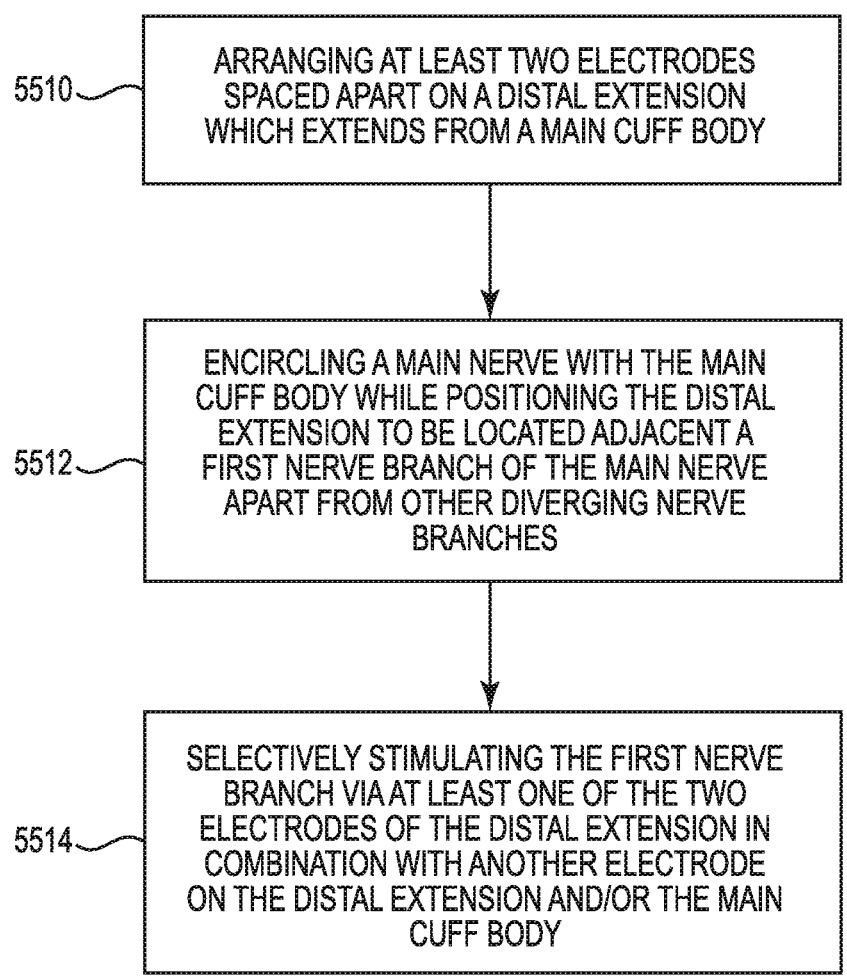

FIG. 28A is flow diagram schematically representing an example method 5500 of selective stimulation. As shown in FIG. 28A, in some examples method 5500 comprises arranging at least two electrodes spaced apart on a distal extension, which extends from a main cuff body (at 5510), encircling a main nerve with the main cuff body while positioning the distal extension to be located adjacent a first nerve branch (of the main nerve) apart from other diverging nerve branches (at 5512), and selectively stimulating the first nerve branch via at least one of the two electrodes of the distal extension in combination with another electrode (at 5514).

As shown at 5530 in FIG. 28B, method 5500 may further comprise performing the selective stimulation in combination with another electrode supported by the distal extension and/or the main cuff body. In some examples, the distal extension may carry just one electrode.

In some examples, method 5500 may be implemented via at least some of substantially the same features and attributes as any one of (or a combination of) the devices, cuff electrodes, cuff bodies, electrode configurations, etc. as described in association with at least FIGS. 24-27 and/or FIGS. 1-22.

As shown at 5535 in FIG. 28C, in some examples method 5500 may further comprise utilizing at least some electrodes of a main cuff body to stimulate a main nerve in a complementary manner with stimulating a particular nerve branch via at least one of the electrodes of the distal extension.

However, in some examples the electrodes of the main cuff body do not contribute to stimulating the main nerve and/or the main cuff body omits any electrodes (i.e. the main cuff body is electrode-free). Accordingly, in some such examples the main cuff body may primarily act to secure the overall cuff electrode relative to the main nerve, also thereby at least partially securing or supporting the distal extension relative to nerve branches distal to the main cuff body (and the main nerve).

In some examples, the main cuff body may comprise at least one electrode at its distal end (e.g. 4608 such as in FIG. 24) to enable stimulation in cooperation with at least one electrode on a distal extension from the main cuff body.

As shown at 5540 in FIG. 28D, in some examples method 5500 may further comprise arranging the distal extension to be at least partially self-wrappable about the first nerve branch without encircling the main nerve. In some such examples, the method may comprise arranging the distal extension as at least one of a helical coil body (e.g. FIG. 26) and a cylindrically-shaped body (e.g. FIG. 27).

As shown at 5550 in FIG. 28E, in some examples method 5500 may further comprise arranging the distal extension to extend along a portion of the first nerve branch without at least partially wrapping about the first nerve branch. In some such examples, method 5500 may further comprise arranging the distal extension as an elongate rectangular element (e.g. FIG. 24 or 25).

Figure 29A:
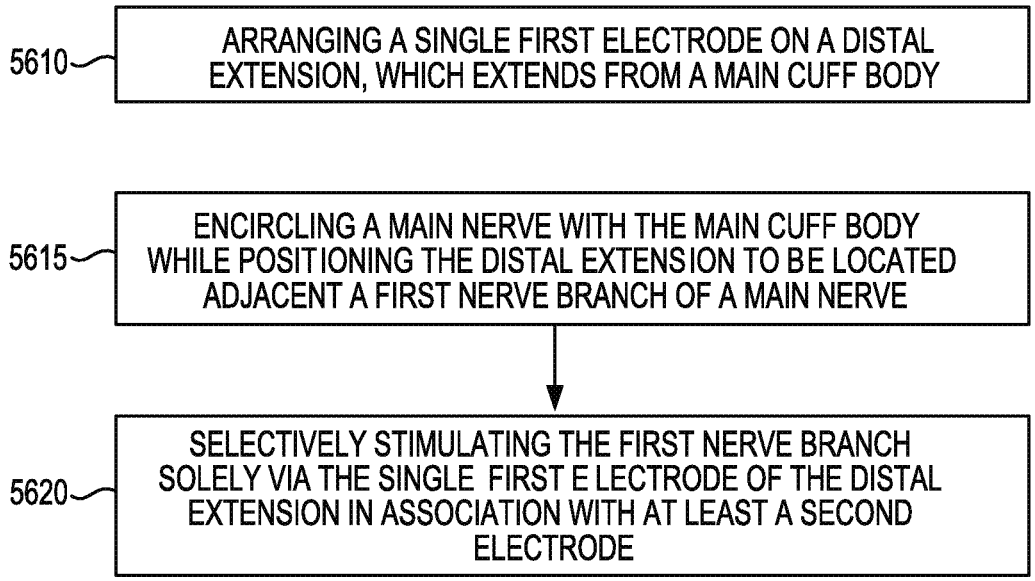
FIGS. 29A-29B are each a flow diagram, or a portion of a flow diagram, schematically representing an example method.
Figure 29B:

As shown at 5610 in FIG. 29A, in some examples method 5500 may be implemented as a method 5600 comprising arranging a single first electrode on a distal extension, which extends from a main cuff body. At 5615, method 5600 comprises encircling a main nerve with the main cuff body while positioning the distal extension to be located adjacent a first nerve branch of a main nerve. As shown at 5620, method 5600 comprises selectively stimulating the first nerve branch solely via the single first electrode of the distal extension in association with at least a second electrode. As shown at 5640 in FIG. 29B, in some examples method 5600 may further comprise arranging the second electrode to be on the main cuff body. In one aspect, in some such examples the first nerve branch extends separately and distally from proximal portions of the main nerve in which the first nerve branch is enclosed within the main nerve.

Although specific examples have been illustrated and described herein, it will be appreciated by those of ordinary skill in the art that a variety of alternate and/or equivalent implementations may be substituted for the specific examples shown and described without departing from the scope of the present disclosure. This application is intended to cover any adaptations or variations of the specific examples discussed herein.

The invention claimed is:

1. A method of fabricating a cuff electrode comprising:
forming a cuff body to define a base, a first arm, and a second arm,
wherein:
the first arm defines at least one increased thickness portion and extends from the base in a first circumferential direction to a distal end,
the at least one increased thickness portion is circumferentially spaced from the base and from the distal end,
a thickness of the at least one increased thickness portion at an apex thereof is greater than a thickness of at least a portion of the first arm circumferentially between the at least one increased thickness portion and the base,
and further wherein the second arm extends from the base in a second circumferential direction opposite the first circumferential direction to exteriorly overlap a portion of the first arm including the at least one increased thickness portion;
and further wherein the first and second arms are biased to self-assume a closed configuration of the cuff body in which the second arm exteriorly overlaps the first arm;
arranging at least one array of first electrodes to extend axially on the cuff body in a first orientation; and
arranging a second array of second electrodes to extend circumferentially on the cuff body in a second orientation, including at least one electrode of the second array of second electrodes being housed by the first arm at a location radially aligned with the at least one increased thickness portion.

2. The method of claim 1, wherein:
the at least one first array of first electrodes includes an inner electrode and two outer electrodes on opposite ends of the inner electrode.

3. The method of claim 2, wherein one of the first electrodes selectively functions as one of the second electrodes.

4. The method of claim 3, comprising:
arranging the electrodes of the first array of first electrodes to be equally spaced apart along the cuff body.

5. The method of claim 1, comprising:
forming the cuff body to include an inner axial portion and two outer axial portions on opposite ends of the inner axial portion;
wherein each respective axial portion includes:
an inner circumferential portion and two outer circumferential portions on opposite ends of the inner circumferential portion.

6. The method of claim 5, comprising:
forming the outer circumferential portions to be shaped, and biased for releasable engagement of the outer circumferential portions relative to each other to define a reclosable lumen to encircle a nerve.

7. The method of claim 6, comprising:
forming the cuff body to define an at least 360 degree circumferential structure, which extends a full length of the cuff body.

8. The method of claim 6, comprising:
arranging a respective one of the first electrodes to be in each of the respective inner and outer axial portions;
wherein the outer circumferential portion of each respective outer axial portion of the cuff body are electrode-free.

9. The method of claim 8, comprising:
arranging the second electrodes to be located in at least one of the respective outer circumferential portions of the inner axial portion of the cuff body.

10. The method of claim 9, wherein arranging the second electrodes comprises:
arranging two second electrodes on one outer circumferential portion of the inner axial portion.

11. The method of claim 10, wherein the other respective outer circumferential portion is electrode-free, the method further comprising the cuff electrode being operable to generate a stimulation signal vector by one of the second electrodes in the outer circumferential portion of inner axial portion and the first electrode in each respective outer axial portion of the cuff body.

12. The method of claim 9, wherein arranging the second electrodes further comprises:
arranging at least three second electrodes on one outer circumferential portion of the inner axial portion.

13. The method of claim 1, wherein arranging a second array of second electrodes includes exposing a portion of the second electrodes within a lumen defined by the cuff body.

14. The method of claim 1, comprising:
arranging the second electrodes to be equally spaced apart circumferentially, in the second orientation, about a contact surface of the cuff body.

15. The method of claim 1, wherein forming the cuff body includes defining the at least one increased thickness portion to be oriented inwardly toward a center of the cuff body.

16. The method of claim 1, wherein forming the cuff body includes defining the at least one increased thickness portion to be oriented outwardly away from a center of the cuff body.

17. The method of claim 1, wherein the at least one increased thickness portion includes a first increased thickness portion and a second increased thickness portion, and further wherein arranging the second array of second electrodes includes housing a first one of the second electrodes at a location radially aligned with the first increased thickness portion and housing a second one of the second electrodes at a location radially aligned with the second increased thickness portion.

18. The method of claim 17, wherein the first increased thickness portion is circumferentially spaced from the second increased thickness portion.

19. The method of claim 18, wherein forming the cuff body includes forming a thickness of the first arm at the first and second increased thickness portions to be greater than a thickness of the first arm along an entirety of a region of the first arm circumferentially between the first and second increased thickness portions.

20. The method of claim 18, wherein the second arm exteriorly overlaps a portion of the first arm along a region of overlap, and further wherein the region of overlap includes the first and second increased thickness portions.

21. The method of claim 18, wherein the first one of the second electrodes is exposed to a lumen of the cuff body at the first increased thickness portion, and further wherein the second one of the second electrodes is exposed to the lumen at the second increased thickness portion.

22. The method of claim 21, wherein the base, the first arm, and the second arm combine to define a nerve-contact surface of the lumen, and further wherein the first and second ones of the second electrodes combine to define a radius at the nerve-contact surface that is less than a radius of a reminder of the nerve-contact surface.

23. The method of claim 18, wherein the first and second increased thickness portions each project radially outwardly relative to an outer surface of the first arm, and further wherein the second arm is biased into contact with the first and second increased thickness portions.

24. The method of claim 23, wherein a gap is formed between the first and second arms along a circumferential region between the first and second increased thickness portions.

25. The method of claim 1, wherein the second arm includes a proximal portion and a distal portion, and further wherein the proximal portion extends from the base, and even further wherein the distal portion extends from the proximal portion to a distal end, and even further wherein a thickness of the proximal portion is greater than a thickness of the distal portion to define a shelf for selectively receiving the distal end of the first arm.

* * * * *